(12) United States Patent
Ema et al.

(10) Patent No.: US 8,362,237 B2
(45) Date of Patent: Jan. 29, 2013

(54) OPTICAL-ISOMER SEPARATING AGENT FOR CHROMATOGRAPHY AND PROCESS FOR PRODUCING THE SAME

(75) Inventors: Tadashi Ema, Okayama (JP); Takashi Sakai, Okayama (JP); Daisuke Tanida, Okayama (JP); Kyoko Sugita, Okayama (JP); Atsushi Ohnishi, Himeji (JP); Kenichiro Miyazawa, Myoko (JP)

(73) Assignees: National University Corporation Okayama University, Okayama-shi, Okayama (JP); Daicel Chemical Industries, Ltd., Osaka-shi, Osaka (JP)

( * ) Notice: Subject to any disclaimer, the term of this patent is extended or adjusted under 35 U.S.C. 154(b) by 263 days.

(21) Appl. No.: 12/735,516

(22) PCT Filed: Jan. 30, 2009

(86) PCT No.: PCT/JP2009/051616
§ 371 (c)(1), (2), (4) Date: Jul. 22, 2010

(87) PCT Pub. No.: WO2009/096540
PCT Pub. Date: Aug. 6, 2009

(65) Prior Publication Data
US 2010/0292464 A1 Nov. 18, 2010

(30) Foreign Application Priority Data
Jan. 31, 2008 (JP) ................................. 2008-021027

(51) Int. Cl.
*C07D 471/18* (2006.01)

(52) U.S. Cl. ....................................................... 540/456
(58) Field of Classification Search .................. 540/456
See application file for complete search history.

(56) References Cited

PUBLICATIONS

Versatile and Practical Macrocyclic Reagent with Multiple Hydrogen-Bonding Sites for Chiral Discrimination in NMR, by Tadashi Ema et al, Journal of the American Chemical Society, vol. 129, No. 34, 2007, pp. 10591-10596.
Macrocyclic Antibiotics as a New Class of Chiral Selectors for Liquid Chromatography, by Daniel Armstrong et al, Analytical Chemistry, vol. 66, No. 9, 1994, pp. 1473-1484.
Practical Macrocyclic Chiral Discriminating Reagents Driven by Hydrogen Bonds, by Tadashi Ema et al, Preprints of 87th Annual Meeting of Chemical Society of Japan in Spring Koen Yokoshu II, Report No. 4 J2-08, 2007, p. 1296.
A Versatile Chiral Shift Reagent Based on Host-Guest Chemistry: Synthesis and Function, by Tadashi Ema et al, Preprints of 86th Annual Meeting of Chemical Society of Japan in Spring Koen Yokoshu II, 2006, Report No. 1 G6-46, p. 930.
A Chiral $A_2B_2$ Macrocyclic Minireceptor with Extreme Enantioselectivity, by Francesco Gasparrini et al, Organic Letters, vol. 4, No. 23, 2002, pp. 3993-3996.

*Primary Examiner* — Bruck Kifle
(74) *Attorney, Agent, or Firm* — Flynn, Thiel, Boutell & Tanis, P.C.

(57) ABSTRACT

A novel optical-isomer separating agent for chromatography is provided which has, as a chiral selector, a macrocyclic amide compound having the ability to function as a chiral shift agent. The optical-isomer separating agent for chromatography is formed by bonding, with a carrier by chemical bonding, a specific ring structure containing an asymmetry recognition site, an amide group as a hydrogen-bond donor site, and a hydrogen-bond acceptor site.

11 Claims, 43 Drawing Sheets

OPTICAL-ISOMER SEPARATING AGENT FOR CHROMATOGRAPHY AND PROCESS FOR PRODUCING THE SAME

TECHNICAL FIELD

The present invention relates to an optical-isomer separating agent for chromatography containing an optically active, macrocyclic compound having an asymmetry recognition function utilizing multiple hydrogen bonds in a chiral cavity and a process for producing the agent.

BACKGROUND ART

Along with an increase in number of pharmaceuticals, agricultural chemicals, and liquid crystal materials containing compounds each having an asymmetric carbon, the need for accurately determining the optical purity of each of those compounds and their synthesis intermediates has been arising. NMR involving the utilization of a chiral derivatizing reagent or a chiral shift reagent (or a chiral solvation reagent), high performance liquid chromatography (HPLC) and gas chromatography, each involving the use of a chiral column packed with a chiral stationary phase, have each been known as a method of determining the optical purity.

Of those, the HPLC has been widely acknowledged as a method showing highly reliable results of analysis for a wide range of compounds. Moreover, the HPLC has the following characteristic. That is, the method enables the fractionation of chiral compounds as well as the analysis of the compounds. A stationary phase formed of a carrier such as a silica gel and a chiral selector supported by being covalently bonded to the carrier has been generally known as the chiral stationary phase used in the HPLC. For example, a stationary phase obtained by covalently bonding a cyclic amide compound to a silica gel as a carrier has been known as such chiral stationary phase (see, for example, Non-patent Documents 1 and 2).

Meanwhile, for example, a cyclic amide compound having an ability to function as a chiral shift reagent capable of asymmetry recognition by an NMR spectrum has been reported as the chiral shift reagent used in the NMR (see, for example, Non-patent Document 3). However, with particular regard to a compound having an ability to function as a chiral shift reagent, it has been known that a recognition ability is exerted only in an aprotic solvent such as deuterated chloroform and that causing a protic deuterated solvent such as an alcohol to coexist reduces the recognition ability. Meanwhile, assorted solvents including an alcohol are each used as a moving phase for a recognition agent for chromatography. Accordingly, it cannot be expected that the very asymmetry recognition ability of the compound having an ability to function as a chiral shift reagent is exerted, and investigations on the exertion have hardly been conducted.

Non-patent Document 1: D. W. Armstrong, Y. Tang, S. Chen, Y. Zhou, C. Bagwill, J.-R. Chen, Macrocyclic antibiotics as a new class of chiral selectors for liquid chromatography. Anal. Chem., 66(9), 1473-1484 (1994).

Non-patent Document 2: F. Gasparrini, D. Misiti, M. Pierini, C. Villani, A chiral A2B2 macrocyclic minireceptor with extreme enantioselectivity. Org. Lett., 4(23), 3993-3996 (2002).

Non-patent Document 3: T. Ema, D. Tanida, T. Sakai, Versatile and practical macrocyclic reagent with multiple hydrogen-bonding sites for chiral discrimination in NMR. J. Am. Chem. Soc., 129(34), 10591-10596 (2007).

DISCLOSURE OF THE INVENTION

Problems to be Solved by the Invention

The present invention provides a novel optical-isomer separating agent for chromatography having a ring structure having an ability to function as a chiral shift reagent as a chiral selector.

Means for Solving the Problems

The present invention is based on such a finding that a composition obtained by chemically bonding, to a carrier, a cyclic asymmetric molecule recognition site containing an asymmetry recognition site in the cyclic amide compound having an ability to function as a chiral shift reagent, a hydrogen-bond donor site, and a hydrogen-bond acceptor site has optical-isomer separating performance in chromatography.

That is, the present invention provides an optical-isomer separating agent for chromatography, which is obtained by causing a carrier to support a compound represented by the following general formula (1) by chemical bonding.

[Chem 1]

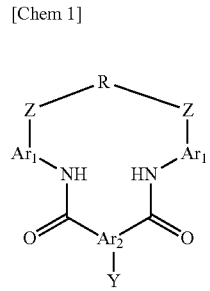

(1)

In the general formula (1), R represents an organic group having an asymmetric structure having 2 to 30 carbon atoms, Ar1's each independently represent a divalent group having hydrogen-bond accepting property or an aromatic group having 3 to 10 carbon atoms, Ar2 represents an aromatic or heterocyclic group having 3 to 14 carbon atoms, Z's each independently represent a single bond or a divalent group, and Y represents a group which chemically bonds to the carrier.

Further, the present invention provides the separating agent, in which R in the general formula (1) is represented by the following general formula (2), (3), or (4), or the following structural formula (5) or (6).

[Chem 2]

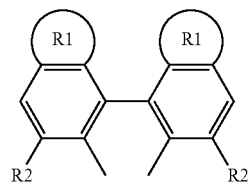

(2)

-continued (3)
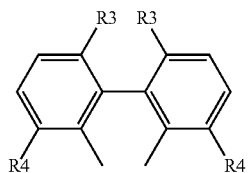

(4)
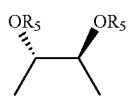

(5)
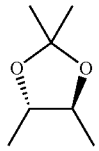

(6)

In the general formula (2), R1 rings each independently represent an aromatic ring, an aliphatic ring, or no ring, R2's each independently represent a hydrogen atom, a linear or branched alkyl group having 1 to 5 carbon atoms, an aromatic group, an ester group, or a halogen atom, in the general formula (3), R3's each independently represent a hydrogen atom, a linear or branched alkyl group having 1 to 5 carbon atoms, a nitro group, an aromatic group, an ester group, or a halogen atom, R4's each independently represent a hydrogen atom, a linear or branched alkyl group having 1 to 5 carbon atoms, an aromatic group, an ester group, or a halogen atom, and in the general formula (4), R5's each independently represent a hydrogen atom, a linear or branched alkyl group having 1 to 5 carbon atoms, an aromatic group, or an ester group.

Further, the present invention provides the separating agent, in which R in the general formula (1) is represented by the following structural formula (7). It should be noted that an absolute configuration of the general formula (7) may be (R) or (S).

[Chem 3]

(7)
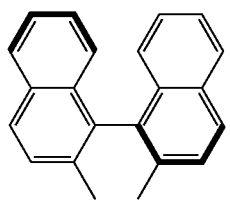

Further, the present invention provides the separating agent, in which the divalent group having hydrogen-bond accepting property is a heterocyclic group having 3 to 10 carbon atoms.

Further, the present invention provides the separating agent, in which Ar1's in the general formula (1) are each represented by the following structural formula (8) and Ar2 in the general formula (1) is represented by the following structural formula (9).

[Chem 4]

(8)
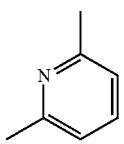

(9)
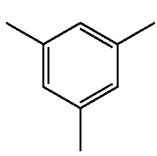

Further, the present invention provides the separating agent, in which Z's in the general formula (1) each represent a divalent organic group containing at least one of oxygen, nitrogen, and sulfur.

Further, the present invention provides the separating agent, in which Z's in the general formula (1) each are any one of groups represented by the following structural formulae (10) to (15).

[Chem 5]

—O—$CH_2$—  (10)

—O—$CH_2$—CO—NH—  (11)

—O—CO—NH—  (12)

—$CH_2$—CO—NH—  (13)

—$CH_2$—NH—CO—  (14)

—S—$CH_2$—CO—NH—  (15)

Further, the present invention provides the separating agent, in which the carrier is a silica gel.

Further, the present invention provides the separating agent, in which Y in the general formula (1) is a group that reacts with a silanol group to form a siloxane bond.

Further, the present invention provides the separating agent, in which Y's in the general formula (1) each are any one of groups represented by the following general formulae (16) to (20).

[Chem 6]

—CO—NH—$(CH_2)_n$—$Si(OEt)_3$  (16)

—S—$(CH_2)_3$—O—$(CH_2)_n$—$Si(OEt)_3$  (17)

—NH—$CH_2$—CH(OH)—$(CH_2)_n$—$Si(OEt)_3$  (18)

—CH=N—$(CH_2)_n$—$Si(OEt)_3$  (19)

—O—$CH_2$—CO—NH—$(CH_2)_n$—$Si(OEt)_3$  (20)

In the general formulae (16) to (20), n represents an integer of 1 to 20.

Further, the present invention provides a process for producing an optical-isomer separating agent for chromatography, the process including the steps of: causing two equivalents of a diamine (II) represented by the following general formula (II) and one equivalent of an acid compound (I) represented by the following general formula (I) or an acid compound (IV) represented by the following general formula (IV) to react with each other to obtain a diamine (III) represented by the following general formula (III) or a diamine (VII) represented by the following general formula (VII); causing equal equivalents of the diamine (III) or (VII) and the acid compound (IV) or (I) to react with each other to obtain a cyclic amide compound (V) represented by the following general formula (V); and causing Y of the cyclic amide compound (V) and a carrier to react with each other directly or through a crosslinking group to obtain an optical-isomer separating agent for chromatography represented by the following general formula (VI).

Further, the present invention provides the process, in which R is represented by the structural formula (7) (the absolute configuration of the general formula (7) may be (R) or (S)).

Further, the present invention provides the process, in which Ar1's are each represented by the structural formula (8) and Ar2 is represented by the structural formula (9).

Further, the present invention provides the process, in which Z's each are —O—, —O—CH$_2$—, —CH$_2$—, or —S—CH$_2$—.

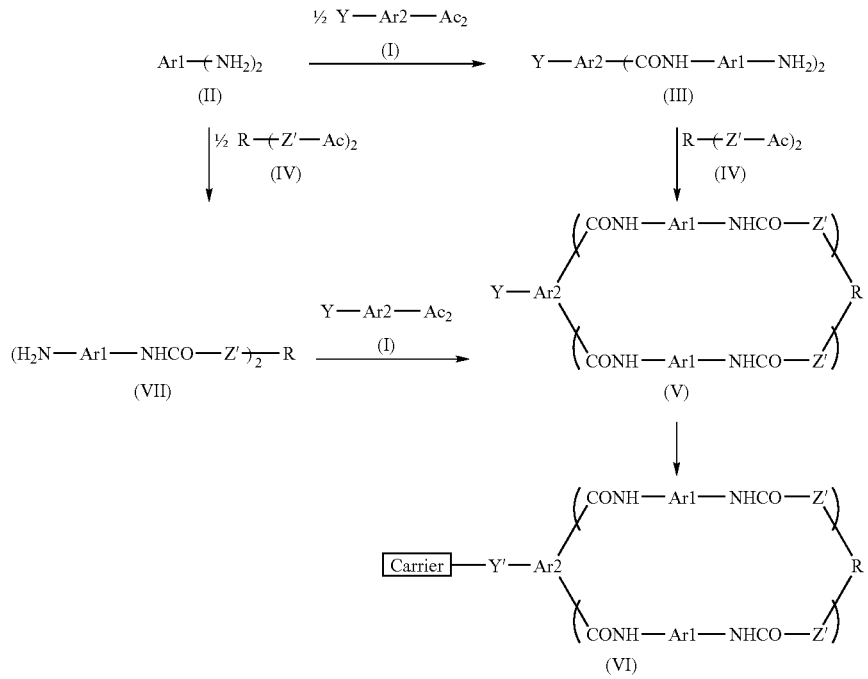

In the general formulae (I), (III), (V), and (VI), Ar2 represents an aromatic or heterocyclic group having 3 to 10 carbon atoms and Y represents a group which chemically bonds to the carrier or a group having a precursor structure thereof, in the general formulae (II), (III), and (V) to (VII), Ar1's each independently represent an aromatic or heterocyclic group having 3 to 10 carbon atoms, in the general formulae (IV) to (VII), R represents an organic group having an asymmetric structure having 2 to 30 carbon atoms and Z's each independently represent a single bond or a divalent group, in the general formula (VI), Y' represents a group chemically bonded to the carrier, and in the general formulae (I) and (IV), Ac represents a carboxyl group or —COCl.

Further, the present invention provides the process including the steps of: causing two equivalents of the diamine (II) represented by the general formula (II) and one equivalent of the acid compound (I) represented by the general formula (I) to react with each other to obtain the diamine (III) represented by the general formula (III); causing equal equivalents of the diamine (III) and the acid compound (IV) to react with each other to obtain the cyclic amide compound (V) represented by the general formula (V); and bonding Y of the cyclic amide compound (V) and the carrier to each other through the crosslinking group to obtain the optical-isomer separating agent for chromatography represented by the general formula (VI).

Further, the present invention provides the process, in which the carrier is a silica gel.

Further, the present invention provides the process, in which the silica gel has been subjected to surface modification with a group serving as the crosslinking group.

Further, the present invention provides the process, in which the group serving as the crosslinking group is any one of groups represented by the following general formulae (21) to (25).

[Chem 8]

 (21)

 (22)

 (23)

 (24)

-continued

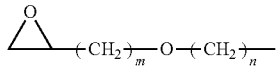
(25)

In the general formulae (21) to (25), m and n each represent an integer of 1 to 20.

Effect of the Invention

The present invention may provide a novel optical-isomer separating agent for chromatography having a ring structure having an ability to function as a chiral shift reagent as a chiral selector.

BEST MODE FOR CARRYING OUT THE INVENTION

Figure 1:
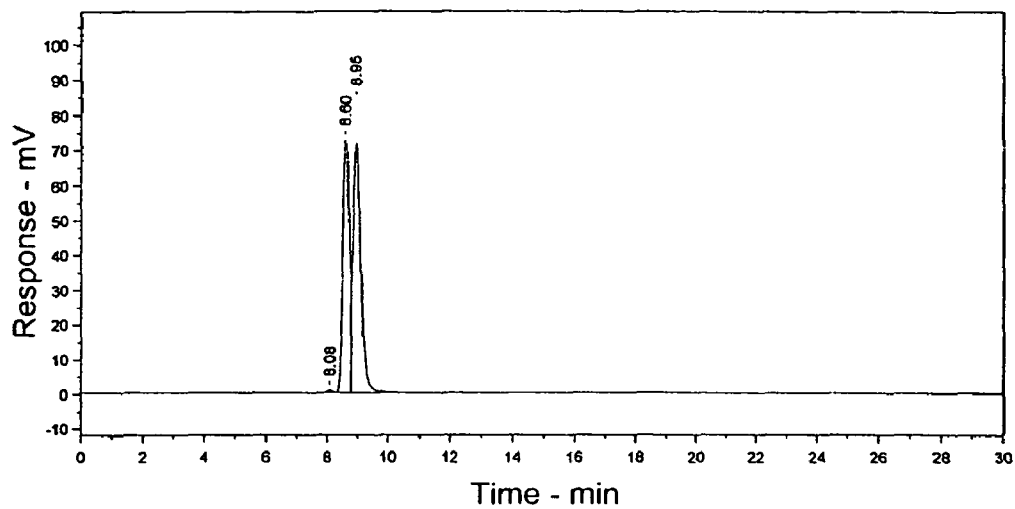
FIG. 1 illustrates a chromatogram of Evaluation Sample 1 in Evaluation 1 of Example 3.
Figure 2:
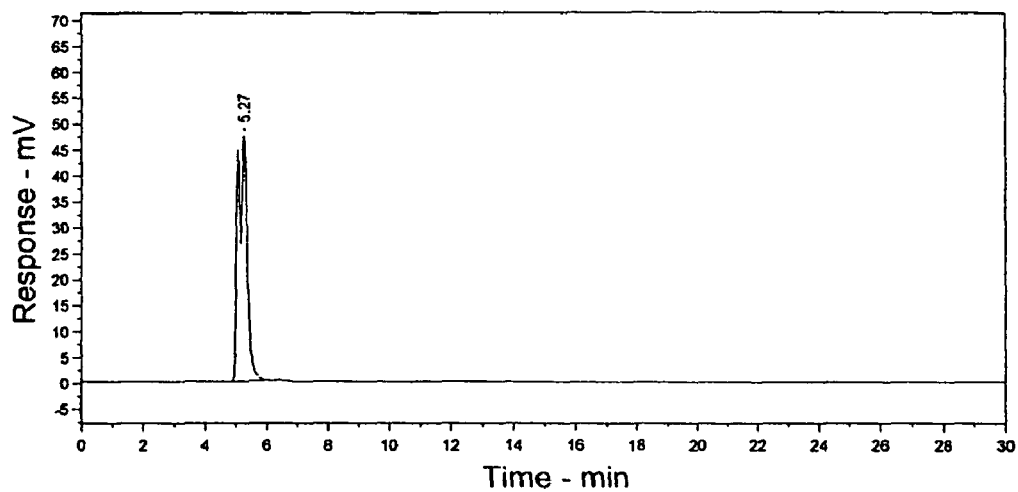
FIG. 2 illustrates a chromatogram of Evaluation Sample 2 in Evaluation 1 of Example 3.
Figure 3:
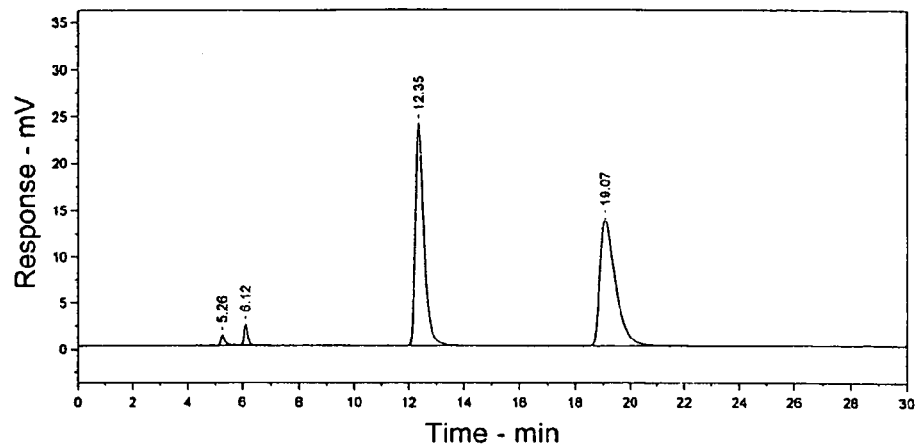
FIG. 3 illustrates a chromatogram of Evaluation Sample 3 in Evaluation 1 of Example 3.
Figure 4:
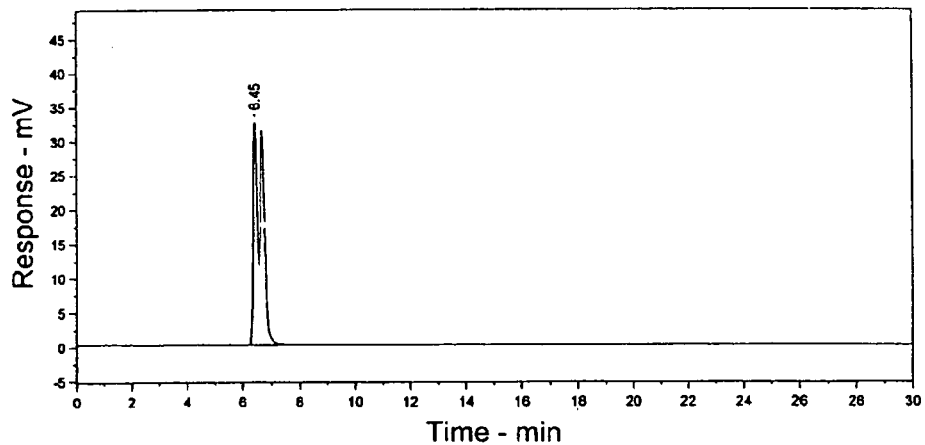
FIG. 4 illustrates a chromatogram of Evaluation Sample 4 in Evaluation 1 of Example 3.
Figure 5:
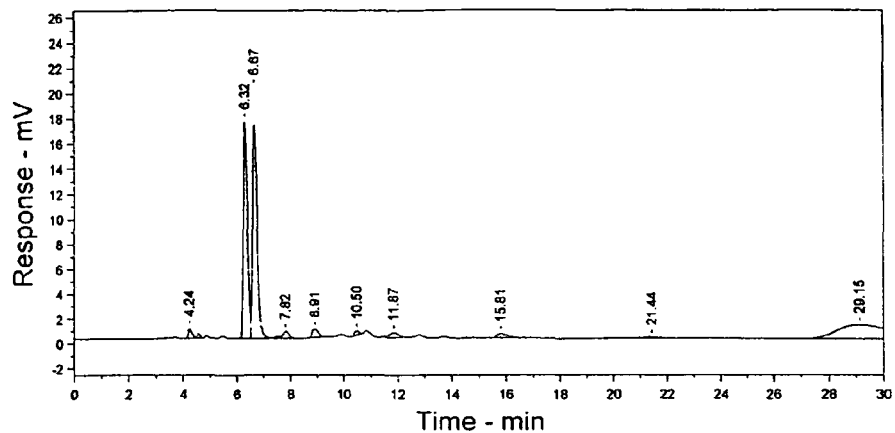
FIG. 5 illustrates a chromatogram of Evaluation Sample 5 in Evaluation 1 of Example 3.
Figure 6:
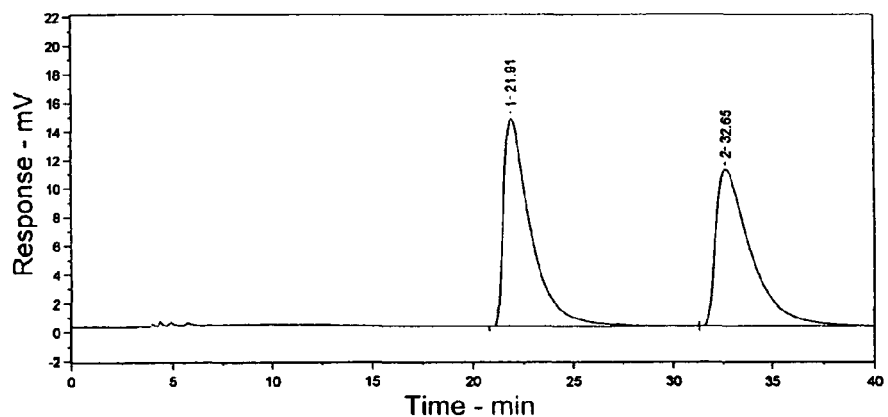
FIG. 6 illustrates a chromatogram of Evaluation Sample 6 in Evaluation 1 of Example 3.
Figure 7:
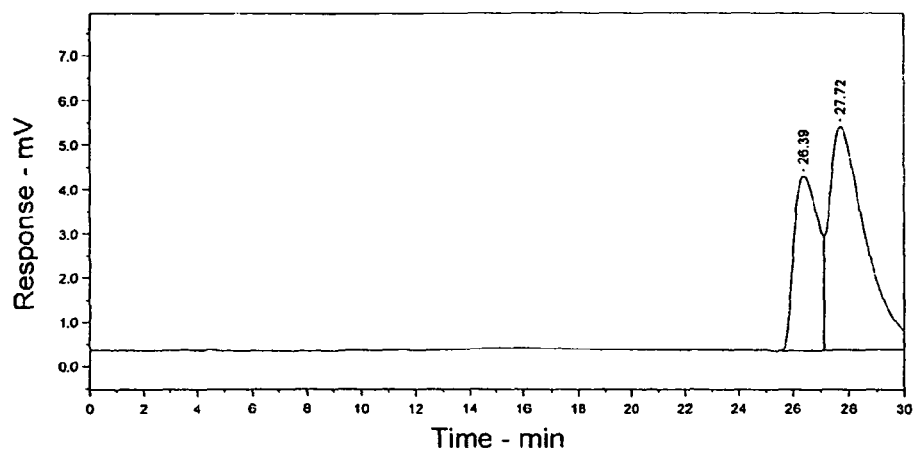
FIG. 7 illustrates a chromatogram of Evaluation Sample 7 in Evaluation 1 of Example 3.
Figure 8:
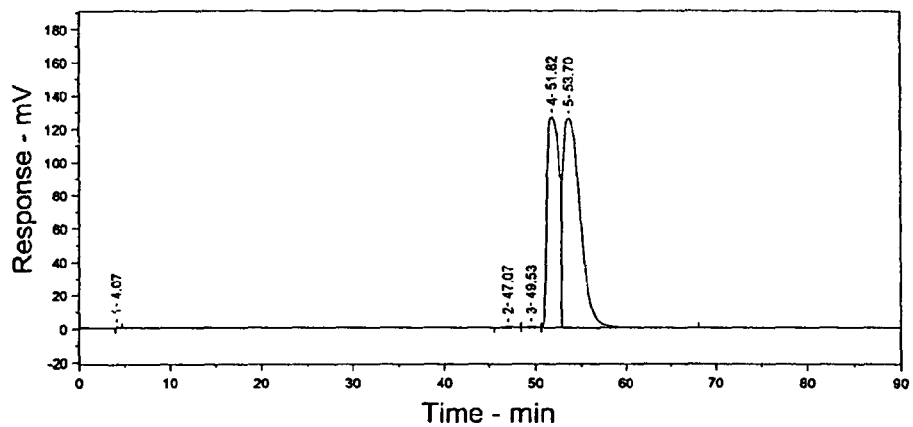
FIG. 8 illustrates a chromatogram of Evaluation Sample 1 in Evaluation 2 of Example 3.
Figure 9:
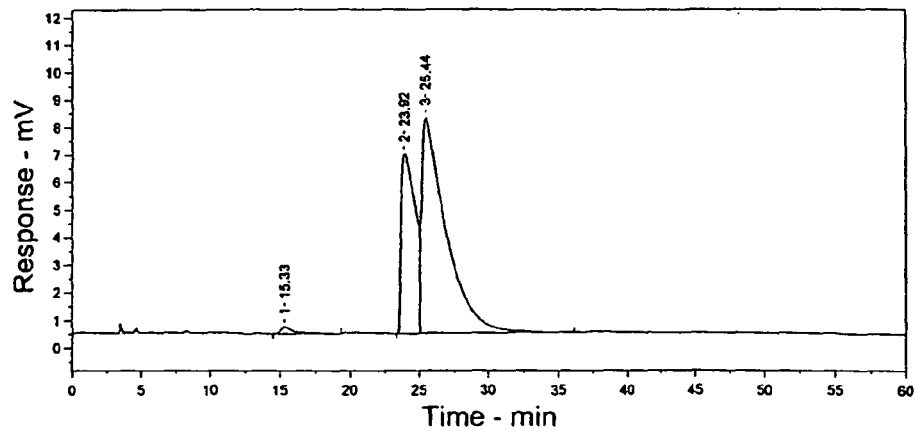
FIG. 9 illustrates a chromatogram of Evaluation Sample 2 in Evaluation 2 of Example 3.
Figure 10:
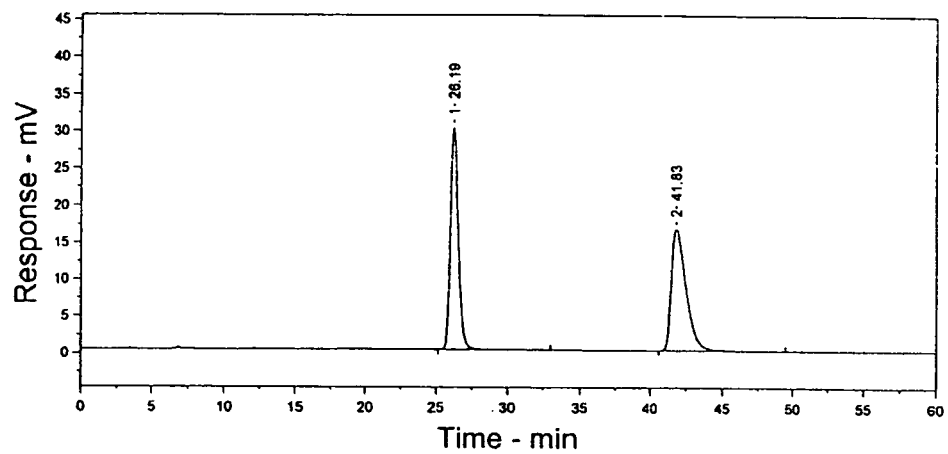
FIG. 10 illustrates a chromatogram of Evaluation Sample 3 in Evaluation 2 of Example 3.
Figure 11:
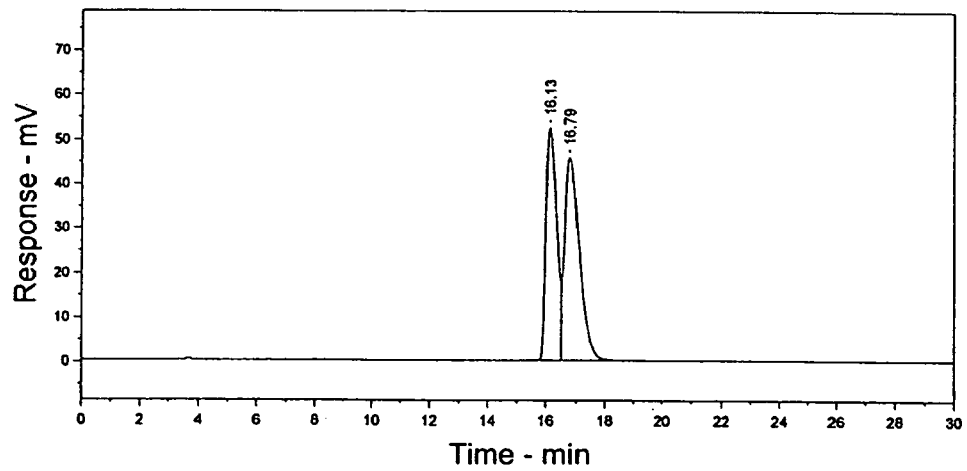
FIG. 11 illustrates a chromatogram of Evaluation Sample 4 in Evaluation 2 of Example 3.
Figure 12:
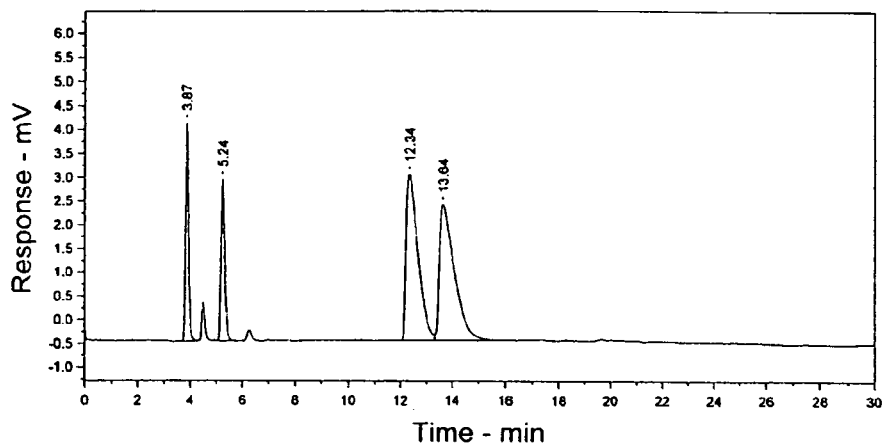
FIG. 12 illustrates a chromatogram of Evaluation Sample 5 in Evaluation 2 of Example 3.
Figure 13:
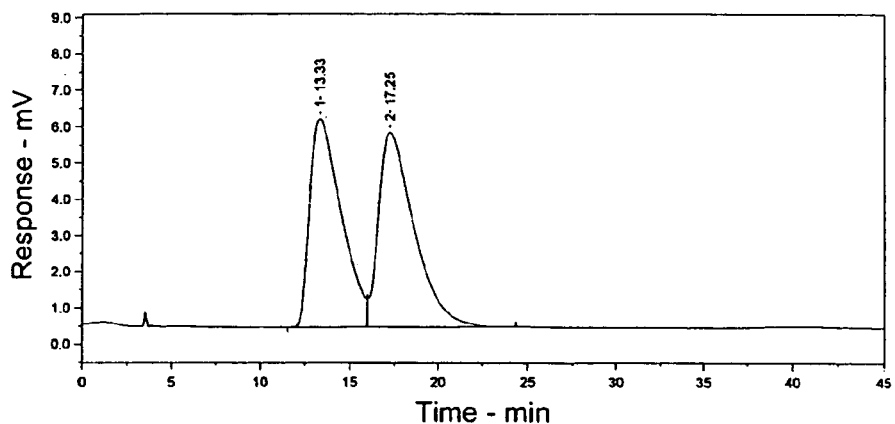
FIG. 13 illustrates a chromatogram of Evaluation Sample 6 in Evaluation 2 of Example 3.
Figure 14:
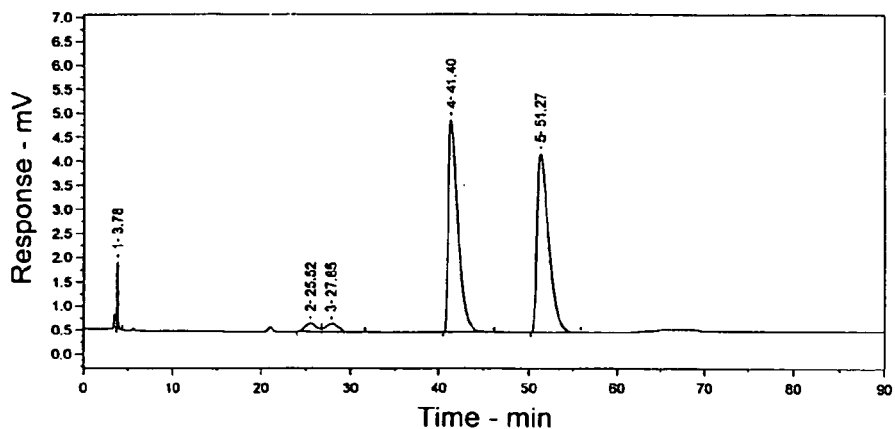
FIG. 14 illustrates a chromatogram of Evaluation Sample 8 in Evaluation 2 of Example 3.

An optical-isomer separating agent for chromatography of the present invention (hereinafter referred to as "separating agent") is obtained by causing a carrier to support a compound represented by the following general formula (1) by chemical bonding.

[Chem 9]

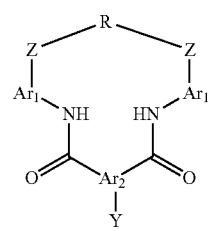

(1)

R represents an organic group having an asymmetric structure having 2 to 30 carbon atoms. The asymmetric structure may be a structure based on the entirety of the group like an axially asymmetric structure, or may be a structure based on an asymmetric carbon in the group. Examples of R include groups represented by the following general formulae (2), (3), and (4), and the following structural formulae (5) and (6).

[Chem 10]

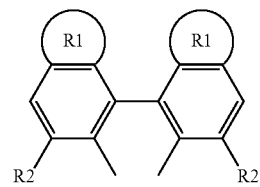

(2)

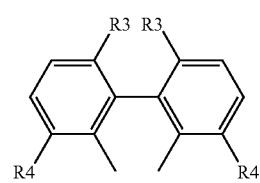

(3)

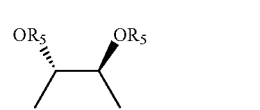

(4)

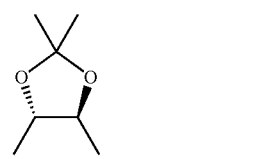

(5)

-continued

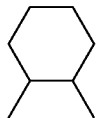
(6)

The R1 rings each independently represent an aromatic ring, an aliphatic ring, or no ring. A group representing the aromatic ring is, for example, a group that forms a fused ring formed of 2 to 4 benzene rings together with the benzene ring to which each R1 ring is bonded, and examples of the group include —$C_4H_4$—, —$C_8H_6$—, and —$C_{12}H_8$—. A group representing the aliphatic ring is, for example, an alkylene having 4 to 8 carbon atoms, and the resultant compound is, for example, a cyclic aliphatic compound part of which may be unsaturated. A group representing the above-mentioned no ring is, for example, a hydrogen atom. In addition, R2's each independently represent a hydrogen atom, a linear or branched alkyl group having 1 to 5 carbon atoms, an aromatic group, an ester group, or a halogen atom.

R3's each independently represent a hydrogen atom, a linear or branched alkyl group having 1 to 5 carbon atoms, a nitro group, an ester group, an aromatic group, or a halogen atom, and R4's each independently represent a hydrogen atom, a linear or branched alkyl group having 1 to 5 carbon atoms, an aromatic group, an ester group, or a halogen atom.

R5's each independently represent a hydrogen atom, a linear or branched alkyl group having 1 to 5 carbon atoms, an aromatic group, or an ester group.

Examples of the ester group include monovalent groups each including a structure produced by condensation between an organic acid containing a nitrogen atom, an oxygen atom, or a sulfur atom and an alcohol having 1 to 6 carbon atoms such as a methoxycarbonyl group and a tert-butyloxycarbonyl group. In addition, examples of the aromatic group include monovalent groups each including an aromatic ring having 6 to 14 carbon atoms such as a phenyl group, a naphthyl group, a phenanthrenyl group, and a biphenyl group.

R is preferably a group represented by the following structural formula (7) from the following viewpoint. That is, the group brings together moderate rigidity and flexibility based on its axially asymmetric structure. The absolute configuration of the group represented by the general formula (7) may be (R) or (S). Further, the group represented by the general formula (7) may have a substituent at each of 3- and 3'-positions from the viewpoints of the adjustment of the angle of the axial structure and the adjustment of the asymmetry recognition ability.

[Chem 11]

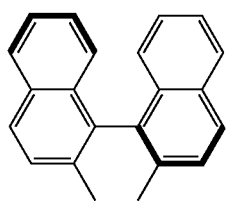
(7)

Ar1's each independently represent a divalent group having hydrogen-bond accepting property or an aromatic group which has 3 to 10 carbon atoms and which may have hydrogen-bond accepting property. Ar1 free of the hydrogen-bond accepting property is, for example, a divalent group including a benzene ring such as a phenylene. Ar1 having the hydrogen-bond accepting property is, for example, a group containing any one of nitrogen, oxygen, sulfur, phosphorus, and a halogen each having a relatively high electronegativity and exerting the hydrogen-bond accepting property, and examples of the group include a keto group and divalent groups each including the structure of each of pyridine, pyrimidine, triazine, furan, thiophene, tetrahydropyran, thiopyran, and quinoline. The number of hydrogen-bond acceptor sites such as the atoms described above in each Ar1 may be one or two or more, and the sites may be identical to or different from each other. In addition, each Ar1 may further have one or more hydrogen-bond donor sites such as an amino group and a hydroxyl group.

The size of the ring in the general formula (1) can be changed depending on the size of each Ar1, and the hydrogen bond property of the ring in the general formula (1) can be changed depending on the positions and numbers of hydrogen-bond acceptor sites and hydrogen-bond donor sites of Ar1's. Accordingly, the adjustment of separating performance can be expected from the structure of each Ar1. Ar1's are preferably such that: the hydrogen-bond acceptor sites such as the atoms described above are placed so as to face the inside of the ring in the general formula (1); and, a carbon atom adjacent to a carbon atom to which an atom serving as the hydrogen-bond acceptor site or a group serving as the hydrogen-bond acceptor site is bonded is preferably bonded to an amide group or Z in the general formula (1); from the viewpoint of the formation of a hydrogen bond between a compound to be separated clathrated with the ring and each of the hydrogen-bond acceptor sites.

Ar2 represents an aromatic or heterocyclic group having 3 to 14, or preferably 3 to 10, carbon atoms. Ar2 may have one or both of a hydrogen-bond donor site and a hydrogen-bond acceptor site from the same viewpoint as that of each Ar1. For example, Ar2 may contain any one of nitrogen, oxygen, sulfur, phosphorus, and a halogen each having a relatively high electronegativity and each exerting the hydrogen-bond accepting property as in the case of each Ar1. Examples of such Ar2 include trivalent groups each including a benzene ring, a naphthalene ring, an anthracene ring, a pyridine ring, a pyrrole ring, a thiophene ring, or a furan ring.

Ar1's are each preferably a group represented by the following structural formula (8), and Ar2 is preferably a group represented by the following structural formula (9).

[Chem 12]

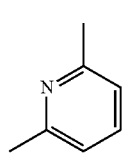
(8)

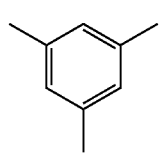
(9)

Z's each independently represent a single bond or a divalent group. Z's may each include one or both of a hydrogen-bond donor site and a hydrogen-bond acceptor site. In addition, the size of the ring in the general formula (1) can be changed depending on the number of atoms of which the linear site of each Z is constituted, and hence the adjustment of the separating performance can be expected from the structure of each Z. The number of atoms of which the linear site of each Z is constituted is preferably 1 to 8 or more preferably 2 to 6. It should be noted that the hydrogen-bond donor site which each Z may include is, for example, an amino group, an amide group, a carbamate group, a hydroxyl group, a group having a piperidine structure, a group having a pyrrolidine structure, a group having an aziridine structure, or a group having a pyrrole structure. The hydrogen-bond acceptor site which each Z may include is, for example, any one of the hydrogen-bond acceptor sites of Ar1's.

Examples of the divalent group include divalent organic groups each containing at least one of oxygen, nitrogen, and sulfur. The divalent group may be the very heteroatom such as oxygen or sulfur, or may contain a divalent hydrocarbon group. An arbitrary hydrogen atom of the divalent hydrocarbon group may be substituted with a halogen atom such as fluorine. Examples of such Z include groups represented by the following structural formulae (10) to (15) and groups each obtained by substituting arbitrary hydrogen of an alkylene group in each of the following structural formulae (10) to (15) with a halogen atom such as fluorine.

[Chem 13]

—O—$CH_2$—    (10)

—O—$CH_2$—CO—NH—    (11)

—O—CO—NH—    (12)

—$CH_2$—CO—NH—    (13)

—$CH_2$—NH—CO—    (14)

—S—$CH_2$—CO—NH—    (15)

Y represents a group which can chemically bond to the carrier. Y may be a group directly bonded to the carrier, or may be a group bonded to the carrier through any other group. Y is preferably a group which covalently bonds to the carrier from the viewpoint of an improvement in durability of the separating agent of the present invention. Y can be determined depending on the kind of the carrier. For example, when the carrier is a silica gel, a group that reacts with a silanol group to form a siloxane bond is used as Y, and examples of the group include groups represented by the following general formulae (16) to (20). It should be noted that, in the following general formulae (16) to (20), n represents an integer of 1 to 20. Alternatively, part of Y may be bonded to the carrier such as silica in advance and then, the part of Y and part of Y bonded to Ar2 may be bonded to each other by a chemical bond such as an amide bond. Further, Y may be a group obtained by independently substituting an ethoxy in each of the general formulae (16) to (20) with a lower alkoxy group having about 1 to 4 carbon atoms such as a methoxy. Further, Y may be a group obtained by independently substituting one or two of the three alkoxy groups in each of the general formulae (16) to (20) with a lower alkyl group having about 1 to 4 carbon atoms such as a methyl group.

[Chem 14]

—CO—NH—$(CH_2)_n$—$Si(OEt)_3$    (16)

—S—$(CH_2)_3$—O—$(CH_2)_n$—$Si(OEt)_3$    (17)

—NH—$CH_2$—CH(OH)—$(CH_2)_n$—$Si(OEt)_3$    (18)

—CH=N—$(CH_2)_n$—$Si(OEt)_3$    (19)

—O—$CH_2$—CO—NH—$(CH_2)_n$—$Si(OEt)_3$    (20)

Alternatively, Y may be a group bonded to an amino group, mercapto group, or glycidyl group bonded to the carrier like the carrier with its surface modified. Examples of such Y include a hydroxyl group and groups represented by the following formulae (31) to (38). In those formulae, n represents an integer of 1 to 20 and X represents a halogen atom such as chlorine or bromine.

[Chem 15]

—O—$(CH_2)_n$—COOH    (31)

—$CO_2$—COOH    (32)

—O—$(CH_2)_n$—X    (33)

—O—$(CH_2)_n$—$NH_2$    (34)

—O—$(CH_2)_n$—CH=$CH_2$    (35)

—O—$(CH_2)_n$—$CO_2$—Et    (36)

—$CO_2$—$(CH_2)_n$—COX    (37)

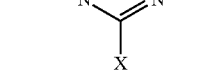    (38)

A carrier typically used in the HPLC can be used as the carrier. Examples of such carrier include a porous organic carrier and a porous inorganic carrier. Examples of the porous organic carrier include polystyrene, polyacrylamide, and polyacrylate. Examples of the porous inorganic carrier include a silica gel, alumina, magnesia, glass, kaolin, titanium oxide, a silicate, and hydroxyapatite. The silica gel is preferably used as the carrier.

The content of a component derived from the compound represented by the general formula (1) in the separating agent of the present invention is preferably 1 to 99 mass % or more preferably 5 to 50 mass % with respect to the entirety of the separating agent from the viewpoint of sufficient exertion of asymmetry recognition performance by the compound. The content can be measured by utilizing an ordinary analysis technique such as elemental analysis or IR.

The separating agent of the present invention can be produced via the following synthesis route.

[Chem 16]

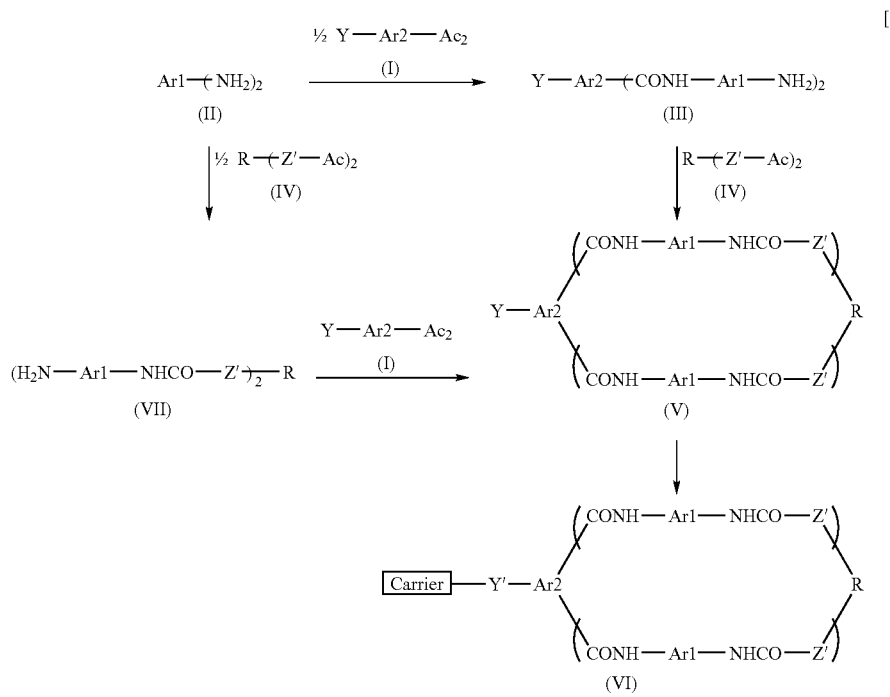

That is, the separating agent of the present invention can be produced through the process A, including: causing two equivalents of a diamine (II) represented by the general formula (II) and one equivalent of an acid compound (I) represented by the general formula (I) to react with each other to obtain a diamine (III) represented by the general formula (III); causing equal equivalents of the diamine (III) and the acid compound (IV) represented by the general formula (IV) to react with each other to obtain a cyclic amide compound (V) represented by the general formula (V); and causing Y of the cyclic amide compound (V) and a carrier to react with each other directly or through a crosslinking group to obtain an optical-isomer separating agent for chromatography represented by the general formula (VI).

Alternatively, the separating agent of the present invention can be produced through the process B, including: causing two equivalents of the diamine (II) and one equivalent of the acid compound (IV) to react with each other to obtain the diamine (VII); causing equal equivalents of the diamine (VII) and the acid compound (I) to react with each other to obtain the cyclic amide compound (V); and bonding Y of the cyclic amide compound (V) and the carrier to react with each other directly or through the crosslinking group to obtain the optical-isomer separating agent for chromatography represented by the general formula (VI).

Ar1's, Ar2's, R's, and Y's in the general formulae (I) to (VII) are identical to Ar1's, Ar2, R, and Y in the general formula (1) in the separating agent of the present invention described above, respectively.

In the general formula (VI), Y' represents a group chemically bonded to the carrier, and represents such a group that Y in the general formula (V) is chemically bonded to the carrier or such a group that Y in the general formula (V) is chemically bonded to the carrier through the crosslinking group.

In each of the processes A and B of the present invention, a group containing a hydroxyl group, an alkoxy group having 1 to 4 carbon atoms, a carboxyl group, a mercapto group, an amino group, an amide group, an ester group, or an aldehyde group can be preferably used as each of Y and Y'.

Z's in the general formulae (I) to (VII) each independently represent a single bond or a divalent group, and "—Z'—CONH—" in each of the general formulae (V) to (VII) corresponds to each Z in the general formula (1). Examples of such Z's include —O—, —O—$CH_2$—, —$CH_2$—, —S—$CH_2$—, and a group obtained by incorporating one or both of the hydrogen-bond donor site and the hydrogen-bond acceptor site into each of those groups.

The carrier in the separating agent of the present invention can be used as it is as the carrier, or can be used as the carrier after having been subjected to surface modification. The term "surface modification" refers to chemical bonding of a proper group to the surface of the carrier. In the case of, for example, a silica gel preferably used as the carrier, the term refers to chemical bonding of the proper group to a silanol group on the surface of the silica gel.

A group bonded to both Y and the carrier is used as the crosslinking group. The crosslinking group is preferably a divalent group having about 1 to 25 carbon atoms from the viewpoints of the strength of the crosslinking and the ease of handling in each of the processes A and B. The crosslinking group may be a group bonded to the carrier before being bonded to Y, may be a group bonded to Y in advance before being bonded to the carrier, or may be a group simultaneously bonded to both the carrier and Y. From such a viewpoint that the ease with which the carrier and the cyclic amide compound (V) are bonded to each other is raised, the group is preferably a group bonded to the carrier before being bonded to Y. That is, the silica gel as the carrier is preferably subjected to surface modification with a group serving as the crosslinking group.

Examples of such group serving as the crosslinking group that modifies the surface of the silica gel include groups represented by the following general formulae (21) to (25). It should be noted that, in the general formulae (21) to (25), m and n each represent an integer of 1 to 20.

[Chem 17]

 (21)

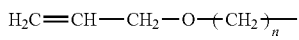 (22)

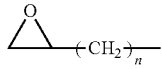 (23)

 (24)

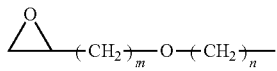 (25)

In the general formulae (I) to (VII), Ac represents a carboxyl group or —COCl. A reaction between each of the acid compounds (I) and (IV), and the diamine can be performed by using a condensation agent such as dicyclohexylcarbodiimide in combination when Ac is a carboxyl group, or can be performed by using the compounds as they are when Ac is an acid chloride (—COCl).

For example, the reaction between the diamine (II), (III), or (VII) and the acid chloride (I) or (IV) in each of the productions A and B can be performed under such ordinary conditions that an amide group is produced from the acid chloride and an amino group. The reaction is performed under conditions of, for example, −78 to 115° C. and 0.1 to 50 hours. In addition, the resultant product, which may be used as it is in any subsequent reaction, can be purified by an ordinary purification technique such as recrystallization or column chromatography, and a purified product obtained by such purification may be used in any subsequent reaction.

In addition, the usage of the cyclic amide compound (V) upon bonding between Y and the carrier is preferably 5 to 500 mass % or more preferably 10 to 100 mass % with respect to the carrier from such a viewpoint that the compound is bonded to the carrier in an amount that suffices for the separation of optical isomers with the resultant separating agent.

Further, the usage of the crosslinking group upon bonding between Y and the carrier is preferably 5 to 500 mass % or more preferably 10 to 100 mass % with respect to the carrier from such a viewpoint that the cyclic amide compound (V) is bonded to the carrier in an amount that suffices for the separation of optical isomers with the resultant separating agent.

In addition, conditions under which the cyclic amide compound (V) and the carrier are bonded to each other in each of the productions A and B can be appropriately determined depending on Y, the crosslinking agent, and the carrier. For example, when the carrier is a silica gel and the crosslinking agent is a trialkoxysilane-based compound, conditions for a reaction between the carrier and the crosslinking agent are, for example, such conditions that the reaction is performed in an aprotic solvent such as toluene, benzene, or tetrahydrofuran under heating at room temperature or higher while an amine compound may be caused to coexist as a promoter, and further, an alcohol as a by-product may be removed.

In addition, a reaction between the crosslinking agent and Y can be performed under conditions corresponding to their structures. For example, the addition reaction of a thiol group to a carbon-carbon double bond can be performed in a hydrocarbon solvent such as toluene in the presence of a radical initiator under a temperature condition of 100° C. or lower. A dehydration condensation reaction between an acid and an amine or the like can be performed in the coexistence of a dehydration condensation agent such as dicyclohexylcarbodiimide with an aprotic solvent under a condition ranging from −78° C. to 150° C. Further, a reductive amination reaction can be performed in the presence of a small amount of an acid by reductively using sodium cyanoborohydride or a borane complex with an aprotic solvent under a condition ranging from −78° C. to 150° C. Even a reaction involving the use of a glycidyl group can be performed with an aprotic solvent by using a small amount of a tertiary amine compound or the like as a promoter under a condition ranging from −78° C. to 150° C.

The separating agent (VI) obtained by direct bonding between Y and the carrier or by bonding between Y and the carrier through the crosslinking group provided by the crosslinking agent can be used as the separating agent after having been washed with a proper solvent.

The separating agent of the present invention can be used in known separation and production techniques for optical isomers each involving the use of a column obtained by loading the separating agent into a column tube by an ordinary method involving supplying slurry of the separating agent and a proper solvent to the column tube to load the separating agent. Examples of such known separation and production techniques for optical isomers include high performance liquid chromatography, supercritical fluid chromatography, and simulated moving bed chromatography. The supercritical fluid chromatography is, for example, supercritical fluid chromatography disclosed in JP-A-2005-326180 in which a mixed fluid of a supercritical fluid and a solvent is used as a moving phase, and the supercritical fluid can be recovered from the moving phase that has passed through a column and can be recycled. The simulated moving bed chromatography is, for example, simulated moving bed chromatography disclosed in JP-A-2006-133160 in which a solvent can be recovered from a moving phase discharged from a column and can be recycled.

The separating agent of the present invention is obtained by chemically bonding the ring structure including R as an asymmetry recognition site and an amide group as a hydrogen-bond donor site to the carrier in a state where the ring structure is maintained, and can separate optical isomers when used in chromatography. This is probably attributable to the fact that, under such conditions for chromatography that the rough and dense portions of the distribution of optical isomers to be separated are formed, the ring structure has such moderate affinity as to adsorb and desorb the optical isomers.

In addition, the separating agent of the present invention is obtained by chemically bonding the ring structure to the carrier, and hence the molecules of the ring structure having optical-isomer separating performance are independently present on the carrier. As a result, even when the ring structure is placed on the carrier at a high density, the optical-isomer separating performance of each molecule of the ring structure is maintained, and hence the exertion of the optical-isomer separating performance corresponding to the amount of the ring structure can be expected.

In addition, in the separating agent of the present invention, the size of the ring structure, and the positions of the hydrogen-bond donor sites and the hydrogen-bond acceptor sites in the ring structure can be adjusted depending on the structures and sizes of Ar1's, Ar2, and Z's of which the ring structure is constituted. Accordingly, the formation of a separating agent having high separating performance for specific optical isomers can be expected from the design of a ring structure corresponding to optical isomers to be separated.

In addition, in the separating agent of the present invention, the ring structure and the carrier are bonded to each other through Y. Accordingly, the ring structure can be bonded to the carrier while the optical-isomer separating performance of the ring structure is sufficiently maintained.

EXAMPLES

The present invention is described in detail by way of examples. However, the present invention is not limited to those examples. It should be noted that, in the following examples, a form in which a chiral stationary phase is bonded to a silica gel with three silanol groups and a form in which a chiral stationary phase is bonded to a silica gel with a single bond are shown. The foregoing means that the chiral stationary phases of the examples are each bonded to the silica gel through one to three silanol groups.

Example 1

Preparation of Chiral Stationary Phase CSP-1

Chiral Stationary Phase CSP-1 was prepared via the following synthesis route.

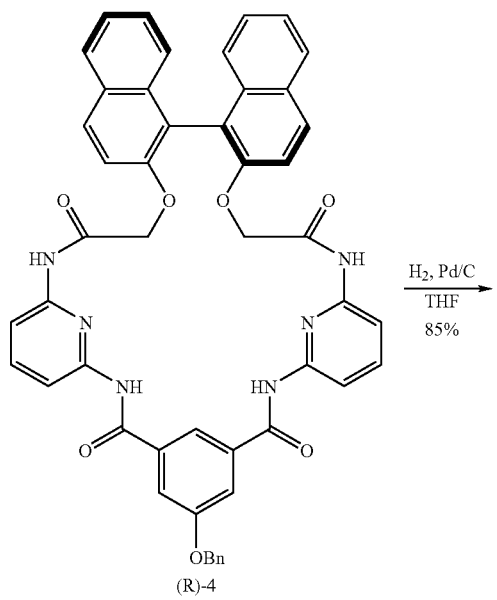

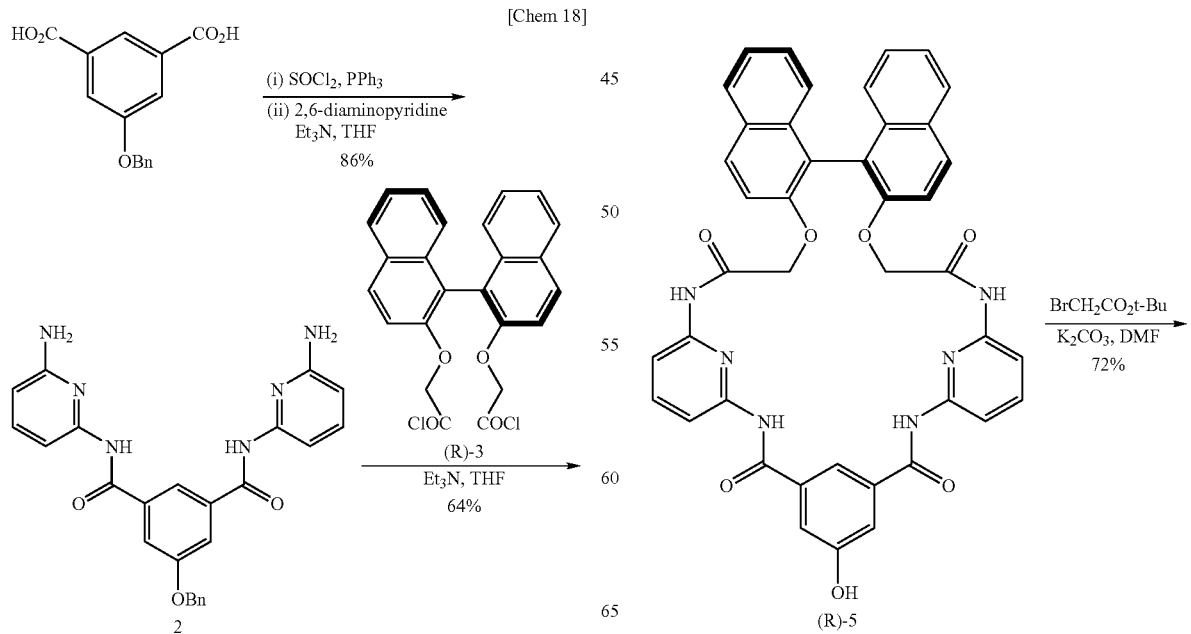

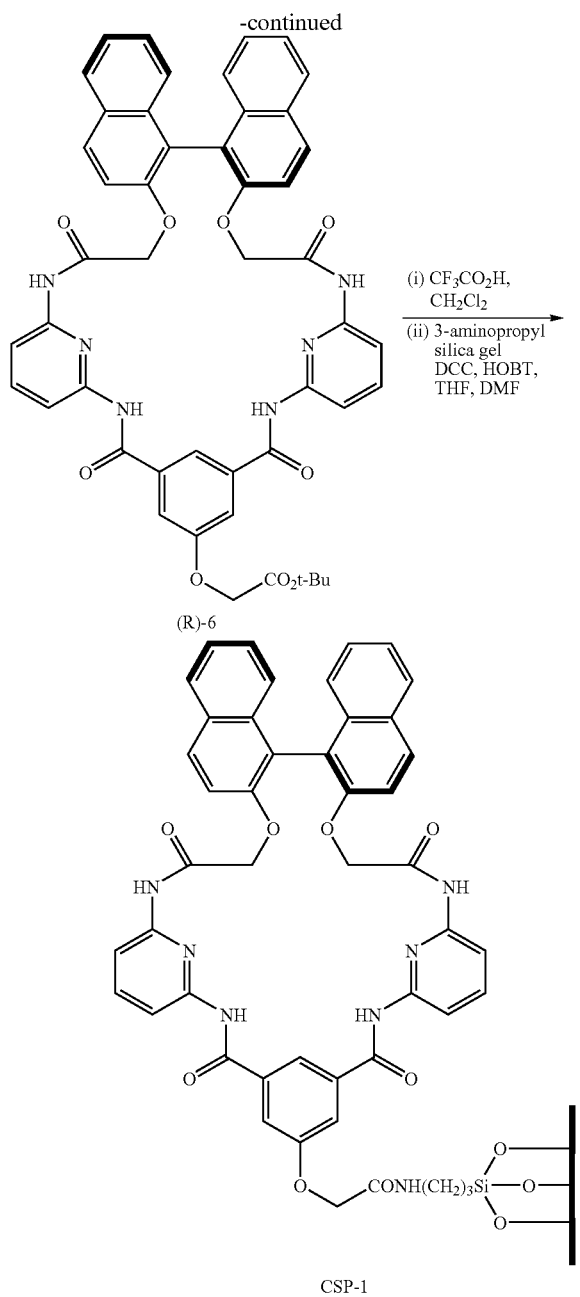

Synthesis of N,N'-Bis(6-amino-2-pyridinyl)-5-benzyloxy-1,3-benzenedicarboxamide (Compound 2)

First, 5-benzyloxyisophthalic acid was synthesized in accordance with F. Diederich, G. Schurmann, I. Chao, Designed water-soluble macrocyclic esterases: from nonproductive to productive binding. J. Org. Chem., 53(12), 2744-2757 (1988).

In accordance with M. Berger, F. P. Schmidtchen, Zwitterionic guanidinium compounds serve as electroneutral anion hosts. J. Am. Chem. Soc., 121(43), 9986-9993 (1999), 5-benzyloxyisophthalic acid (2.72 g, 9.99 mmol) and triphenylphosphine (29 mg, 0.11 mmol) were added to thionyl chloride (45 mL), and the mixture was refluxed under heat for 40 minutes. Excessive thionyl chloride was removed by distillation. As a result, an acid chloride of 5-benzyloxyisophthalic acid as a white solid was obtained (2.92 g, 95% yield).

A solution (94 mL) of the acid chloride of 5-benzyloxyisophthalic acid (2.91 g, 9.40 mmol) in dry tetrahydrofuran was dropped to a solution (236 mL) of 2,6-diaminopyridine (10.3 g, 94.0 mmol) and triethylamine (2.6 mL, 19 mmol) in dry tetrahydrofuran at room temperature under a nitrogen atmosphere over 1 hour. The resultant mixed liquid was stirred for 5.5 hours, and then the solvent was removed from the mixed liquid by distillation under reduced pressure.

In order that excessive 2,6-diaminopyridine and triethylamine hydrochloride might be removed, the residue was washed with water (1 L), filtrated, and washed with water (1 L) again. As a result, a solid product was obtained. The product was purified by silica gel column chromatography (hexane/tetrahydrofuran (hexane:tetrahydrofuran (volume ratio)=1:2)). The resultant purified product was recrystallized from tetrahydrofuran/hexane. As a result, Compound 2 as a tan crystal was obtained (3.83 g, 90% yield (86% yield in two stages)). Spectrum data on Compound 2 thus obtained is shown below.

Spectrum Data mp 180° C.

$^1$H NMR ($d_6$-acetone, 600 MHz) 5.32 (s, 2H), 5.34 (br s, 4H), 6.34 (dd, J=0.8, 7.9 Hz, 2H), 7.34 (tt, J=1.6, 7.4 Hz, 1H), 7.42 (t, J=7.4 Hz, 2H), 7.45 (t, J=7.9 Hz, 2H), 7.54-7.56 (m, 2H), 7.60 (dd, J=0.8, 7.9 Hz, 2H), 7.84 (d, J=1.7 Hz, 2H), 8.29 (t, J=1.7 Hz, 1H), 9.36 (s, 2H)

$^{13}$C NMR ($d_6$-acetone, 150 MHz) 70.9, 103.0, 104.9, 118.3, 119.3, 128.5, 128.8, 129.3, 137.4, 137.8, 140.0, 151.4, 159.4, 160.1, 165.2

IR (KBr) 3364, 3213, 3063, 1678, 1620, 1543, 1458, 1300, 1246, 1130, 1045, 791 cm$^{-1}$

HRMS (ESI-IT-TOF, MeCN) calcd for $C_{25}H_{23}N_6O_3$ 455.1826. found 455.1830 (M+H)

Synthesis of Chiral Macrocycle (R)-4 (Compound (R)-4)

Acid Chloride (R)-3 was synthesized in accordance with T. Ema, D. Tanida, T. Sakai, Versatile and practical chiral shift reagent with hydrogen-bond donor/acceptor sites in a macrocyclic cavity. Org. Lett., 8(17), 3773-3775 (2006). A solution (180 mL) of Acid Chloride (R)-3 (785 mg, 1.79 mmol) in dry tetrahydrofuran, Compound 2 (654 mg, 1.44 mmol), and a solution (180 mL) of triethylamine (0.4 mL, 2.9 mmol) in dry tetrahydrofuran were dropped to dry tetrahydrofuran (120 mL) at room temperature at the same rate over 3.5 hours. The resultant mixed liquid was stirred for an additional 10 hours, and then a volatile substance was removed from the mixed liquid with an evaporator. The resultant solid residue was dissolved in methylene chloride, and then the solution was washed with saturated baking soda water (40 mL) and dried with sodium sulfate. After that, the dried product was concentrated under reduced pressure. As a result, a solid product was obtained. The product was purified by silica gel column chromatography (methylene chloride/tetrahydrofuran (methylene chloride:tetrahydrofuran (volume ratio)=20:1)). The resultant purified product was recrystallized from methylene chloride. As a result, Compound (R)-4 as a white crystal was obtained (753 mg, 64% yield). Spectrum data on Compound (R)-4 thus obtained is shown below.

Spectrum Data mp 206° C.

$[\alpha]^{30}_D$+220 (c 1.00, CHCl$_3$)

$^1$H NMR (CDCl$_3$, 600 MHz) 4.27 (d, J=15.9 Hz, 2H), 4.51 (d, J=15.9 Hz, 2H), 5.20 (s, 2H), 7.29 (d, J=8.1 Hz, 2H), 7.33-7.49 (m, 11H), 7.78 (t, J=8.3 Hz, 2H), 7.909-7.911 (m, 3H), 7.93 (d, J=8.1 Hz, 2H), 7.96 (d, J=8.3 Hz, 2H), 8.04 (d, J=8.4 Hz, 2H), 8.15 (d, J=8.3 Hz, 2H), 8.70 (s, 2H), 8.86 (s, 2H)

$^{13}$C NMR (CDCl$_3$, 150 MHz) 70.5, 73.0, 109.9, 110.2, 115.1, 119.0, 119.2, 123.0, 125.2, 125.6, 127.3, 127.5, 128.3, 128.4, 128.7, 130.9, 131.1, 133.4, 135.2, 135.8, 141.3, 148.5, 149.5, 154.1, 160.3, 163.3, 167.4

IR (KBr) 3387, 3055, 1697, 1589, 1512, 1450, 1312, 1242, 1211, 1150, 1049, 802 cm$^{-1}$

HRMS (ESI-IT-TOF, MeCN) calcd for C$_{49}$H$_{36}$N$_6$O$_7$Na 843.2538. found 843.2550 (M+Na)

Synthesis of Chiral Macrocycle (R)-5 (Compound (R)-5)

First, 10% palladium carbon (203 mg) was added to a solution (42 mL) of Compound (R)-4 (910 mg, 1.11 mmol) in dry tetrahydrofuran, and then the mixture was stirred at room temperature under a hydrogen atmosphere for 22 hours. The reaction mixture was filtrated with celite, and then the solvent was removed from the resultant filtrate by distillation. As a result, a solid product was obtained. The resultant product was recrystallized from acetone. As a result, Compound (R)-5 as a white solid was obtained (687 mg, 85% yield). Spectrum data on Compound (R)-5 thus obtained is shown below.

Spectrum Data
mp 233° C. (dec)
[α]$^{29}_D$+262 (c 1.01, tetrahydrofuran)
$^1$H NMR (d$_6$-acetone, 600 MHz, 40° C.) 4.40 (d, J=15.6 Hz, 2H), 4.80 (d, J=15.6 Hz, 2H), 7.44-7.51 (m, 6H), 7.72 (d, J=1.8 Hz, 2H), 7.76 (d, J=9.0 Hz, 2H), 7.80 (d, J=8.0 Hz, 2H), 7.83 (t, J=8.0 Hz, 2H), 8.02 (d, J=7.5 Hz, 2H), 8.14 (dd, J=1.2, 8.0 Hz, 2H), 8.17 (d, J=9.0 Hz, 2H), 8.45 (s, 1H), 8.62 (s, 2H), 9.09 (s, 1H), 9.65 (s, 2H)

$^{13}$C NMR (d$_6$-acetone, 150 MHz) 73.5, 109.6, 110.0, 117.5, 119.7, 120.0, 123.2, 126.1, 126.4, 127.8, 129.2, 131.6, 131.8, 134.5, 136.4, 141.7, 149.9, 151.5, 155.3, 159.4, 164.9, 167.8

IR (KBr) 3379, 3063, 1697, 1589, 1528, 1450, 1319, 1242, 1211, 1157, 1065, 802 cm$^{-1}$

HRMS (ESI-IT-TOF, MeCN) calcd for C$_{42}$H$_{30}$N$_6$O$_7$Na 753.2068. found 753.2065 (M+Na)

Synthesis of Chiral Macrocycle (R)-6 (Compound (R)-6)

A dry dimethylformamide mixed solution (3.3 mL) containing Compound (R)-5 (698 mg, 0.955 mmol), bromoacetic acid t-butyl ester (0.17 mL, 1.2 mmol), and potassium carbonate (147 mg, 1.06 mmol) was stirred under a nitrogen atmosphere at 80° C. for 17.5 hours. The resultant reaction mixture was filtrated, and then the solvent was removed from the resultant filtrate by distillation. As a result, a solid product was obtained. The resultant product was purified by silica gel column chromatography (methylene chloride/tetrahydrofuran (methylene chloride:tetrahydrofuran (volume ratio)=30:1)). As a result, Compound (R)-6 as a white solid was obtained (578 mg, 72% yield). Spectrum data on Compound (R)-6 thus obtained is shown below.

Spectrum Data
mp 244° C. (dec)
[α]$^{25}_D$+211 (c 1.01, CHCl$_3$)
$^1$H NMR (CDCl$_3$, 600 MHz) 1.50 (s, 9H), 4.28 (d, J=16.2 Hz, 2H), 4.52 (d, J=16.2 Hz, 2H), 4.66 (s, 2H), 7.29 (d, J=8.1 Hz, 2H), 7.38 (dt, J=1.3, 8.1 Hz, 2H), 7.44 (d, J=9.3 Hz, 2H), 7.47 (dt, J=1.3, 8.1 Hz, 2H), 7.79 (t, J=7.8 Hz, 2H), 7.82 (s, 2H), 7.90 (br s, 1H), 7.93 (d, J=8.1 Hz, 2H), 7.96 (d, J=7.8 Hz, 2H), 8.02 (d, J=9.3 Hz, 2H), 8.14 (d, J=7.8 Hz, 2H), 8.76 (s, 2H)

$^{13}$C NMR (CDCl$_3$, 150 MHz) 28.0, 65.7, 72.9, 82.9, 109.9, 110.2, 115.8, 118.7, 119.1, 122.9, 125.2, 125.5, 127.2, 128.4, 130.9, 131.0, 133.4, 135.2, 141.3, 148.4, 149.4, 154.1, 159.5, 163.0, 167.2, 167.4

IR (KBr) 3391, 3059, 1686, 1585, 1520, 1454, 1315, 1242, 1157, 1080, 802 cm$^{-1}$

HRMS (ESI-IT-TOF, MeCN) calcd for C$_{48}$H$_{40}$N$_6$O$_9$Na 867.2749. found 867.2741 (M+Na)

[Preparation of Chiral Stationary Phase (CSP-1)]

Compound (R)-6 (1.04 g, 1.23 mmol) was dissolved in a mixed solution of trifluoroacetic acid (1.9 mL, 25 mmol) and dry methylene chloride (0.6 mL), and then the solution was stirred at room temperature under a nitrogen atmosphere for 18 hours. The solvent was removed from the resultant reaction liquid by distillation, and then the remainder was dried in a vacuum. As a result, a carboxylic acid of Compound (R)-6 in which the t-butyl group of Compound (R)-6 was substituted with hydrogen was obtained. A mixed solution of dry dimethylformamide (12 mL) and dry tetrahydrofuran (5.4 mL) in which the carboxylic acid of Compound (R)-6 (1.56 g, 1.97 mmol) was dissolved, 1,3-dicyclohexylcarbodiimide (DCC, 621 mg, 3.01 mmol), and 1-hydroxybenzotriazole (HOBT, 411 mg, 3.04 mmol) were added to an aminopropyl silica gel (4.11 g) left standing to cool under nitrogen after having been dried in a vacuum at 110° C. for 4.5 hours. After the resultant slurry had been stirred with a mechanical stirrer at room temperature for 48 hours, DCC (619 mg, 3.00 mmol), HOBT (411 mg, 3.04 mmol), and acetic acid (0.35 mL, 6.1 mmol) were added to the slurry, and then the mixture was stirred for an additional 48 hours. A silica gel obtained by filtrating the resultant slurry was washed with tetrahydrofuran, dimethylformamide, ethanol, and hot ethanol in the stated order, and was then dried in a vacuum. As a result, CSP-1 as a white powder was obtained.

It should be noted that a Wakosil 5NH2 (Wako Pure Chemical Industries, Ltd.) was used as the aminopropyl silica gel.

Example 2

Preparation of Chiral Stationary Phase CSP-2

Chiral Stationary Phase CSP-2 was prepared via the following synthesis route.

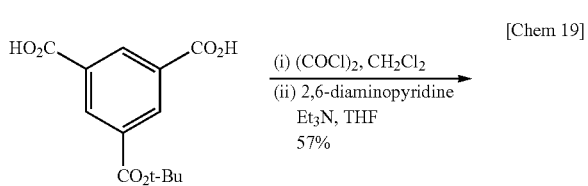

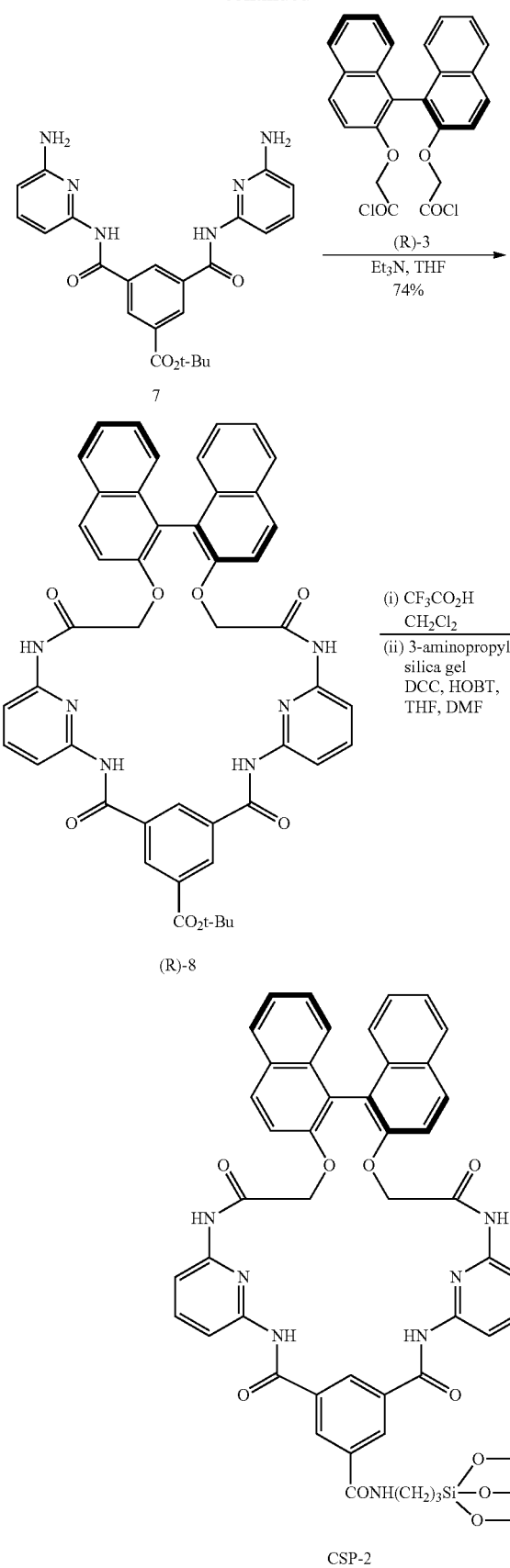

Synthesis of N,N'-Bis(6-amino-2-pyridinyl)-5-tert-butyloxycarbonyl-1,3-benzenedicarboxamide (Compound 7)

First, 5-tert-butyloxycarbonylisophthalic acid was synthesized in accordance with H. M. P. Chen, D. Katsis, S. H. Chen, Deterministic synthesis and optical properties of glassy chiral-nematic liquid crystals. Chem. Mater., 15(13), 2534-2542 (2003). Oxalyl chloride (2.0 mL, 23 mmol) and dimethylformamide (one drop) were added to a suspension (60 mL) of 5-tert-butyloxycarbonylisophthalic acid (1.60 g, 6.01 mmol) in dry methylene chloride, and then the mixture was stirred at room temperature for 5 hours. A volatile substance was removed from the resultant mixed liquid with an evaporator, and then the resultant solid was dried in a vacuum for 3 hours. The resultant acid chloride of 5-tert-butyloxycarbonylisophthalic acid was used without any further purification.

A solution (60 mL) of the acid chloride of 5-tert-butyloxycarbonylisophthalic acid (1.82 g, 6.01 mmol) in dry tetrahydrofuran was dropped to a solution (150 mL) of 2,6-diaminopyridine (6.55 g, 60.1 mmol) and triethylamine (1.65 mL, 11.9 mmol) in dry tetrahydrofuran at room temperature under a nitrogen atmosphere over 1 hour. The resultant mixed liquid was stirred for 10.5 hours, and then the solvent was removed from the mixed liquid by distillation under reduced pressure. In order that excessive 2,6-diaminopyridine and triethylamine hydrochloride might be removed, the residue was washed with water (1.5 L), filtrated, and washed with water (1.5 L) again. As a result, a solid product was obtained. The product was purified by silica gel column chromatography (hexane/tetrahydrofuran (hexane:tetrahydrofuran (volume ratio)=1:2)). The resultant purified product was recrystallized from tetrahydrofuran/hexane. As a result, Compound 7 as a tan crystal was obtained (1.55 g, 57% yield). Spectrum data on Compound 7 thus obtained is shown below.

Spectrum Data mp 138° C. (dec)

$^1$H NMR ($d_6$-acetone, 600 MHz) 1.64 (s, 9H), 5.35 (br s, 4H), 6.35 (dd, J=0.9, 7.9 Hz, 2H), 7.47 (t, J=7.9 Hz, 2H), 7.61 (d, J=7.9 Hz, 2H), 8.71 (d, J=1.5 Hz, 2H), 8.87 (t, J=1.5 Hz, 1H), 9.56 (s, 2H)

$^{13}$C NMR ($d_6$-acetone, 150 MHz) 28.2, 82.4, 103.0, 105.0, 130.7, 132.4, 133.8, 136.4, 140.0, 151.4, 159.5, 164.8, 164.9

IR (KBr) 3460, 3352, 3213, 3074, 1717, 1628, 1547, 1458, 1296, 1250, 1165, 795 cm$^{-1}$

HRMS (ESI-IT-TOF, MeCN) calcd for $C_{23}H25N_6O_4$ 449.1932. found 449.1922 (M+H)

Synthesis of Chiral Macrocycle (R)-8 (Compound (R)-8)

A solution (180 mL) of Acid Chloride (R)-3 (785 mg, 1.79 mmol) in dry tetrahydrofuran, and a solution (180 mL) of Compound 7 (647 mg, 1.44 mmol) and triethylamine (0.45 mL, 3.24 mmol) in dry tetrahydrofuran were dropped to dry tetrahydrofuran (120 mL) at room temperature at the same rate over 4.5 hours. The resultant mixed liquid was stirred for an additional 11 hours, and then a volatile substance was removed from the mixed liquid with an evaporator. The resultant solid residue was dissolved in methylene chloride, and then the resultant solution was washed with saturated saline (40 mL) and dried with sodium sulfate. After that, the dried product was concentrated under reduced pressure. As a result, a solid product was obtained. The resultant product was purified by silica gel column chromatography (methylene chloride/tetrahydrofuran (methylene chloride:tetrahydrofuran (volume ratio)=30:1)). As a result, Compound (R)-8 as a white solid was obtained (864 mg, 74% yield). Spectrum data on Compound 8 thus obtained is shown below.

Spectrum Data mp 266° C. (dec)

$[\alpha]^{22}_D$+182 (c 1.02, CHCl$_3$)

$^1$H NMR (CDCl$_3$, 600 MHz) 1.63 (s, 9H), 4.28 (d, J=16.2 Hz, 2H), 4.53 (d, J=16.2 Hz, 2H), 7.29 (d, J=8.0 Hz, 2H), 7.39 (dt, J=1.1, 8.0 Hz, 2H), 7.43 (d, J=9.0 Hz, 2H), 7.47 (dt, J=1.1, 8.0 Hz, 2H), 7.78 (t, J=8.0 Hz, 2H), 7.91-7.93 (m, 4H), 7.99 (d, J=9.0 Hz, 2H), 8.15 (d, J=8.0 Hz, 2H), 8.41 (s, 1H), 8.72 (s, 2H), 8.87 (d, J=1.2 Hz, 2H)

$^{13}$C NMR (CDCl$_3$, 150 MHz) 28.1, 72.7, 82.4, 110.0, 110.4, 118.9, 122.8, 125.1, 125.6, 126.7, 127.3, 128.4, 130.8, 131.0, 133.3, 133.4, 133.9, 134.5, 141.1, 148.2, 149.4, 153.9, 163.0, 163.7, 167.4

IR (KBr) 3395, 3055, 1701, 1585, 1508, 1454, 1292, 1246, 1157, 1080, 802, cm$^{-1}$

HRMS (ESI-IT-TOF, MeCN) calcd for C$_{47}$H$_{38}$N$_6$O$_8$Na 837.2643. found 837.2605 (M+Na)

[Preparation of Chiral Stationary Phase (CSP-2)]

Compound (R)-8 (542 mg, 0.665 mmol) was dissolved in a mixed solution of trifluoroacetic acid (1.1 mL, 14 mmol) and dry methylene chloride (0.5 mL), and then the solution was stirred at room temperature under a nitrogen atmosphere for 4.5 hours. The solvent was removed from the resultant mixed liquid by distillation, and then the resultant solid product was dried in a vacuum. As a result, a carboxylic acid of Compound (R)-8 in which the t-butyl group of Compound (R)-8 was substituted with hydrogen was obtained. A mixed solution of dry dimethylformamide (3.5 mL) and dry tetrahydrofuran (9.5 mL) in which the carboxylic acid of Compound (R)-8 (1.11 g, 1.46 mmol) was dissolved, DCC (459 mg, 2.23 mmol), and HOBT (301 mg, 2.23 mmol) were added to an aminopropyl silica gel (2.99 g) left standing to cool under nitrogen after having been dried in a vacuum at 150° C. for 4 hours. After the resultant slurry had been stirred with a mechanical stirrer at room temperature for 48 hours, DCC (463 mg, 2.25 mmol), HOBT (302 mg, 2.23 mmol), and acetic acid (0.23 mL, 4.0 mmol) were added to the slurry, and then the mixture was stirred for an additional 24 hours. A silica gel obtained by filtrating the resultant slurry was washed with tetrahydrofuran, ethanol, and hot ethanol in the stated order, and was then dried in a vacuum. As a result, CSP-2 as a white powder was obtained.

Example 3

Production of Column for HPLC With CSP-1

CSP-1 (3.5 g) was dispersed in methanol, and then a stainless column having a diameter of 0.46 cm and a length of 25 cm was filled with the resultant slurry according to a slurry mode. Thus, a column filled with CSP-1 was produced.

CSP-1 was evaluated for its asymmetry recognition ability with the resultant column under four kinds of evaluation conditions. The racemic bodies of Compounds 1 to 9 shown below were used as samples for evaluation. The following evaluation of the chiral stationary phase for its asymmetry recognition ability is described for the respective evaluation conditions. It should be noted that a retention coefficient (k') and a separation coefficient (α) in the following results of the evaluation are defined by the following equations. In the following equation, the dead time is the elution time of tritertiary butylbenzene.

Retention coefficient;

k'=[(retention time of antipode)−(dead time)]/dead time)

Separation coefficient;

α=(retention coefficient of antipode to be held more strongly)/(retention coefficient of antipode to be held more weakly)

[Chem 20]

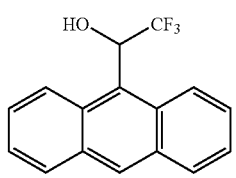

1

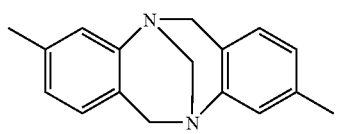

2

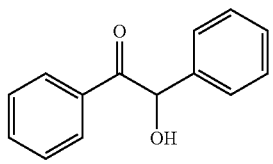

3

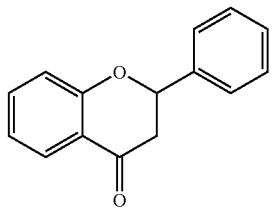

4

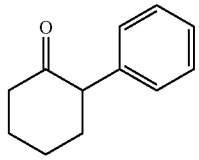

5

Co(CH$_3$COCHCOCH$_3$)$_3$

6

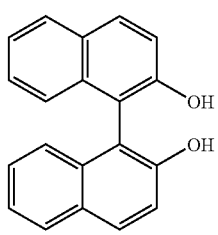

7

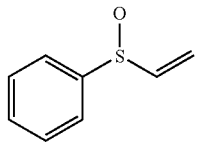

8

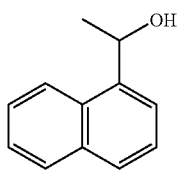

9

[Evaluation (1)]

The evaluation for the asymmetry recognition ability was performed with seven kinds of samples (Compound Nos.: 1, 2, 3, 4, 5, 6, and 7) under the following conditions by HPLC. Table 1 shows the results of the evaluation. In addition, FIGS. 1 to 7 illustrate the chromatograms of the respective samples for evaluation. It should be noted that, in the table, t0 represents the dead time (min), t1 represents the elution time (min) of an antipode to be held more weakly, t2 represents the elution time (min) of an antipode to be held more strongly, k1' represents the retention coefficient of the antipode to be held more weakly, and k2' represents the retention coefficient of the antipode to be held more strongly.

(Evaluation Conditions 1)
Moving phase: hexane/2-propanol=9/1(v/v)
Flow rate: 1.0 mL/min.
Temperature: 25° C.
Detection: UV 254 nm (225 nm for Sample 5 alone)

TABLE 1

| Sample | 1 | 2 | 3 | 4 | 5 | 6 | 7 |
|---|---|---|---|---|---|---|---|
| t0 | 3.05 | | | | | | |
| t1 | 8.60 | 5.08 | 12.35 | 6.45 | 6.32 | 21.91 | 26.39 |
| t2 | 8.95 | 5.27 | 19.07 | 6.69 | 6.67 | 32.65 | 27.72 |
| k1' | 1.82 | 0.67 | 3.05 | 1.11 | 1.07 | 6.18 | 7.65 |
| k2' | 1.93 | 0.73 | 5.25 | 1.19 | 1.19 | 9.70 | 8.09 |
| α | 1.06 | 1.09 | 1.72 | 1.07 | 1.11 | 1.57 | 1.06 |

[Evaluation (2)]

The evaluation for the asymmetry recognition ability was performed with seven kinds of samples for evaluation (Compound Nos.: 1, 2, 3, 4, 5, 6, and 8) under the following conditions by HPLC. Table 2 below shows the results of the evaluation. In addition, FIGS. 8 to 14 illustrate the chromatograms of the respective samples for evaluation.

(Evaluation Conditions 2)
Moving phase: hexane/chloroform mixed solution (composition ratio (v/v) is described in Table 2)
Flow rate: 1.0 mL/min.
Temperature: 25° C.
Detection: UV 254 nm (225 nm for Sample 5 alone)

TABLE 2

| Sample | 1 | 2 | 3 | 4 | 5 | 6 | 8 |
|---|---|---|---|---|---|---|---|
| Composition | 8/2 | 95/5 | 85/15 | 95/5 | 9/1 | 95/5 | 8/2 |
| t0 | 3.20 | | | | | | |
| t1 | 51.82 | 23.92 | 26.19 | 16.13 | 12.34 | 13.33 | 41.40 |
| t2 | 53.70 | 25.44 | 41.83 | 16.79 | 13.64 | 17.25 | 51.27 |
| k1' | 15.19 | 6.48 | 7.18 | 4.04 | 2.86 | 3.17 | 11.94 |
| k2' | 15.78 | 6.95 | 12.07 | 4.25 | 3.26 | 4.39 | 15.02 |
| α | 1.04 | 1.07 | 1.68 | 1.05 | 1.14 | 1.39 | 1.26 |

[Evaluation (3)]

Figure 15:
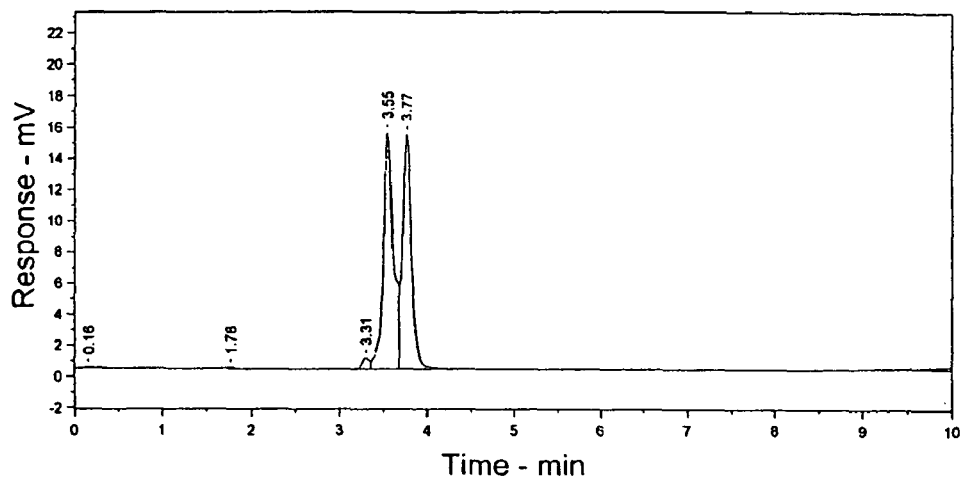
FIG. 15 illustrates a chromatogram of Evaluation Sample 3 in Evaluation 3 of Example 3.
Figure 16:
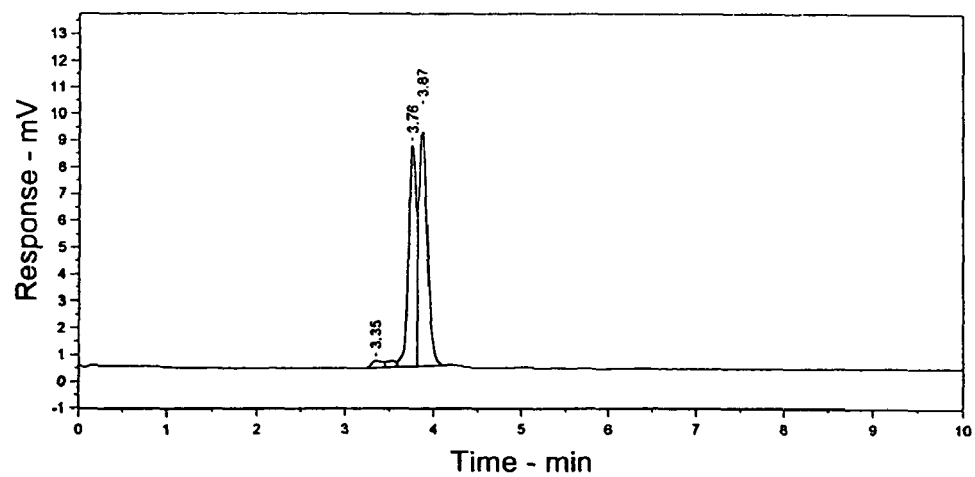
FIG. 16 illustrates a chromatogram of Evaluation Sample 8 in Evaluation 3 of Example 3.
Figure 17:
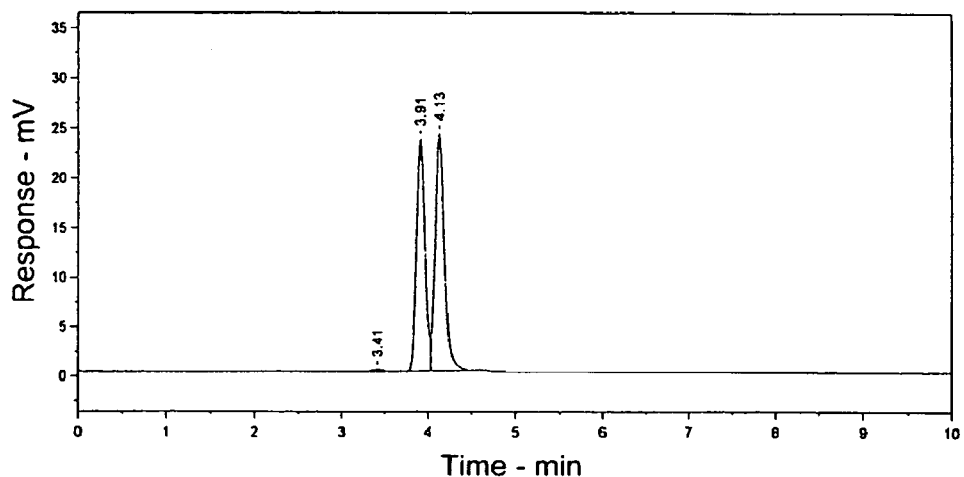
FIG. 17 illustrates a chromatogram of Evaluation Sample 2 in Evaluation 4 of Example 3.
Figure 18:
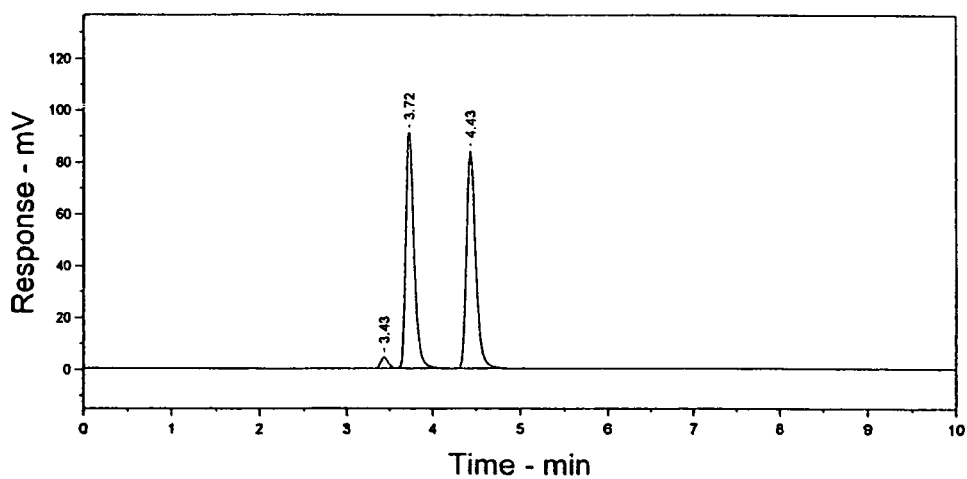
FIG. 18 illustrates a chromatogram of Evaluation Sample 3 in Evaluation 4 of Example 3.
Figure 19:
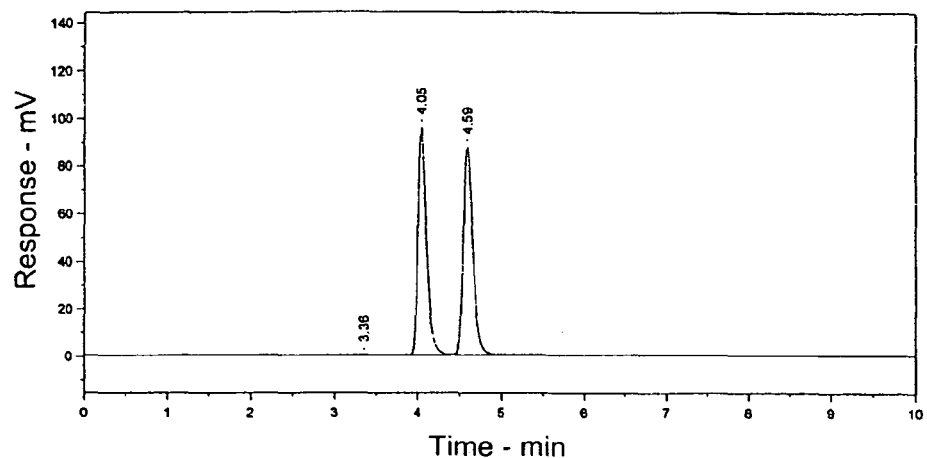
FIG. 19 illustrates a chromatogram of Evaluation Sample 6 in Evaluation 4 of Example 3.
Figure 20:
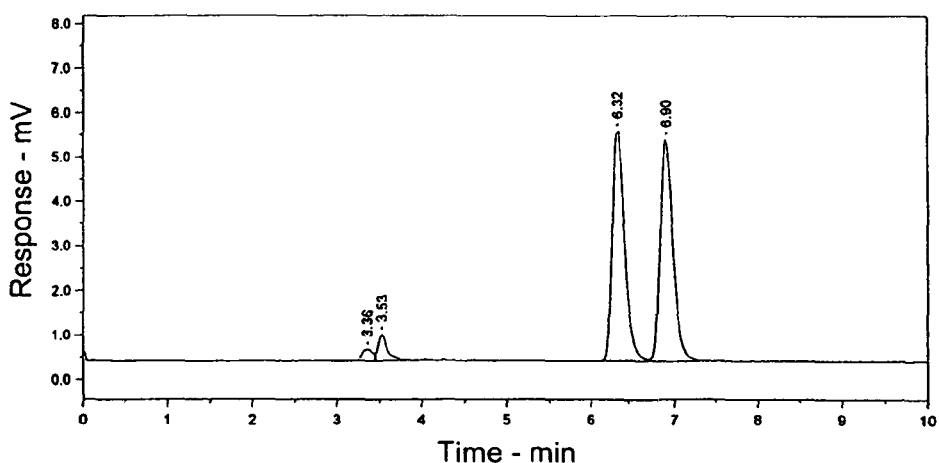
FIG. 20 illustrates a chromatogram of Evaluation Sample 8 in Evaluation 4 of Example 3.
Figure 21:
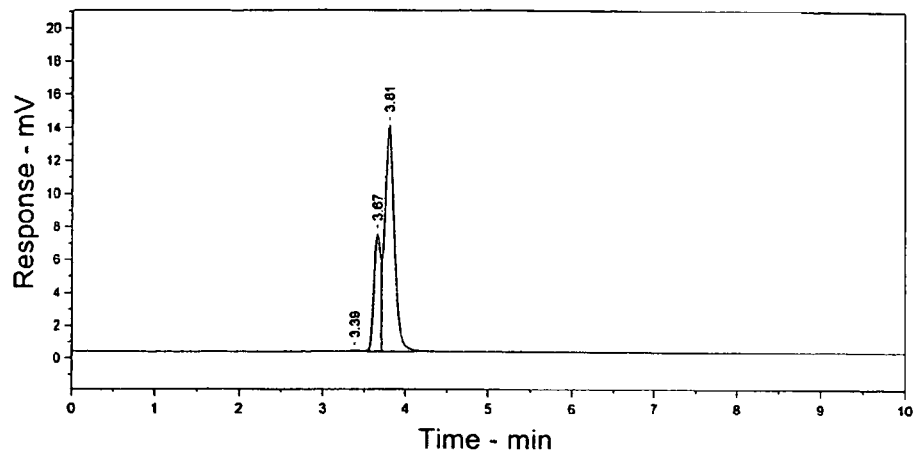
FIG. 21 illustrates a chromatogram of Evaluation Sample 9 in Evaluation 4 of Example 3.
Figure 22:
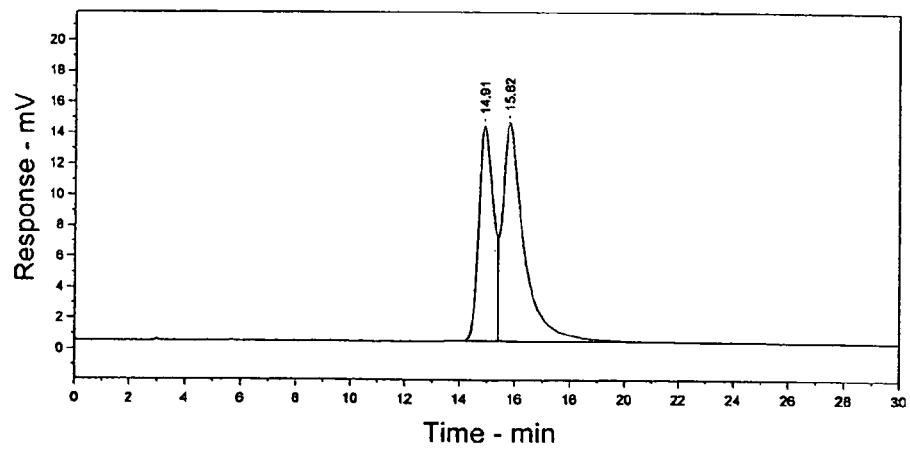
FIG. 22 illustrates a chromatogram of Evaluation Sample 1 in Evaluation 1 of Example 4.
Figure 23:
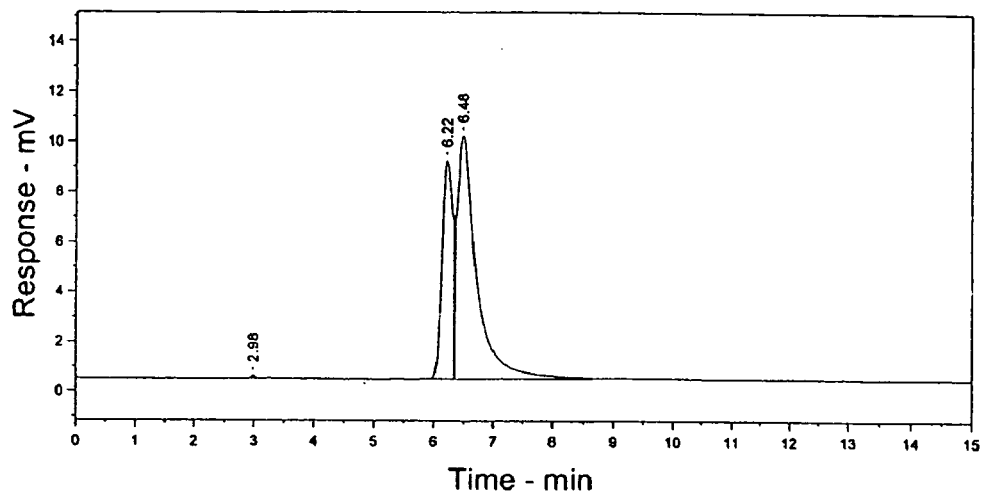
FIG. 23 illustrates a chromatogram of Evaluation Sample 2 in Evaluation 1 of Example 4.
Figure 24:
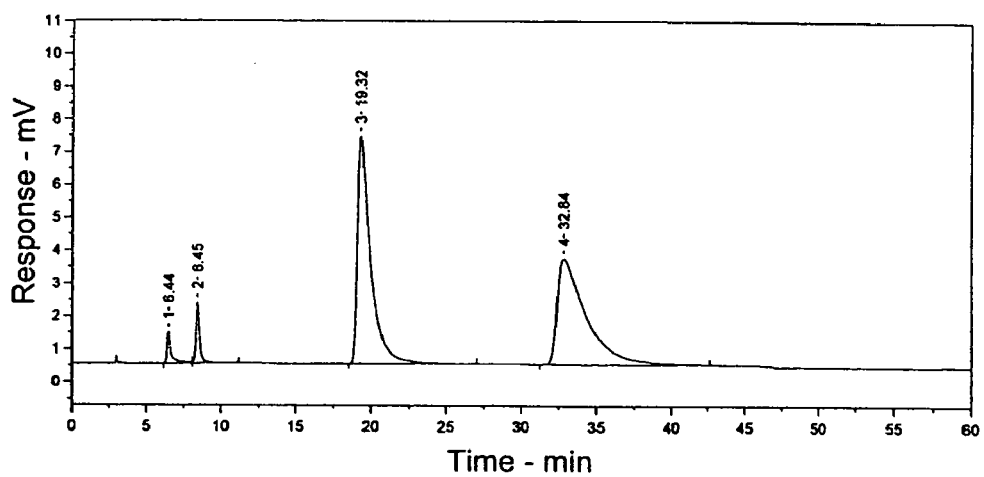
FIG. 24 illustrates a chromatogram of Evaluation Sample 3 in Evaluation 1 of Example 4.
Figure 25:
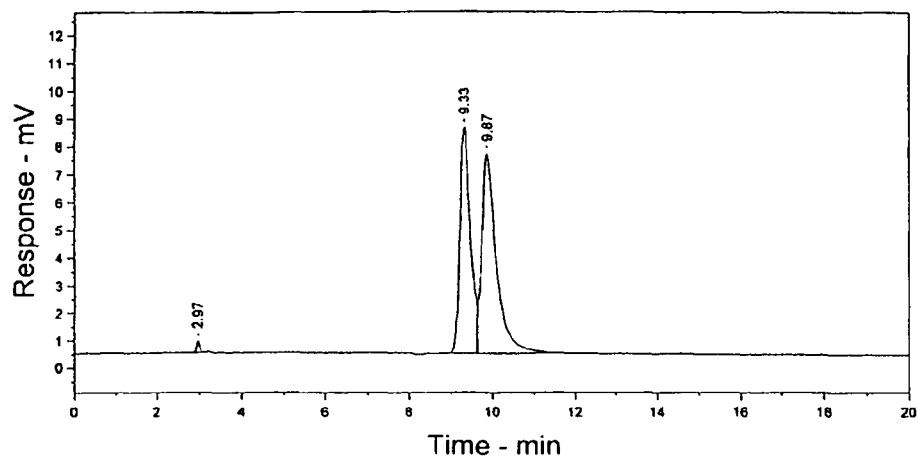
FIG. 25 illustrates a chromatogram of Evaluation Sample 4 in Evaluation 1 of Example 4.
Figure 26:
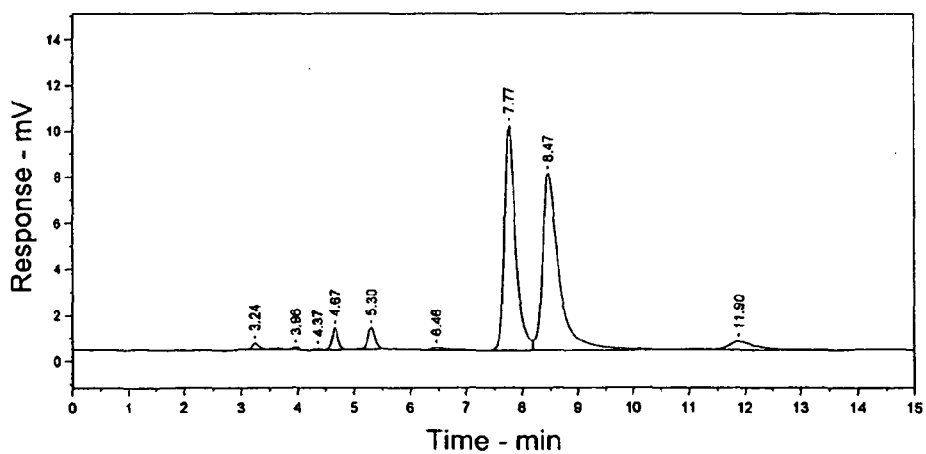
FIG. 26 illustrates a chromatogram of Evaluation Sample 5 in Evaluation 1 of Example 4.
Figure 27:
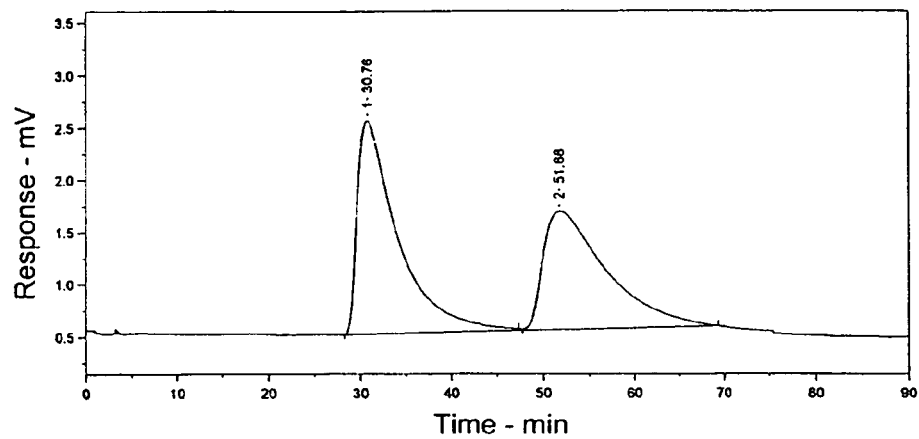
FIG. 27 illustrates a chromatogram of Evaluation Sample 6 in Evaluation 1 of Example 4.
Figure 28:
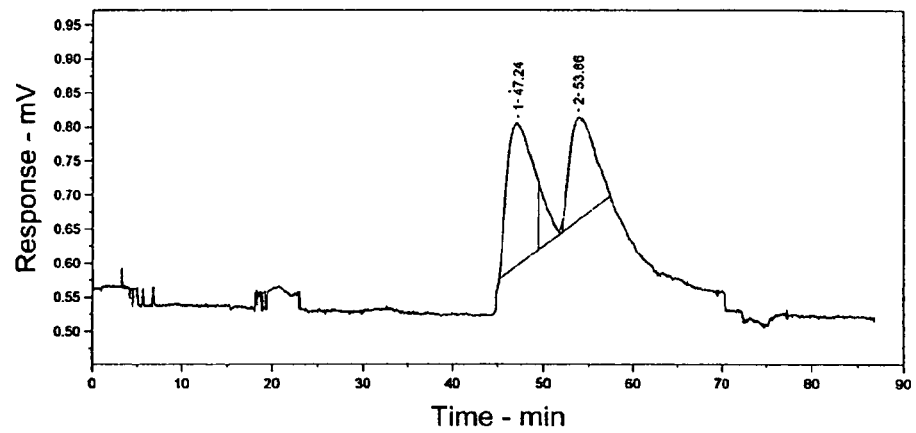
FIG. 28 illustrates a chromatogram of Evaluation Sample 7 in Evaluation 1 of Example 4.
Figure 29:
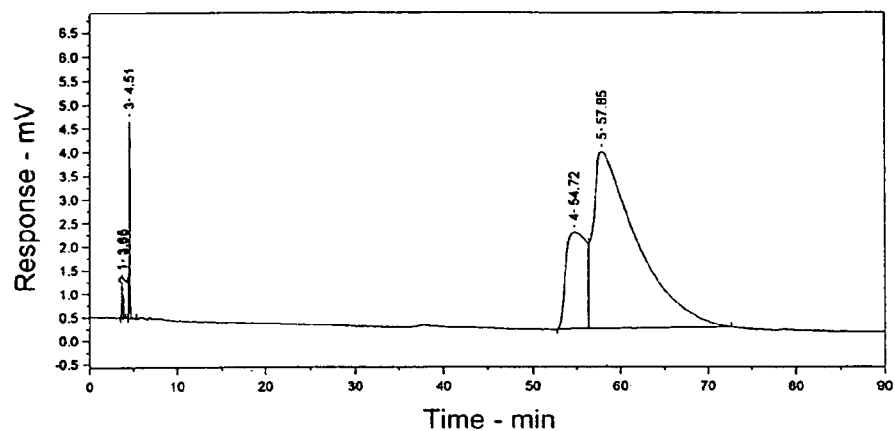
FIG. 29 illustrates a chromatogram of Evaluation Sample 8 in Evaluation 1 of Example 4.
Figure 30:
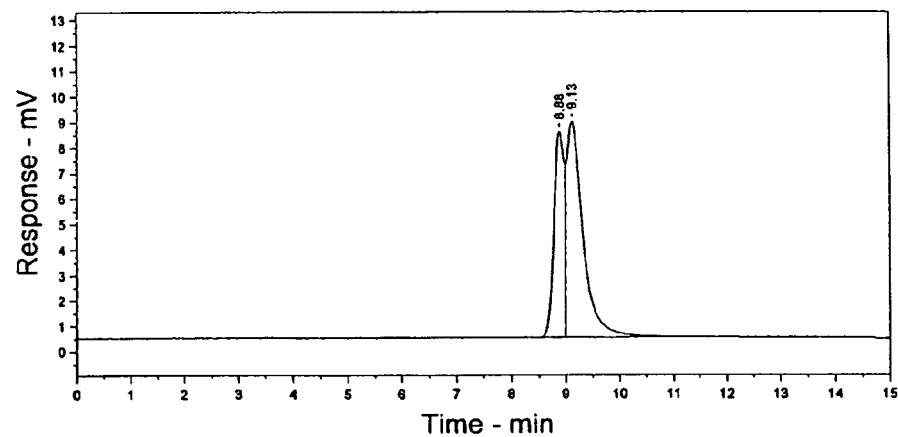
FIG. 30 illustrates a chromatogram of Evaluation Sample 9 in Evaluation 1 of Example 4.
Figure 31:
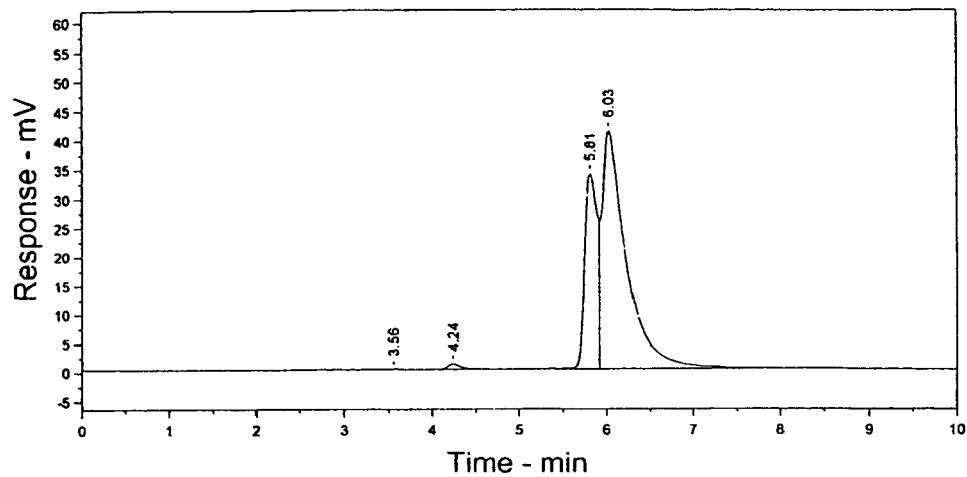
FIG. 31 illustrates a chromatogram of Evaluation Sample 2 in Evaluation 2 of Example 4.
Figure 32:
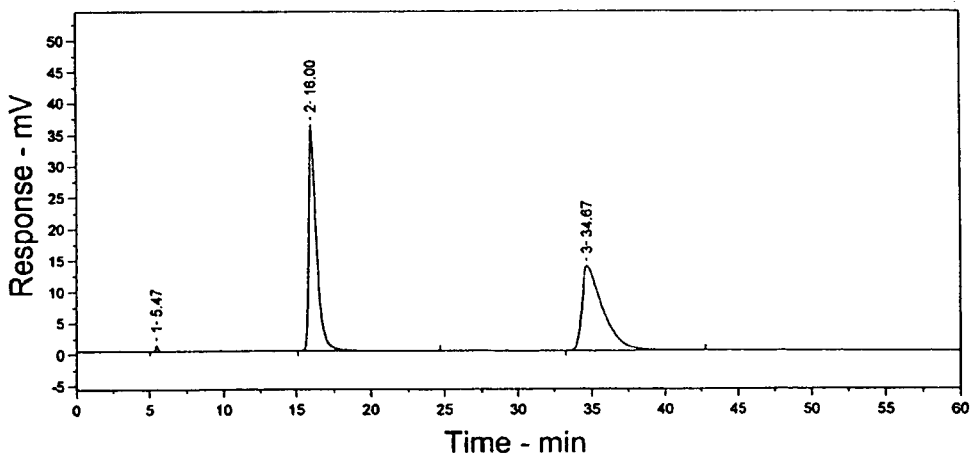
FIG. 32 illustrates a chromatogram of Evaluation Sample 3 in Evaluation 2 of Example 4.
Figure 33:
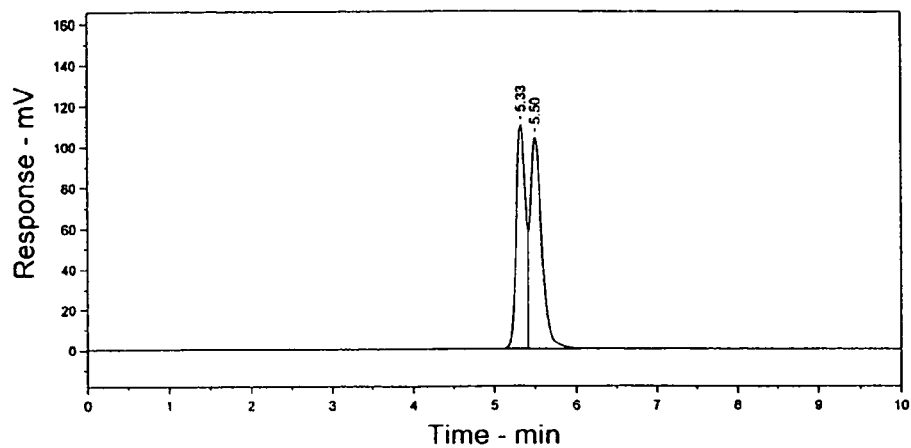
FIG. 33 illustrates a chromatogram of Evaluation Sample 4 in Evaluation 2 of Example 4.
Figure 34:
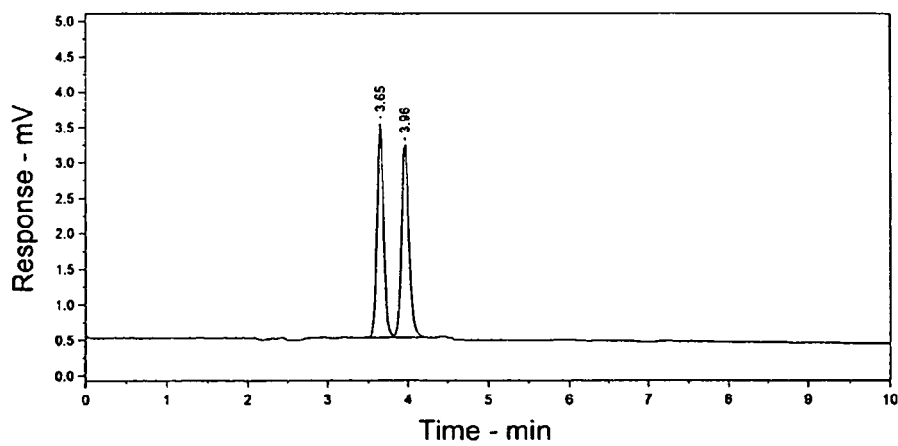
FIG. 34 illustrates a chromatogram of Evaluation Sample 5 in Evaluation 2 of Example 4.
Figure 35:
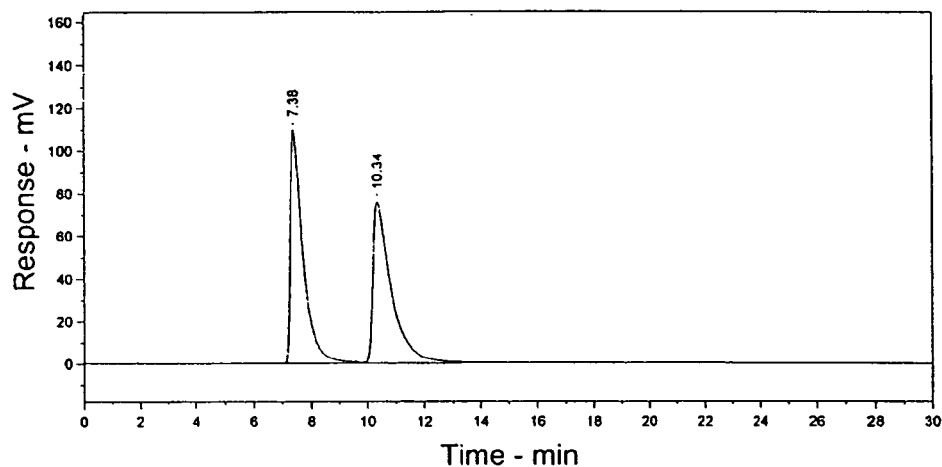
FIG. 35 illustrates a chromatogram of Evaluation Sample 6 in Evaluation 2 of Example 4.
Figure 36:
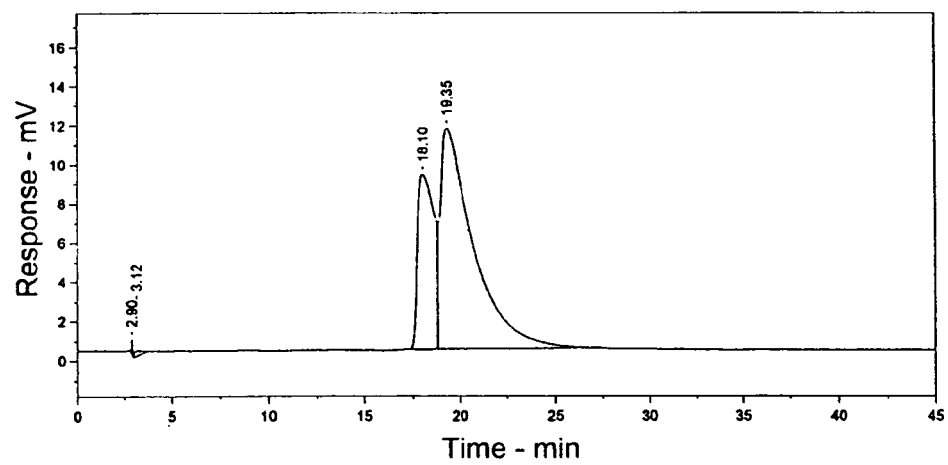
FIG. 36 illustrates a chromatogram of Evaluation Sample 7 in Evaluation 2 of Example 4.
Figure 37:
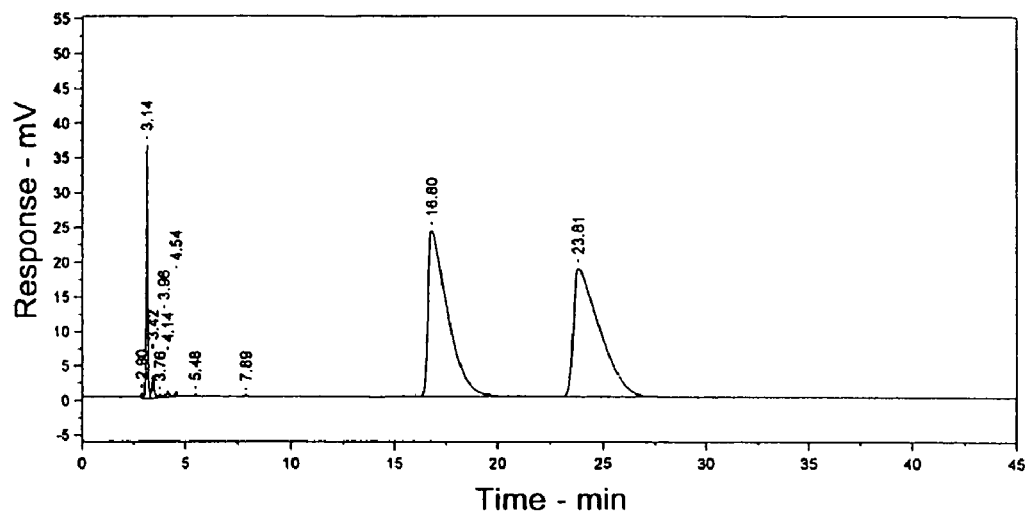
FIG. 37 illustrates a chromatogram of Evaluation Sample 8 in Evaluation 2 of Example 4.
Figure 38:
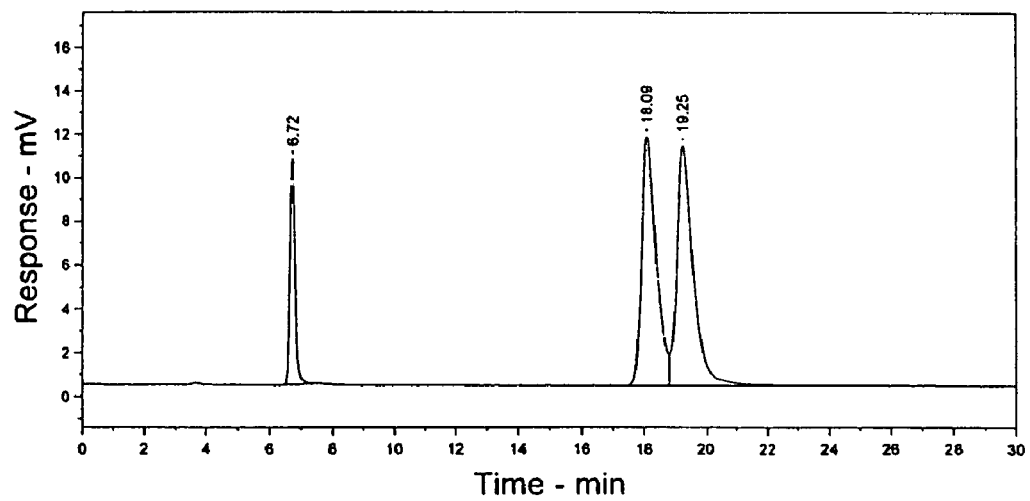
FIG. 38 illustrates a chromatogram of Evaluation Sample 9 in Evaluation 2 of Example 4.
Figure 39:
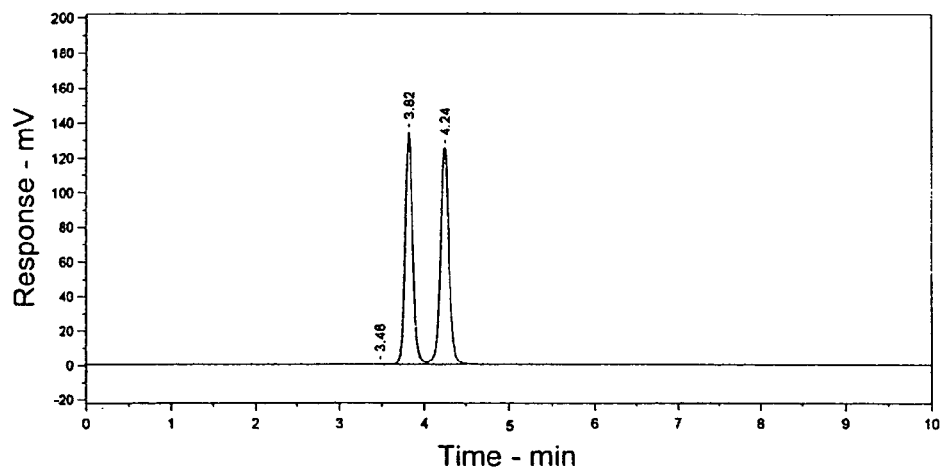
FIG. 39 illustrates a chromatogram of Evaluation Sample 3 in Evaluation 3 of Example 4.
Figure 40:
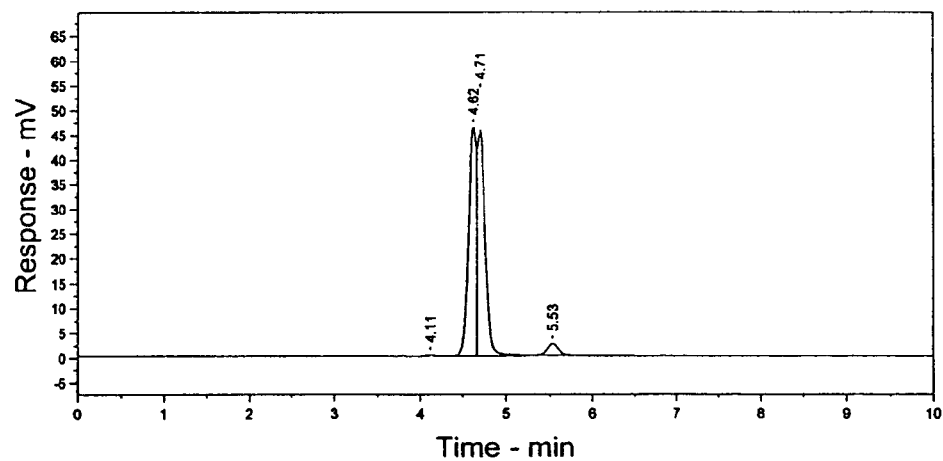
FIG. 40 illustrates a chromatogram of Evaluation Sample 4 in Evaluation 3 of Example 4.
Figure 41:
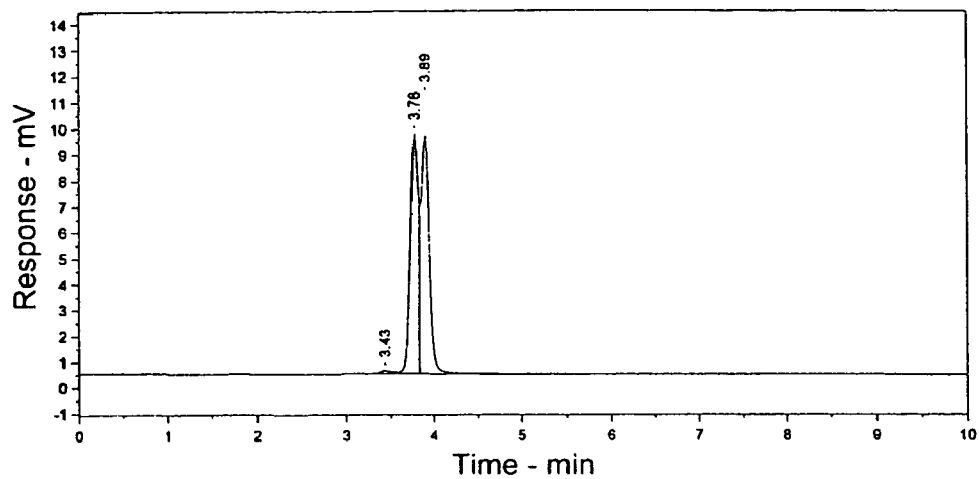
FIG. 41 illustrates a chromatogram of Evaluation Sample 6 in Evaluation 3 of Example 4.
Figure 42:
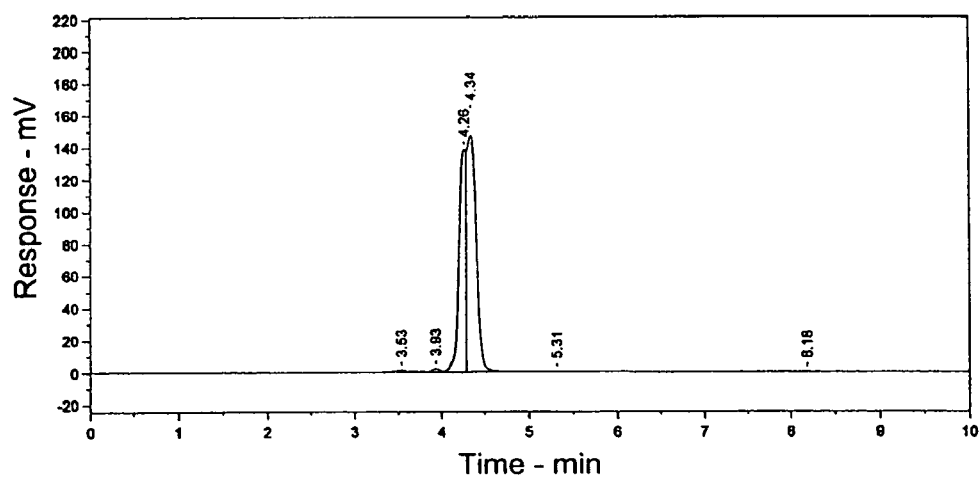
FIG. 42 illustrates a chromatogram of Evaluation Sample 8 in Evaluation 3 of Example 4.
Figure 43:
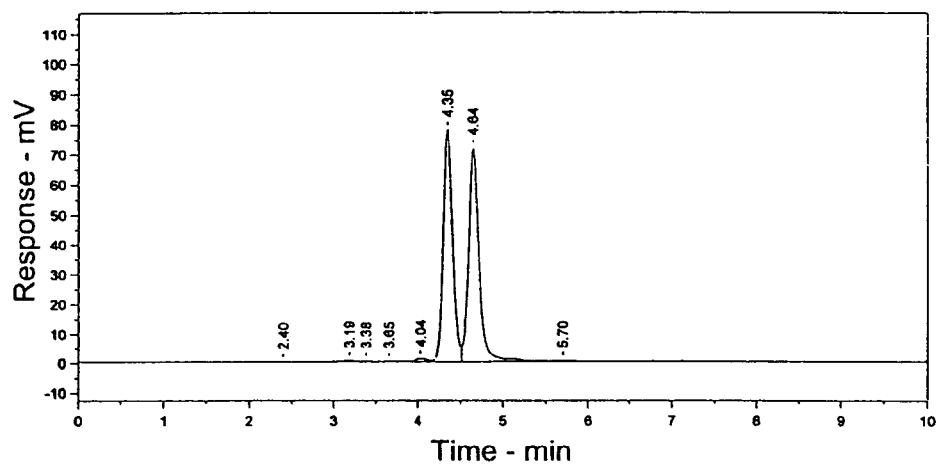
FIG. 43 illustrates a chromatogram of Evaluation Sample 2 in Evaluation 4 of Example 4.
Figure 44:
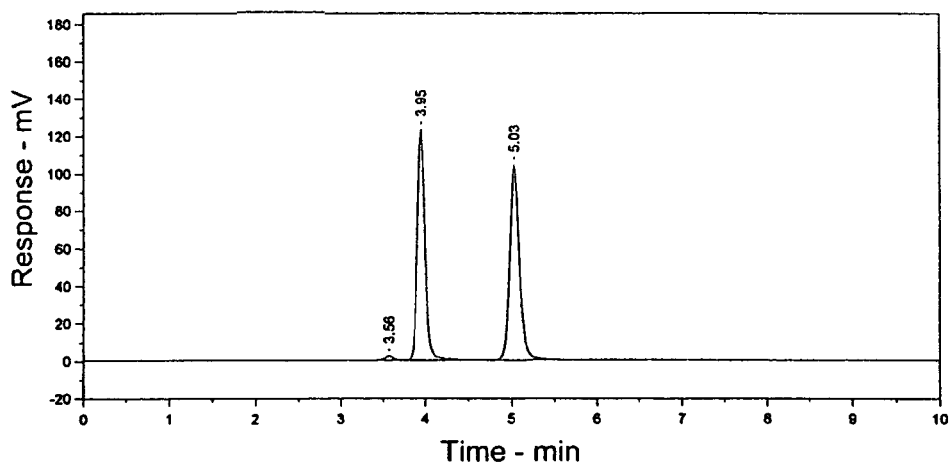
FIG. 44 illustrates a chromatogram of Evaluation Sample 3 in Evaluation 4 of Example 4.
Figure 45:
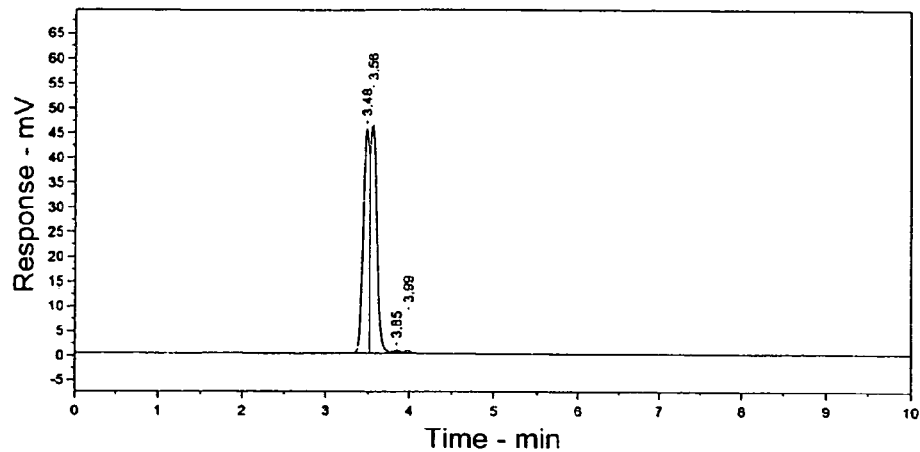
FIG. 45 illustrates a chromatogram of Evaluation Sample 5 in Evaluation 4 of Example 4.
Figure 46:
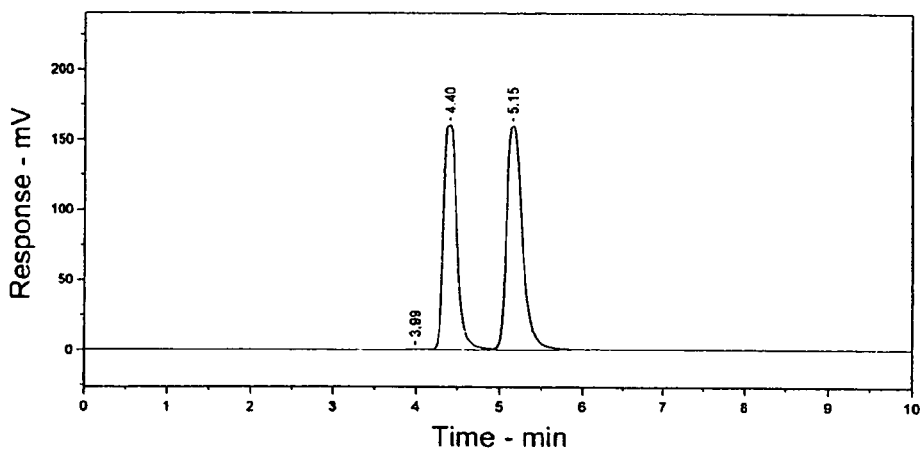
FIG. 46 illustrates a chromatogram of Evaluation Sample 6 in Evaluation 4 of Example 4.
Figure 47:
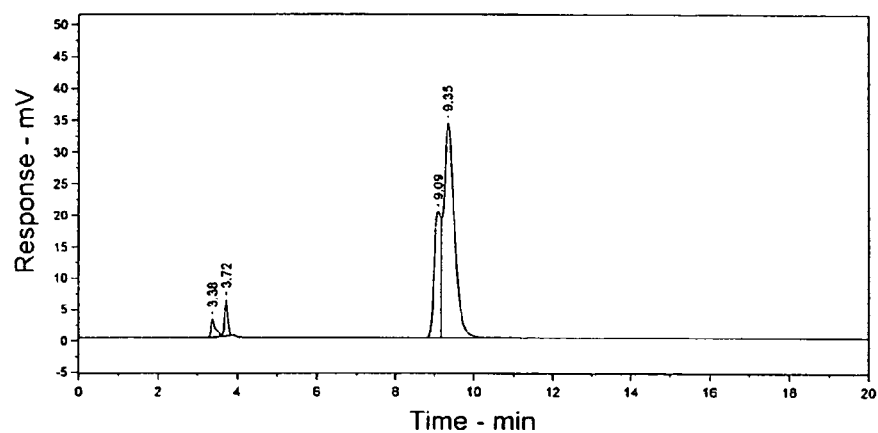
FIG. 47 illustrates a chromatogram of Evaluation Sample 8 in Evaluation 4 of Example 4.
Figure 48:
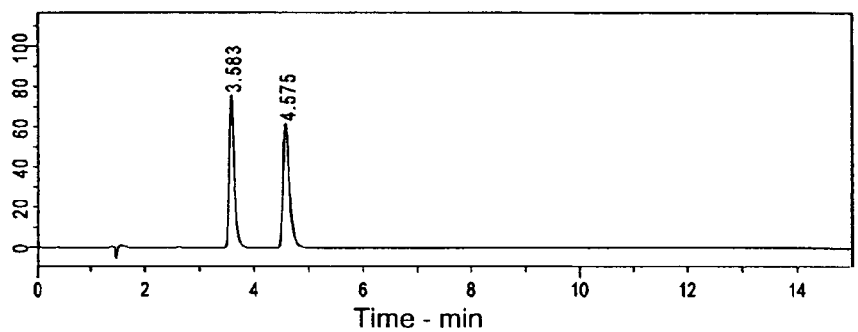
FIG. 48 illustrates a chromatogram of Evaluation Sample 3 (moving phase: $CO_2$/MeOH) in Evaluation 1 of Example 5.
Figure 49:
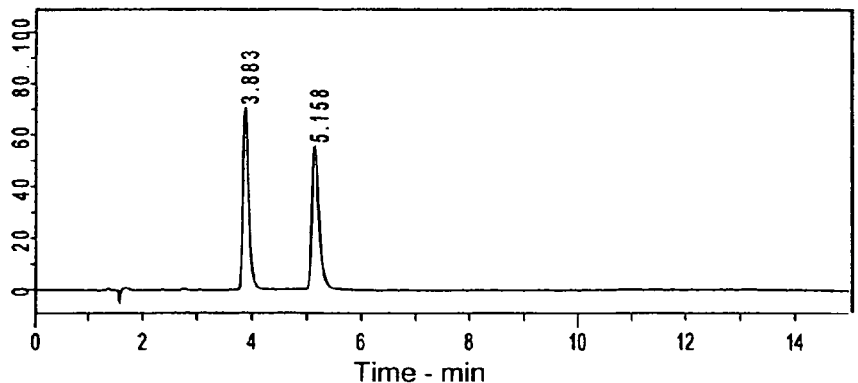
FIG. 49 illustrates a chromatogram of Evaluation Sample 3 (moving phase: $CO_2$/EtOH) in Evaluation 1 of Example 5.
Figure 50:
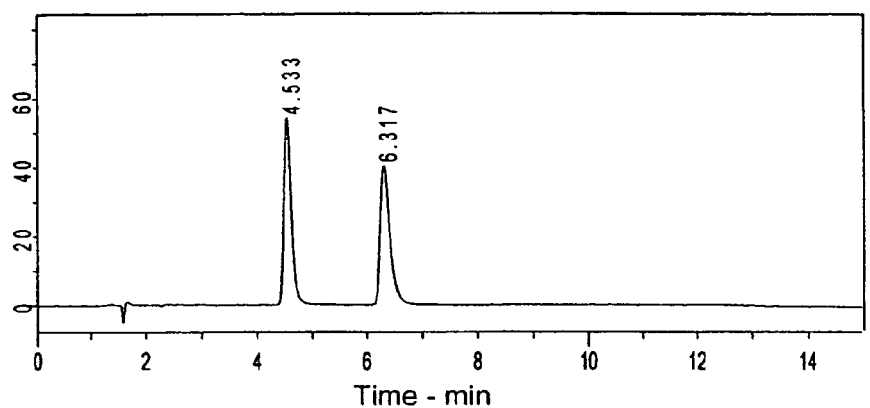
FIG. 50 illustrates a chromatogram of Evaluation Sample 3 (moving phase: $CO_2$/IPA) in Evaluation 1 of Example 5.
Figure 51:
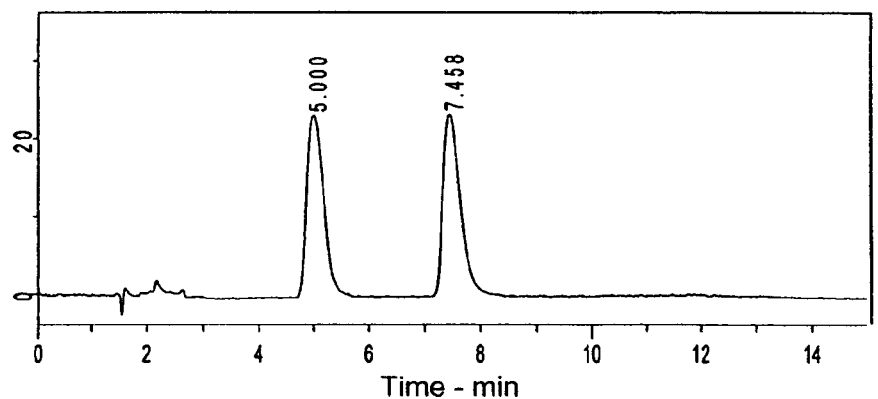
FIG. 51 illustrates a chromatogram of Evaluation Sample 3 (moving phase: $CO_2$/MeCN) in Evaluation 1 of Example 5.
Figure 52:
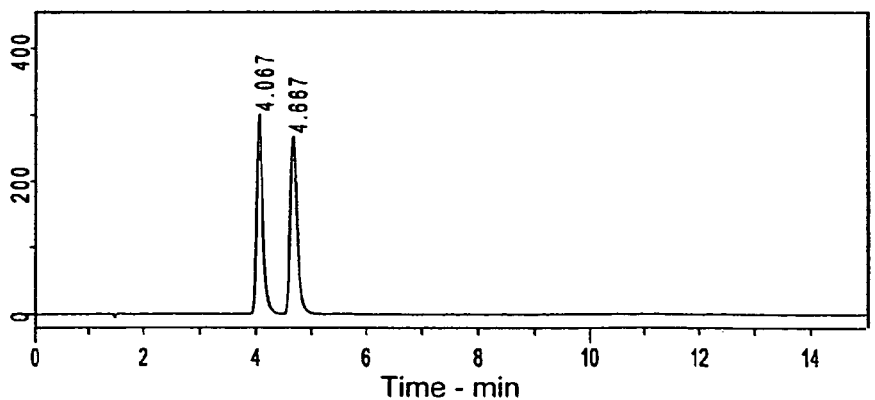
FIG. 52 illustrates a chromatogram of Evaluation Sample 6 (moving phase: $CO_2$/MeOH) in Evaluation 1 of Example 5.
Figure 53:
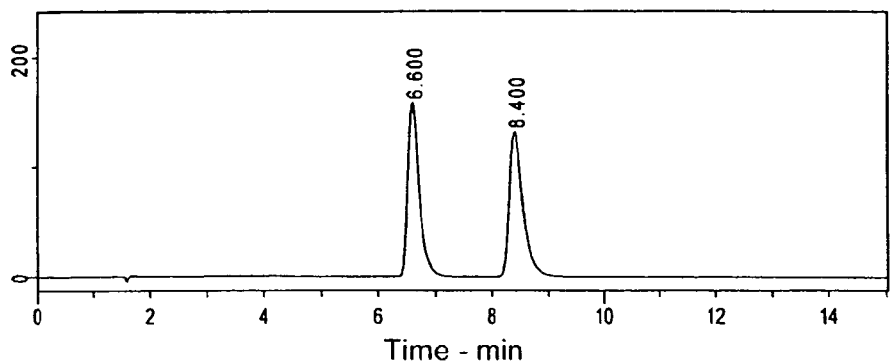
FIG. 53 illustrates a chromatogram of Evaluation Sample 6 (moving phase: $CO_2$/EtOH) in Evaluation 1 of Example 5.
Figure 54:
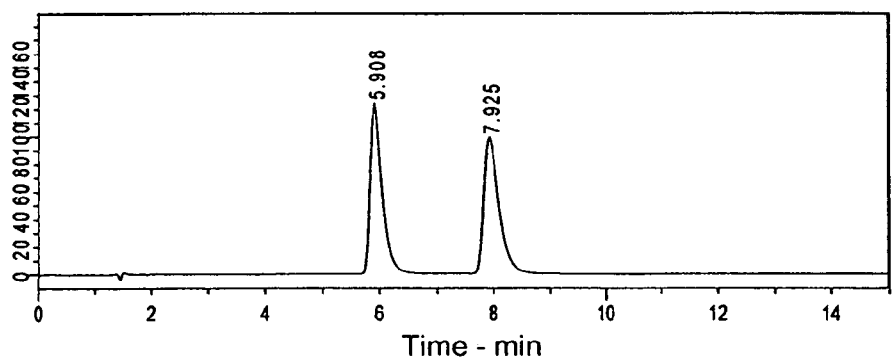
FIG. 54 illustrates a chromatogram of Evaluation Sample 6 (moving phase: $CO_2$/IPA) in Evaluation 1 of Example 5.
Figure 55:
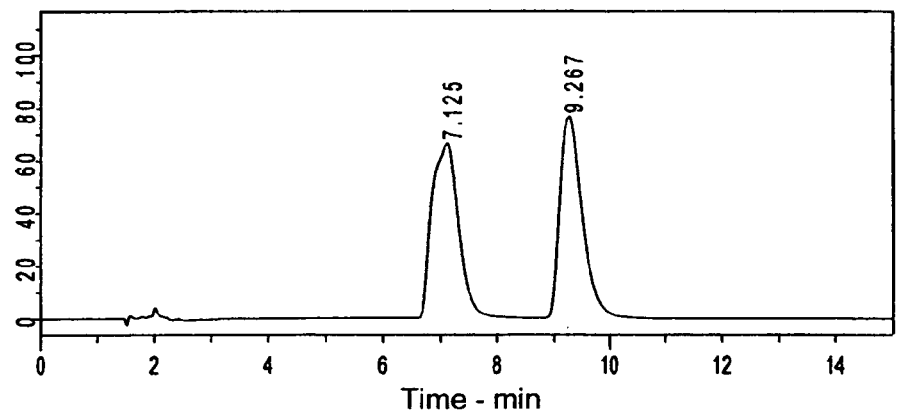
FIG. 55 illustrates a chromatogram of Evaluation Sample 6 (moving phase: $CO_2$/MeCN) in Evaluation 1 of Example 5.
Figure 56:
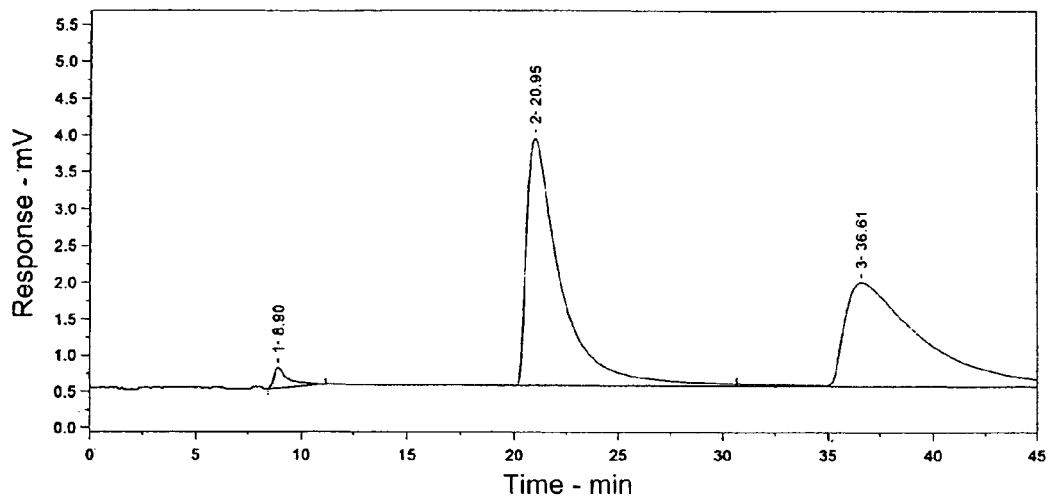
FIG. 56 illustrates a chromatogram of Evaluation Sample 3 in Evaluation 1 of Example 11.
Figure 57:
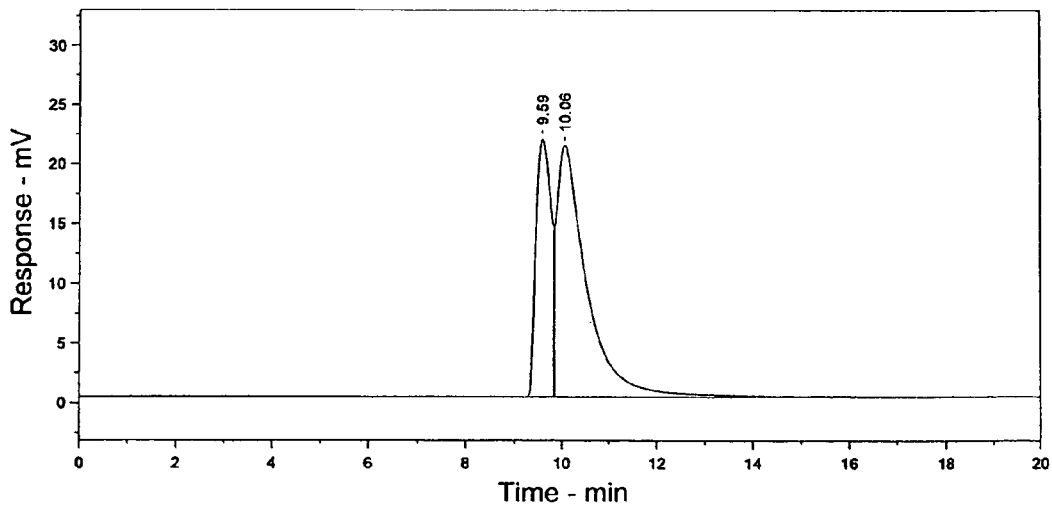
FIG. 57 illustrates a chromatogram of Evaluation Sample 4 in Evaluation 1 of Example 11.
Figure 58:
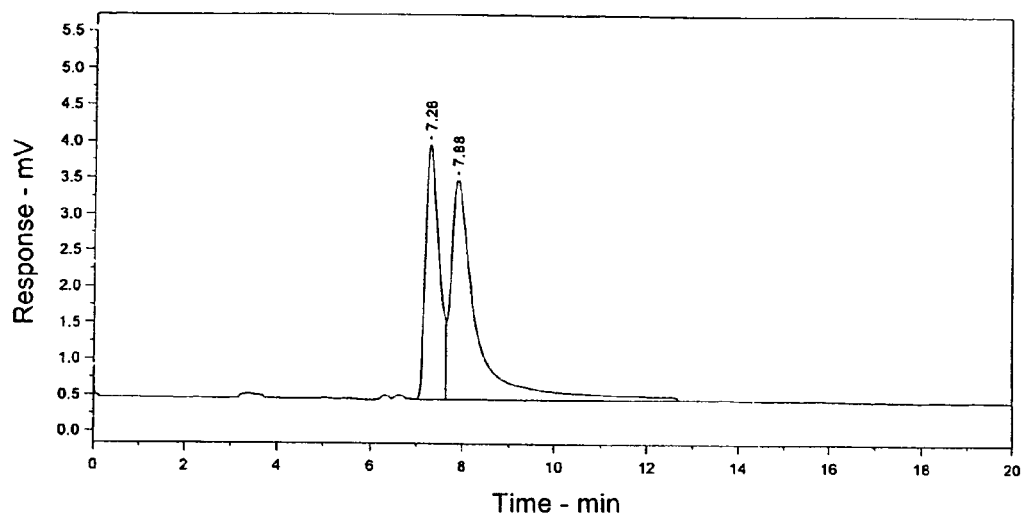
FIG. 58 illustrates a chromatogram of Evaluation Sample 5 in Evaluation 1 of Example 11.
Figure 59:
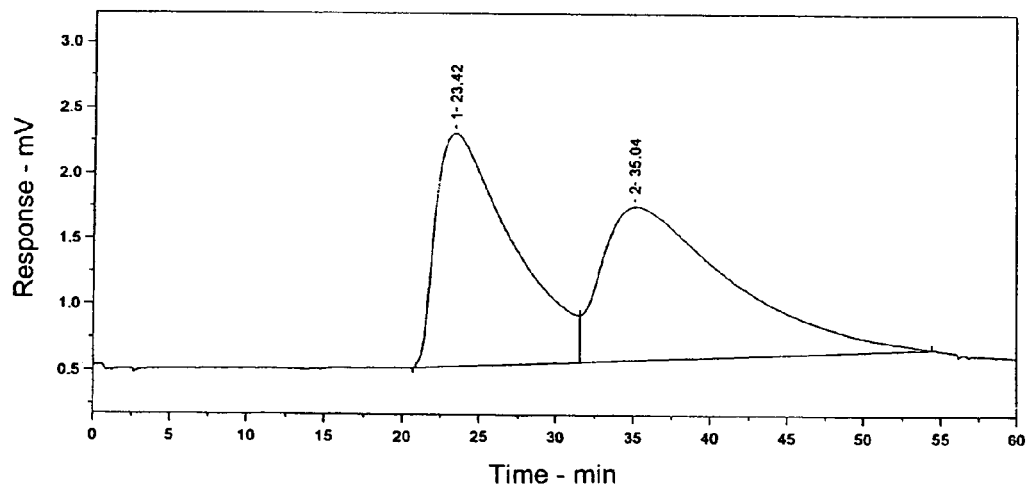
FIG. 59 illustrates a chromatogram of Evaluation Sample 6 in Evaluation 1 of Example 11.
Figure 60:
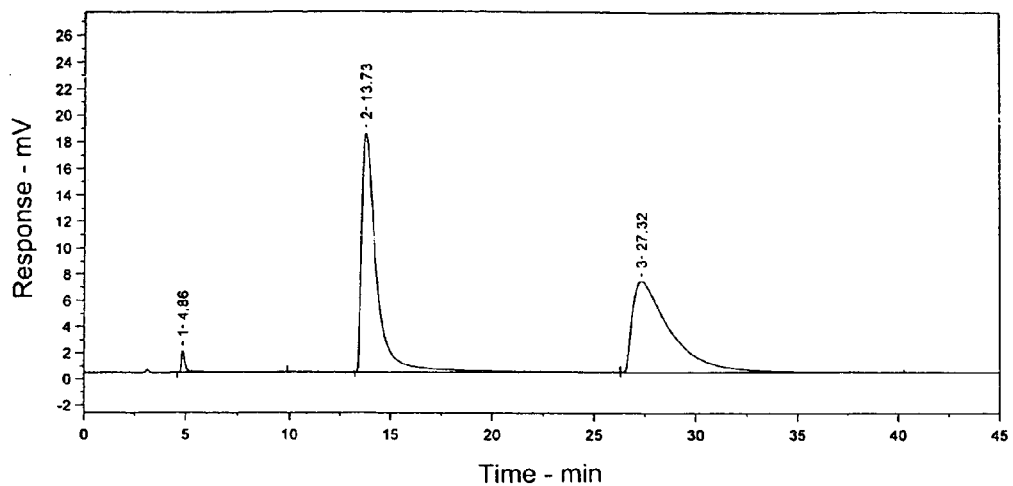
FIG. 60 illustrates a chromatogram of Evaluation Sample 3 in Evaluation 2 of Example 11.
Figure 61:
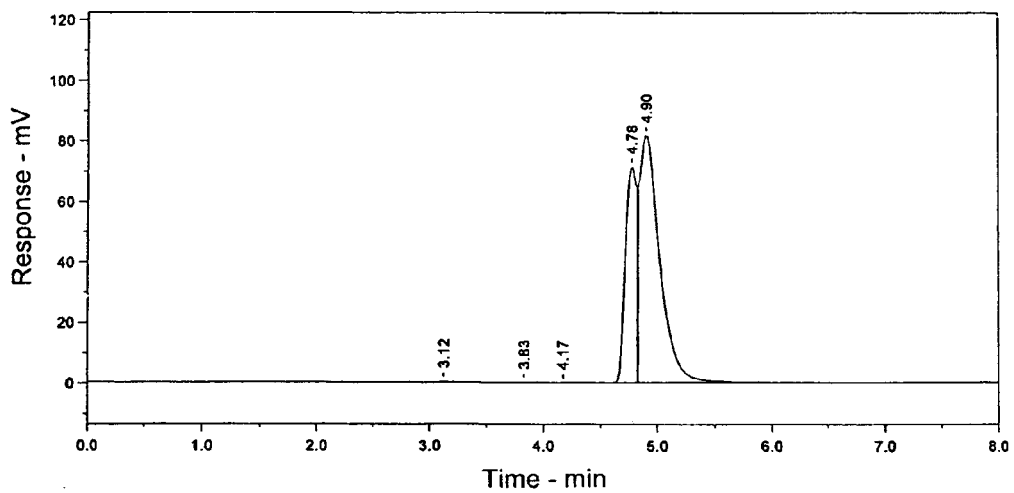
FIG. 61 illustrates a chromatogram of Evaluation Sample 4 in Evaluation 2 of Example 11.
Figure 62:
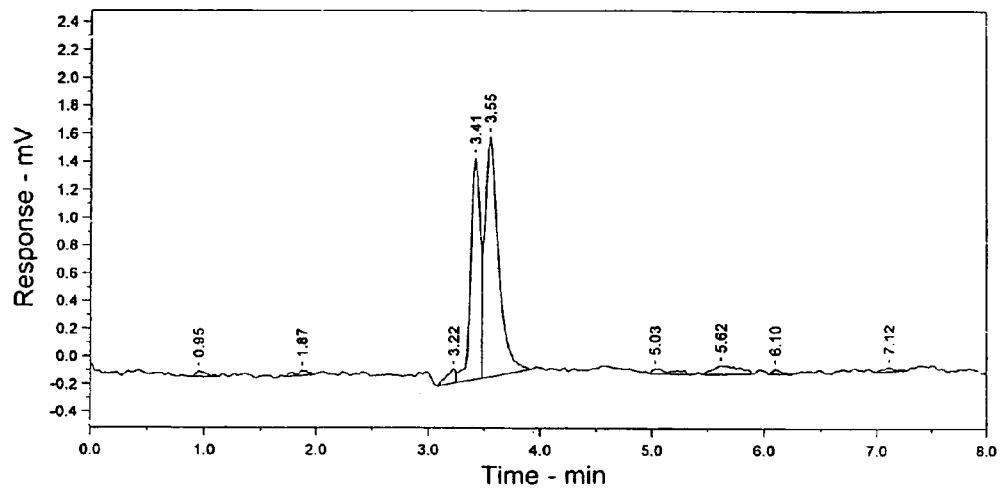
FIG. 62 illustrates a chromatogram of Evaluation Sample 5 in Evaluation 2 of Example 11.
Figure 63:
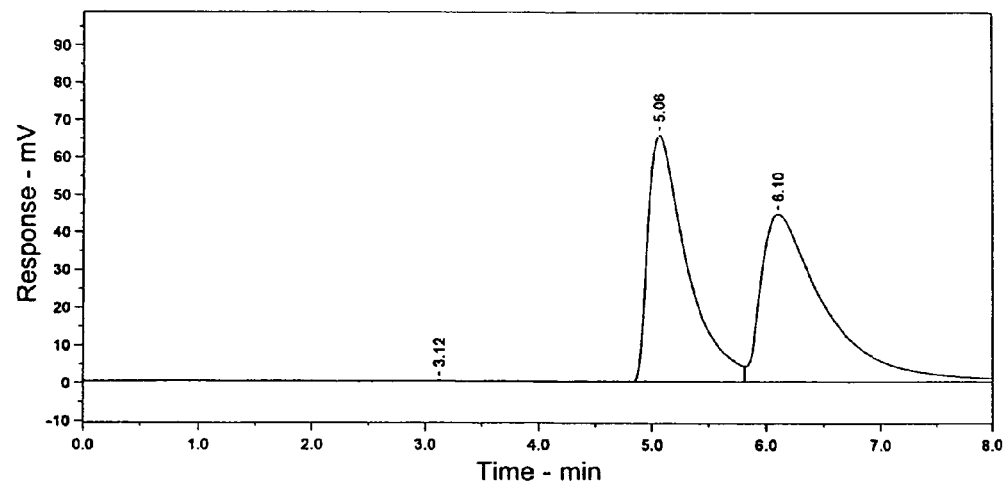
FIG. 63 illustrates a chromatogram of Evaluation Sample 6 in Evaluation 2 of Example 11.
Figure 64:
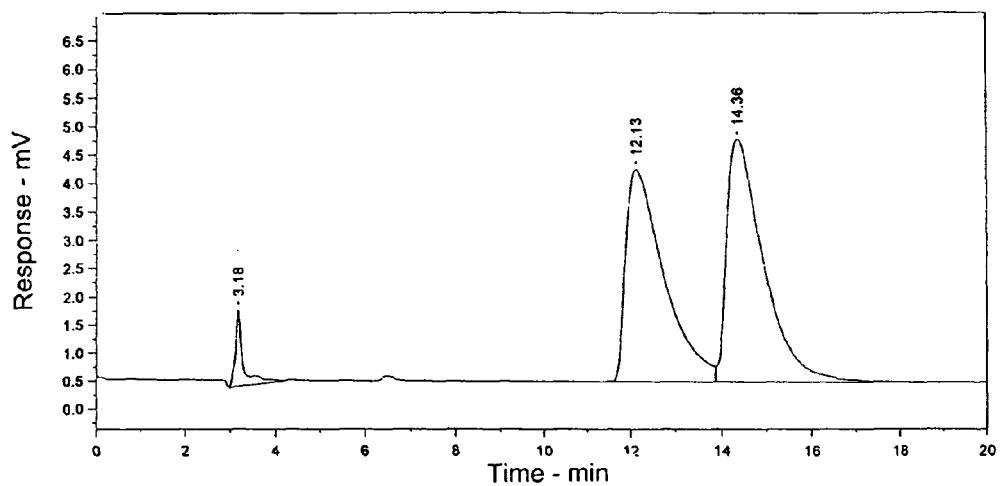
FIG. 64 illustrates a chromatogram of Evaluation Sample 8 in Evaluation 2 of Example 11.

The evaluation for the asymmetry recognition ability was performed with two kinds of samples for evaluation (Compound Nos.: 3 and 8) under the following conditions by HPLC. Table 3 shows the results of the evaluation. In addition, FIGS. 15 and 16 illustrate the chromatograms of the respective samples for evaluation.

(Evaluation Conditions 3)
Moving phase: methanol
Flow rate: 1.0 mL/min.
Temperature: 25° C.
Detection: UV 254 nm

TABLE 3

| Sample | 3 | 8 |
|---|---|---|
| t0 | 3.16 | |
| t1 | 3.55 | 3.76 |
| t2 | 3.77 | 3.87 |
| k1' | 0.12 | 0.19 |
| k2' | 0.19 | 0.22 |
| α | 1.56 | 1.18 |

[Evaluation (4)]

The evaluation for the asymmetry recognition ability was performed with five kinds of samples for evaluation (Compound Nos.: 2, 3, 6, 8, and 9) under the following conditions by HPLC. Table 4 shows the results of the evaluation. In addition, FIGS. 17 to 21 illustrate the chromatograms of the respective samples for evaluation.

(Evaluation Conditions 4)
Moving phase: acetonitrile
Flow rate: 1.0 mL/min.
Temperature: 25° C.
Detection: UV 254 nm

TABLE 4

| Sample | 2 | 3 | 6 | 8 | 9 |
|---|---|---|---|---|---|
| t0 | 3.18 | | | | |
| t1 | 3.91 | 3.72 | 4.05 | 6.32 | 3.67 |
| t2 | 4.13 | 4.43 | 4.59 | 6.90 | 3.81 |
| k1' | 0.23 | 0.17 | 0.27 | 0.99 | 0.15 |
| k2' | 0.30 | 0.39 | 0.44 | 1.17 | 0.20 |
| α | 1.30 | 2.31 | 1.62 | 1.18 | 1.29 |

Example 4

Production of Column for HPLC With CSP-2

CSP-2 (3.5 g) was dispersed in methanol, and then a stainless column having a diameter of 0.46 cm and a length of 25 cm was filled with the resultant slurry according to a slurry mode. Thus, a column filled with CSP-2 was produced.

CSP-2 was evaluated for its asymmetry recognition ability with the resultant column under four kinds of evaluation conditions. The racemic bodies of Compounds 1 to 9 were used as samples for evaluation. The following evaluation of the chiral stationary phase for its asymmetry recognition ability is described for the respective evaluation conditions.

[Evaluation (1)]

The evaluation for the asymmetry recognition ability was performed with nine kinds of samples for evaluation (Compound Nos.: 1, 2, 3, 4, 5, 6, 7, 8, and 9) under the following conditions by HPLC. Table 5 shows the results of the evaluation. In addition, FIGS. 22 to 30 illustrate the chromatograms of the respective samples for evaluation.

(Evaluation Conditions 1)
Moving phase: hexane/2-propanol=9/1(v/v)
Flow rate: 1.0 mL/min.

Temperature: 25° C.
Detection: UV 254 nm (225 nm for Sample 5 alone)

TABLE 5

| Sample | 1 | 2 | 3 | 4 | 5 | 6 | 7 | 8 | 9 |
|---|---|---|---|---|---|---|---|---|---|
| t0 | 3.00 | | | | | | | | |
| t1 | 14.91 | 6.22 | 19.32 | 9.33 | 7.77 | 30.76 | 47.24 | 54.72 | 8.88 |
| t2 | 15.82 | 6.48 | 32.84 | 9.87 | 8.47 | 51.68 | 53.86 | 57.85 | 9.13 |
| k1' | 3.97 | 1.07 | 5.44 | 2.11 | 1.59 | 9.25 | 7.62 | 17.24 | 1.96 |
| k2' | 4.27 | 1.16 | 9.95 | 2.29 | 1.82 | 16.23 | 8.73 | 18.28 | 2.04 |
| α | 1.08 | 1.08 | 1.83 | 1.09 | 1.15 | 1.75 | 1.14 | 1.06 | 1.04 |

[Evaluation (2)]

The evaluation for the asymmetry recognition ability was performed with eight kinds of samples for evaluation (Compound Nos.: 2, 3, 4, 5, 6, 7, 8, and 9) under the following conditions by HPLC. Table 6 shows the results of the evaluation. In addition, FIGS. 31 to 38 illustrate the chromatograms of the respective samples for evaluation.

(Evaluation Conditions 2)
Moving phase: hexane/chloroform mixed solution (composition ratio (v/v) is described in the table)
Flow rate: 1.0 mL/min.
Temperature: 25° C.
Detection: UV 254 nm (225 nm for Sample 5 alone)

TABLE 6

| Sample | 2 | 3 | 4 | 5 | 6 | 7 | 8 | 9 |
|---|---|---|---|---|---|---|---|---|
| Composition | 7/3 | 7/3 | 7/3 | 4/6 | 7/3 | 4/6 | 4/6 | 7/3 |
| t0 | 2.95 | | | | | | | |
| t1 | 5.81 | 16.00 | 5.33 | 3.65 | 7.38 | 18.10 | 16.80 | 18.09 |
| t2 | 6.03 | 34.67 | 5.50 | 3.96 | 10.34 | 19.35 | 23.81 | 19.25 |
| k1' | 0.97 | 4.42 | 0.81 | 0.24 | 1.50 | 5.14 | 4.69 | 5.13 |
| k2' | 1.04 | 10.75 | 0.86 | 0.34 | 2.51 | 5.56 | 7.07 | 5.53 |
| α | 1.08 | 2.43 | 1.07 | 1.44 | 1.67 | 1.08 | 1.51 | 1.08 |

[Evaluation (3)]

The evaluation for the asymmetry recognition ability was performed with four kinds of samples for evaluation (Compound Nos.: 3, 4, 6, and 8) under the following conditions by HPLC. Table 7 shows the results of the evaluation. In addition, FIGS. 39 to 42 illustrate the chromatograms of the respective samples for evaluation.

(Evaluation Conditions 3)
Moving phase: methanol
Flow rate: 1.0 mL/min.
Temperature: 25° C.
Detection: UV 254 nm

TABLE 7

| Sample | 3 | 4 | 6 | 8 |
|---|---|---|---|---|
| t0 | 3.22 | | | |
| t1 | 3.82 | 4.62 | 3.78 | 4.26 |
| t2 | 4.24 | 4.71 | 3.89 | 4.34 |
| k1' | 0.19 | 0.43 | 0.17 | 0.32 |
| k2' | 0.32 | 0.46 | 0.21 | 0.35 |
| α | 1.70 | 1.06 | 1.20 | 1.08 |

[Evaluation (4)]

The evaluation for the asymmetry recognition ability was performed with five kinds of samples for evaluation (Compound Nos.: 2, 3, 5, 6, and 8) under the following conditions by HPLC. Table 8 shows the results of the evaluation. In addition, FIGS. 43 to 47 illustrate the chromatograms of the respective samples for evaluation.

(Evaluation Conditions 4)
Moving phase: acetonitrile
Flow rate: 1.0 mL/min.
Temperature: 25° C.
Detection: UV 254 nm (225 nm for Sample 5 alone)

TABLE 8

| Sample | 2 | 3 | 5 | 6 | 8 |
|---|---|---|---|---|---|
| t0 | 3.17 | | | | |
| t1 | 4.35 | 3.95 | 3.48 | 4.40 | 9.09 |
| t2 | 4.64 | 5.03 | 3.56 | 5.15 | 9.35 |
| k1' | 0.37 | 0.25 | 0.10 | 0.39 | 1.87 |
| k2' | 0.46 | 0.59 | 0.12 | 0.62 | 1.95 |
| α | 1.25 | 2.38 | 1.26 | 1.61 | 1.04 |

Example 5

Separation of Optical Isomers by Supercritical Fluid Chromatography (SFC)

CSP-1 was evaluated for its asymmetry recognition ability with the column obtained in Example 3 under the following supercritical or subcritical evaluation conditions. Compounds 3 and 6 described above were used as samples for evaluation. The retention coefficient (k') and the separation coefficient (α) in the following results of the evaluation are each defined in the same manner as in the foregoing. The dead time is the elution time of tritertiary butylbenzene as in the case of the foregoing.

[Evaluation (1)]

The evaluation for the asymmetry recognition ability was performed with two kinds of samples (Compound Nos.: 3 and 6) under the following four conditions by SFC. Table 9 shows the results of the evaluation of Sample 3, and Table 10 shows the results of the evaluation of Sample 6. In addition, FIGS. 48 to 55 illustrate the chromatograms of the respective samples for evaluation in respective conditions. It should be noted that, in the table, t0 represents the dead time (min.), t1 represents the elution time (min.) of an antipode to be held more weakly, t2 represents the elution time (min.) of an antipode to be held more strongly, k1' represents the retention coefficient of the antipode to be held more weakly, and k2' represents the retention coefficient of the antipode to be held more strongly. In addition, in the table below, $CO_2$ represents carbon dioxide, IPA represents 2-propanol, MeCN represents acetonitrile, and EtOH represents ethanol.

(Evaluation Conditions of Sample 3)
Flow rate of moving phase: 2.5 mL/min.
Temperature: 25° C.
Detection: UV 220 nm
Back pressure: 10 MPa (Evaluation Conditions of Sample 6)
Flow rate of moving phase: 2.5 mL/min.
Temperature: 25° C.
Detection: UV 220 nm
Back pressure: 10 MPa

TABLE 9

| Moving Phase (v/v) | t0 | t1 | t2 | k1' | k2' | α |
|---|---|---|---|---|---|---|
| $CO_2$/MeOH = 90/10 | 1.40 | 3.58 | 4.58 | 1.56 | 2.27 | 1.46 |
| $CO_2$/EtOH = 90/10 | | 3.88 | 5.16 | 1.78 | 2.69 | 1.52 |
| $CO_2$/IPA = 90/10 | | 4.53 | 6.32 | 2.24 | 3.52 | 1.58 |
| $CO_2$/MeCN = 90/10 | | 5.00 | 7.46 | 2.58 | 4.33 | 1.68 |

TABLE 10
| Moving Phase (v/v) | t0 | t1 | t2 | k1' | k2' | α |
|---|---|---|---|---|---|---|
| CO$_2$/MeOH = 90/10 | 1.40 | 4.07 | 4.67 | 1.91 | 2.34 | 1.23 |
| CO$_2$/EtOH = 90/10 | | 6.60 | 8.40 | 3.72 | 5.00 | 1.35 |
| CO$_2$/IPA = 80/20 | | 5.91 | 7.93 | 3.22 | 4.67 | 1.46 |
| CO$_2$/MeCN = 80/20 | | 7.13 | 9.27 | 4.09 | 5.62 | 1.38 |
Example 6
Preparation of Chiral Stationary Phase CSP-3
Chiral Stationary Phase CSP-3 was prepared via the following synthesis route.
[Chem 21]
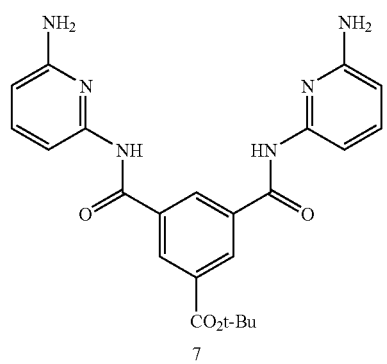
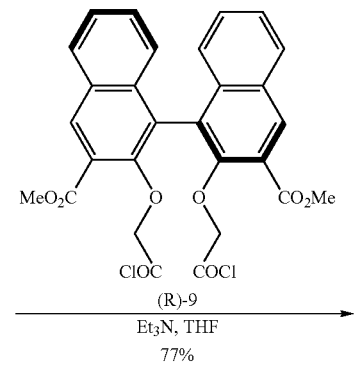
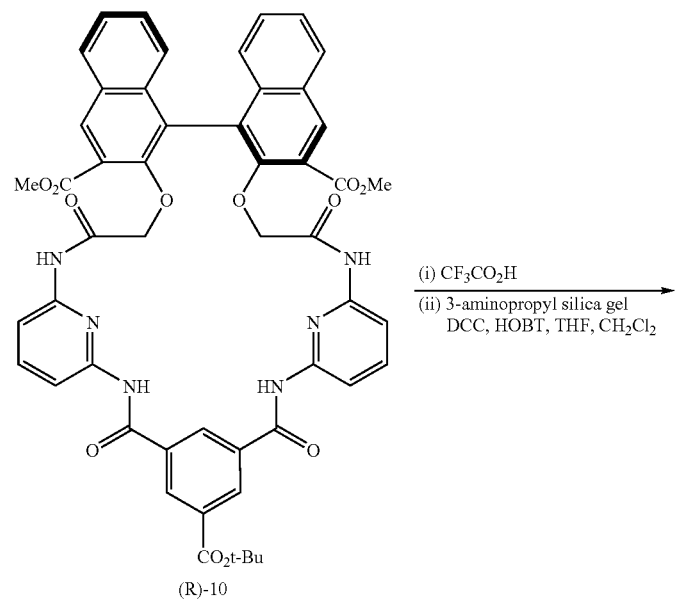

-continued

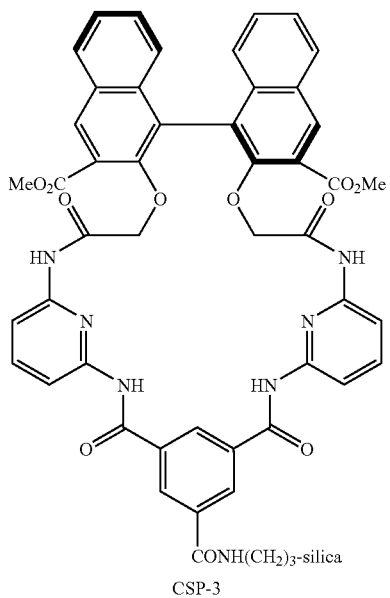
CSP-3

Synthesis of Chiral Macrocycle (R)-10 (Compound (R)-10)

Acid Chloride (R)-9 was synthesized in accordance with T. Ema, D. Tanida, K. Hamada, T. Sakai, Tuning the chiral cavity of macrocyclic receptor for chiral recognition and discrimination. J. Org. Chem., 73(22), 9129-9132 (2008). A solution (120 mL) of Acid Chloride (R)-9 (594 mg, 1.13 mmol) in dry tetrahydrofuran, and a solution (120 mL) of Compound 7 (408 mg, 0.190 mmol) and triethylamine (0.26 mL, 1.9 mmol) in dry tetrahydrofuran were dropped to dry tetrahydrofuran (70 mL) at room temperature at the same rate over 3.5 hours. The resultant mixture was stirred for an additional 12 hours, and then a volatile substance was removed from the mixture with an evaporator. The resultant solid residue was dissolved in methylene chloride, and then the solution was washed with saturated baking soda water (40 mL) and dried with sodium sulfate. After that, the dried product was concentrated under reduced pressure. As a result, a solid product was obtained. The resultant product was purified by silica gel column chromatography (methylene chloride/tetrahydrofuran (methylene chloride:tetrahydrofuran (volume ratio)=20:1)). As a result, Compound (R)-10 as a white solid was obtained (654 mg, 77% yield). Spectrum data on Compound (R)-10 thus obtained is shown below.

Spectrum Data
mp 266° C. (dec)
$[\alpha]^{26}_D$+145 (c 1.01, $CHCl_3$)
$^1$H NMR ($CDCl_3$, 600 MHz) 1.63 (s, 9H), 3.65 (d, J=14.7 Hz, 2H), 3.90 (s, 6H), 4.16 (d, J=14.7 Hz, 2H), 7.18 (d, J=8.1 Hz, 2H), 7.48 (dt, J=1.4, 8.1 Hz, 2H), 7.57 (dt, J=1.4, 8.1 Hz, 2H), 7.78 (t, J=7.9 Hz, 2H), 7.93 (d, J=7.9 Hz, 2H), 8.04 (d, J=8.1 Hz, 2H), 8.13 (d, J=7.9 Hz, 2H), 8.67 (br s, 1H), 8.74 (s, 2H), 8.87 (d, J=1.8 Hz, 2H), 9.03 (br s, 2H), 9.16 (br s, 2H)
$^{13}$C NMR ($CDCl_3$, 150 MHz) 28.1, 52.8, 73.1, 82.4, 109.6, 110.0, 122.8, 125.1, 126.5, 126.8, 126.9, 129.85, 129.94, 130.1, 133.3, 134.1, 134.8, 135.4, 135.5, 141.3, 148.8, 149.5, 151.9, 162.9, 163.8, 165.7, 166.7
IR (KBr) 3393, 2976, 1705, 1585, 1522, 1452, 1302, 1244, 1155, 1076, 800 $cm^{-1}$

[Preparation of Chiral Stationary Phase (CSP-3)]

A solution of Compound (R)-10 (1.15 g, 1.24 mmol) in trifluoroacetic acid (3.1 mL, 40 mmol) was stirred at room temperature under a nitrogen atmosphere for 7.5 hours. The solvent was removed from the resultant mixed liquid by distillation, and then the resultant solid product was dried in a vacuum. As a result, a carboxylic acid of Compound (R)-10 in which the t-butyl group of Compound (R)-10 was substituted with hydrogen was obtained. A mixed solution of dry methylene chloride (5 mL) and dry tetrahydrofuran (6 mL) in which the carboxylic acid of Compound (R)-10 (1.08 g, 1.24 mmol) was dissolved, DCC (405 mg, 1.96 mmol), and HOBT (257 mg, 1.90 mmol) were added to a 3-aminopropyl silica gel (2.47 g) left standing to cool under nitrogen after having been dried in a vacuum at 150° C. for 4 hours. After the resultant slurry had been stirred with a mechanical stirrer at room temperature for 48 hours, DCC (407 mg, 1.97 mmol), HOBT (256 mg, 1.89 mmol), and acetic acid (0.20 mL, 3.5 mmol) were added to the slurry, and then the mixture was stirred for an additional 24 hours. A silica gel obtained by filtrating the resultant slurry was washed with tetrahydrofuran, methylene chloride, ethanol, and hot ethanol in the stated order, and was then dried in a vacuum. As a result, CSP-3 as a white powder was obtained.

Example 7

Preparation of Chiral Stationary Phase CSP-4

Chiral Stationary Phase CSP-4 was prepared via the following synthesis route.

[Chem 22]

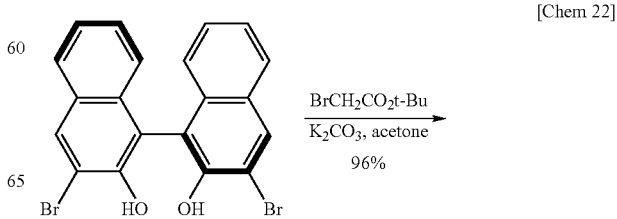

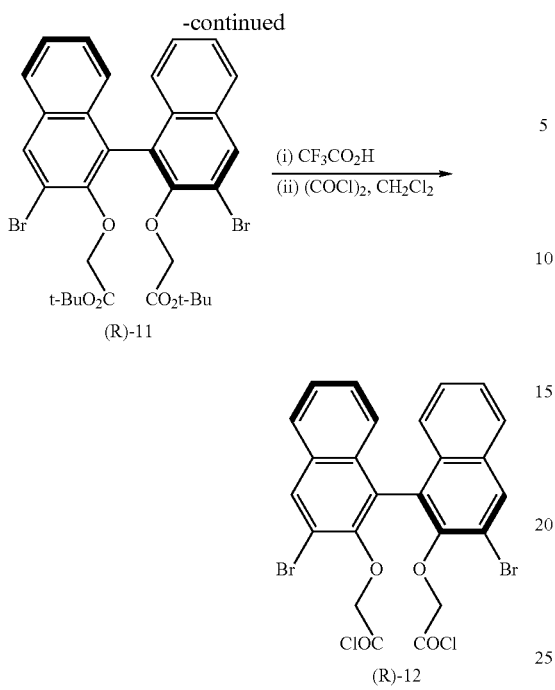

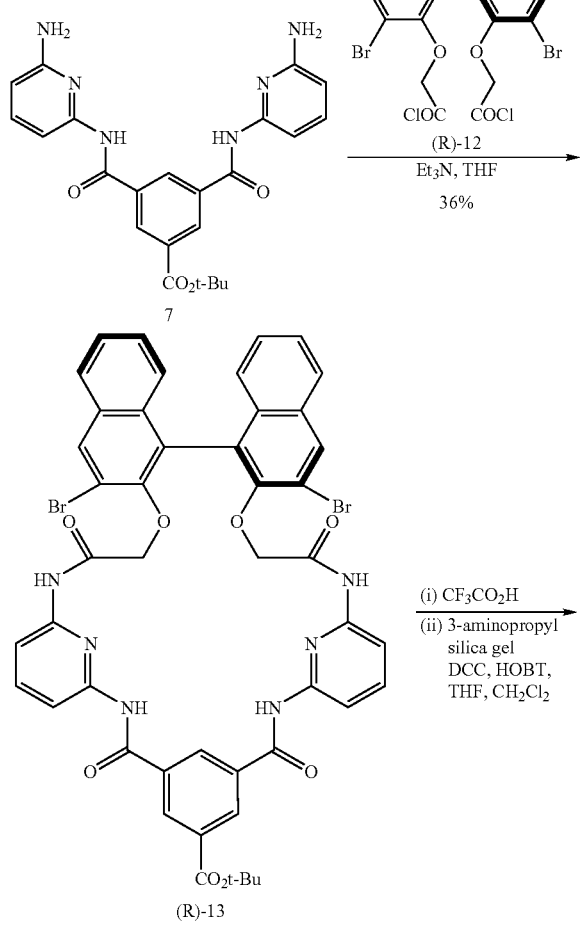

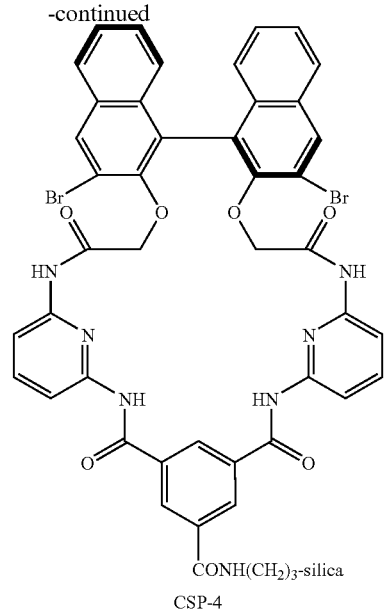

CSP-4

Synthesis of (R)-2,2'-Bis[(tert-butoxycarbonyl)methoxy]-3,3'-dibromo-1,1'-binaphthyl (Compound (R)-11)

An acetone mixed solution (15 mL) containing (R)-3,3'-dibromo-1,1'-bi-2-naphthol (433 mg, 0.974 mmol), bromoacetic acid t-butyl ester (0.35 mL, 2.4 mmol), and potassium carbonate (337 mg, 2.44 mmol) was refluxed under heat for 12 hours. The resultant reaction mixture was filtrated, and then the solvent was removed from the resultant filtrate by distillation. As a result, a solid product was obtained. The resultant product was purified by alumina column chromatography (hexane/ethyl acetate (hexane:ethyl acetate (volume ratio)=5:1)). As a result, Compound (R)-11 as a white solid was obtained (628 mg, 96% yield). Spectrum data on Compound (R)-11 thus obtained is shown below.

Spectrum Data
mp 119° C.
$^1$H NMR (CDCl$_3$, 600 MHz) 1.27 (s, 18H), 4.16 (d, J=15.3 Hz, 2H), 4.54 (d, J=15.3 Hz, 2H), 7.02 (d, J=8.0 Hz, 2H), 7.27 (t, J=8.0 Hz, 2H), 7.42 (t, J=8.0 Hz, 2H), 7.80 (d, J=8.0 Hz, 2H), 8.24 (s, 2H)
$^{13}$C NMR (CDCl$_3$, 150 MHz) 27.8, 70.4, 81.5, 117.0, 125.7, 126.1, 126.5, 127.1, 131.6, 132.8, 133.0, 151.3, 167.1
IR (KBr) 3050, 2981, 1757, 1365, 1218, 1147, 1094, 1064, 1023, 748 cm$^{-1}$

Synthesis of Chiral Macrocycle (R)-12 (Compound (R)-12)

A solution of Compound (R)-11 (4.24 g, 6.30 mmol) in trifluoroacetic acid (13 mL, 170 mmol) was stirred at room temperature under a nitrogen atmosphere for 13 hours. The solvent was removed from the resultant mixed liquid by distillation, and then the resultant solid product was dried in a vacuum. As a result, a carboxylic acid of Compound (R)-11 in which the t-butyl group of Compound (R)-11 was substituted with hydrogen was obtained. Oxalyl chloride (4.8 mL, 56 mmol) and dry dimethylformamide (three drops) were added to a suspension (270 mL) of the carboxylic acid (2.70 g, 4.82 mmol) in dry methylene chloride, and then the mixture was stirred at room temperature for 4 hours. A volatile substance was removed from the resultant mixed liquid with an evaporator, and then the resultant solid was dried in a vacuum for 3 hours. The resultant Acid Chloride (R)-12 of Compound (R)-11 was used without any further purification.

A solution (150 mL) of Acid Chloride (R)-12 (2.88 g, 4.82 mmol) in dry tetrahydrofuran, and a solution (150 mL) of Compound 7 (2.04 mg, 4.55 mmol) and triethylamine (1.3 mL, 9.3 mmol) in dry tetrahydrofuran were dropped to dry tetrahydrofuran (200 mL) at room temperature at the same rate over 5 hours. The resultant mixed liquid was stirred for an additional 10 hours, and then a volatile substance was removed from the mixed liquid with an evaporator. The resultant solid residue was dissolved in methylene chloride, and then the resultant solution was washed with saturated saline (100 mL) and dried with sodium sulfate. After that, the dried product was concentrated under reduced pressure. As a result, a solid product was obtained. The resultant product was purified by silica gel column chromatography (methylene chloride/tetrahydrofuran (methylene chloride:tetrahydrofuran (volume ratio)=20:1)). As a result, Compound (R)-13 as a yellow solid was obtained (1.62 g, 36% yield). Spectrum data on Compound (R)-13 thus obtained is shown below.

Spectrum Data $^1$H NMR (CDCl$_3$, 500 MHz) 1.63 (s, 9H), 3.75 (d, J=15.0 Hz, 2H), 4.27 (d, J=15.0 Hz, 2H), 7.13 (d, J=8.0 Hz, 2H), 7.40 (t, J=8.0 Hz, 2H), 7.54 (t, J=8.0 Hz, 2H), 7.78 (t, J=8.3 Hz, 2H), 7.88-7.92 (m, 4H), 8.14 (d, J=8.0 Hz, 2H), 8.33 (s, 2H), 8.43 (br s, 1H), 8.86 (s, 2H), 8.88 (s, 2H), 8.98 (br s, 2H)

$^{13}$C NMR (CDCl$_3$, 150 MHz) 28.0, 71.8, 82.3, 109.7, 109.9, 116.0, 125.3, 126.7, 127.08, 127.13, 127.7, 128.0, 131.9, 132.4, 133.2, 133.9, 134.0, 134.4, 141.2, 148.5, 149.59, 149.61, 163.3, 163.6, 165.9

[Preparation of Chiral Stationary Phase (CSP-4)]

A solution of Compound (R)-13 (1.51 g, 1.56 mmol) in trifluoroacetic acid (3.5 mL, 45 mmol) was stirred at room temperature under a nitrogen atmosphere for 15 hours. The solvent was removed from the resultant mixed liquid by distillation, and then the resultant solid product was dried in a vacuum. As a result, a carboxylic acid of Compound (R)-13 in which the t-butyl group of Compound (R)-13 was substituted with hydrogen was obtained. A mixed solution of dry tetrahydrofuran (10 mL) and dry methylene chloride (10 mL) in which the carboxylic acid of Compound (R)-13 (1.36 g, 1.48 mmol) was dissolved, DCC (463 mg, 2.24 mmol), and HOBT (303 mg, 2.2 mmol) were added to a 3-aminopropyl silica gel (2.96 g) left standing to cool under nitrogen after having been dried in a vacuum at 150° C. for 4 hours. After the resultant slurry had been stirred with a mechanical stirrer at room temperature for 12 hours, DCC (488 mg, 2.17 mmol) and HOBT (118 mg, 0.871 mmol) were added to the slurry, and then the mixture was stirred for an additional 25.5 hours. A silica gel obtained by filtrating the resultant slurry was washed with tetrahydrofuran, methylene chloride, ethanol, and hot ethanol in the stated order, and was then dried in a vacuum. As a result, a modified silica gel as a white powder was obtained. After that, 1,1,1,3,3,3-hexamethyldisilazane (HMDS) (1.4 mL, 6.7 mmol) was added to a suspension (20 mL) of the resultant silica gel (3.30 g) in dry toluene, and then the mixture was stirred with a mechanical stirrer at room temperature under a nitrogen atmosphere for 2 hours. A silica gel obtained by filtrating the resultant slurry was washed with tetrahydrofuran, and was then dried in a vacuum. As a result, CSP-4 as a white powder was obtained.

Example 8

Preparation of Chiral Stationary Phase CSP-5

Chiral Stationary Phase CSP-5 was prepared via the following synthesis route.

[Chem 23]

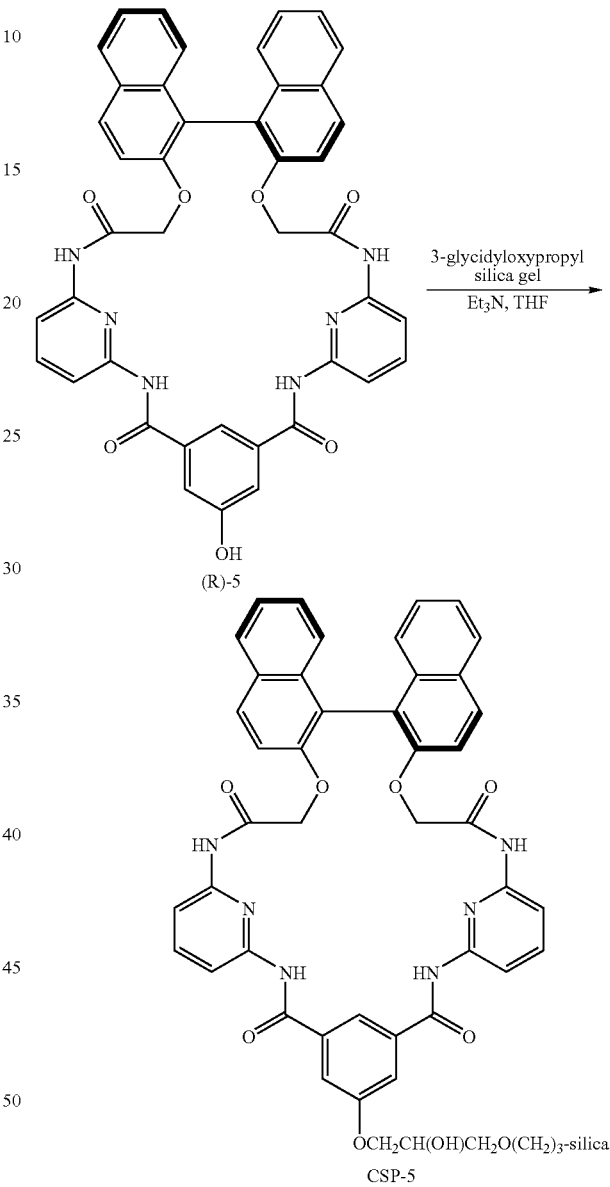

[Preparation of Chiral Stationary Phase (CSP-5)]

Compound (R)-5 (1.46 g, 2.00 mmol) and triethylamine (0.28 mL, 2.0 mmol) were added to a suspension (20 mL) of a 3-glycidyloxypropyl silica gel (2.95 g) that had been dried in a vacuum at room temperature in dry tetrahydrofuran, and then the mixture was refluxed under heat with a mechanical stirrer under a nitrogen atmosphere for 43.5 hours. A silica gel obtained by filtrating the resultant slurry was washed with tetrahydrofuran, acetone, ethanol, and diethyl ether in the stated order, and was then dried in a vacuum. As a result, a modified silica gel as a white powder was obtained. HMDS (1.8 mL, 8.5 mmol) was added to a suspension (20 mL) of the resultant silica gel (3.27 g) in dry toluene, and then the mixture was stirred with a mechanical stirrer at room temperature for 2 hours. A silica gel obtained by filtrating the resultant slurry was washed with toluene, tetrahydrofuran, and diethyl ether in the stated order, and was then dried in a vacuum. As a result, CSP-5 as a white powder was obtained.

It should be noted that a 3-glycidyloxypropyl silica gel obtained by heating commercially available 3-glycidyloxypropyl(dimethoxy)methylsilane (Tokyo Chemical Industry Co., Ltd.) and a silica gel (Wako Pure Chemical Industries, Ltd., Wakosil 5SIL) by an ordinary method in toluene was used as the 3-glycidyloxypropyl silica gel.

Example 9

Preparation of Chiral Stationary Phase CSP-6

Chiral Stationary Phase CSP-6 was prepared via the following synthesis route.

[Chem 24]

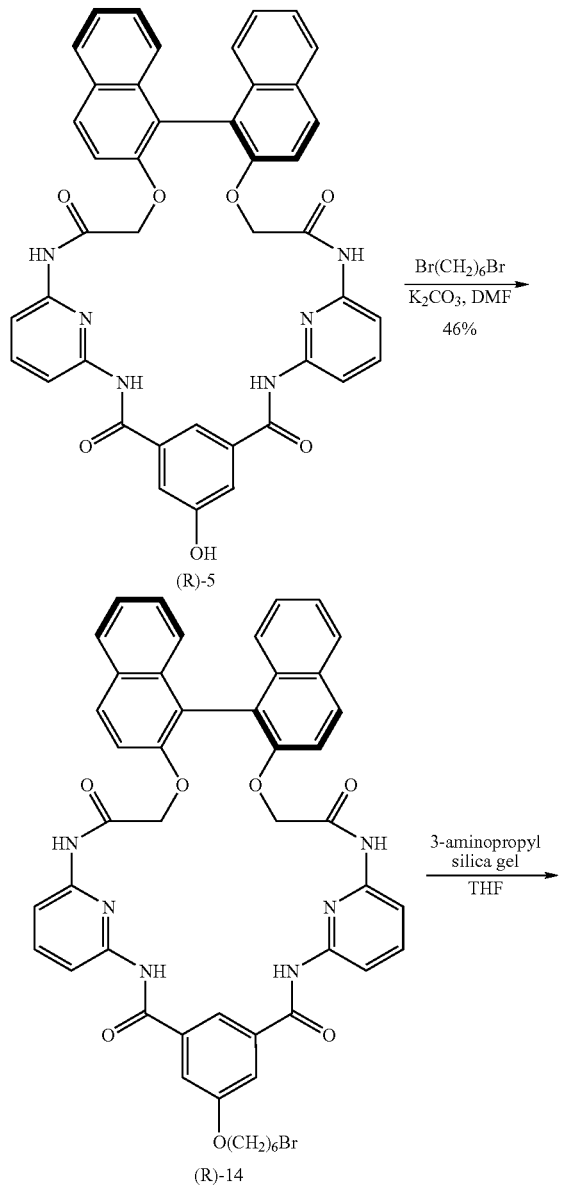

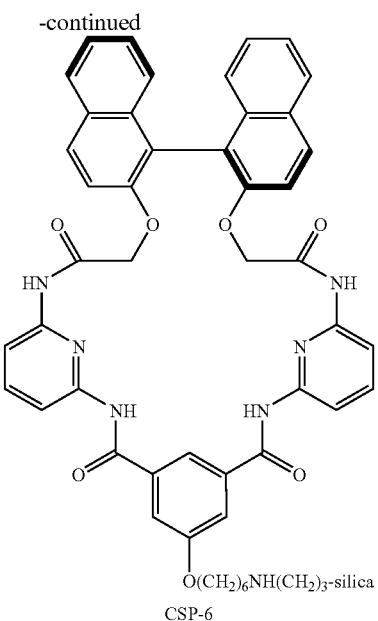

Synthesis of Chiral Macrocycle (R)-14 (Compound (R)-14)

A dry dimethylformamide mixed solution (10 mL) containing Compound (R)-5 (2.19 g, 3.00 mmol), 1,6-dibromohexane (4.5 mL, 30 mmol), and potassium carbonate (0.620 mg, 4.49 mmol) was stirred under a nitrogen atmosphere at 70° C. for 47 hours. The resultant reaction mixture was filtrated, and then the solvent was removed from the resultant filtrate by distillation. As a result, a solid product was obtained. The resultant product was purified by silica gel column chromatography (methylene chloride/tetrahydrofuran (methylene chloride:tetrahydrofuran (volume ratio)=30:1)). As a result, Compound (R)-14 as a white solid was obtained (1.23 g, 46% yield). Spectrum data on Compound (R)-14 thus obtained is shown below.

Spectrum Data $^1$H NMR (CDCl$_3$, 600 MHz) 1.53 (quint, J=3.5 Hz, 4H), 1.84-1.93 (m, 4H), 3.43 (t, J=6.5 Hz, 2H), 4.10 (t, J=6.5 Hz, 2H), 4.28 (d, J=16.0 Hz, 2H), 4.52 (d, J=16.0 Hz, 2H), 7.30 (d, J=7.9 Hz, 2H), 7.39 (dt, J=1.2, 7.9 Hz, 2H), 7.44 (d, J=9.0 Hz, 2H), 7.47 (dt, J=1.2, 7.9 Hz, 2H), 7.71 (s, 1H), 7.79-7.82 (m, 4H), 7.93 (d, J=7.9 Hz, 2H), 7.99 (d, J=8.0 Hz, 2H), 8.03 (d, J=9.0 Hz, 2H), 8.14 (d, J=8.0 Hz, 2H), 8.70 (br s, 2H), 8.78 (br s, 2H)

$^{13}$C NMR (CDCl$_3$, 150 MHz) 25.1, 27.8, 28.8, 32.5, 33.7, 68.3, 72.9, 109.7, 110.0, 115.0, 118.4, 119.1, 122.8, 125.2, 125.5, 127.2, 128.3, 130.8, 130.9, 133.4, 134.9, 140.9, 148.3, 149.4, 154.0, 160.4, 163.3, 167.3

[Preparation of Chiral Stationary Phase (CSP-6)]

Compound (R)-14 (1.09 g, 1.22 mmol) was added to a suspension (20 mL) of a 3-aminopropyl silica gel (2.90 g) that had been dried in a vacuum at room temperature in dry tetrahydrofuran, and then the mixture was refluxed under heat with a mechanical stirrer under a nitrogen atmosphere for 42 hours. A silica gel obtained by filtrating the resultant slurry was washed with 50% ethanol aqueous solution, ethanol, tetrahydrofuran, and diethyl ether in the stated order, and was then dried in a vacuum. As a result, a modified silica gel as a white powder was obtained. HMDS (1.8 mL, 8.5 mmol) was added to a suspension (20 mL) of the resultant silica gel (3.01 g) in dry toluene, and then the mixture was stirred with a mechanical stirrer at room temperature for 2.5 hours. A silica gel obtained by filtrating the resultant slurry was washed with toluene, tetrahydrofuran, and diethyl ether in the stated order, and was then dried in a vacuum. As a result, CSP-6 as a white powder was obtained.

Example 10

Preparation of Chiral Stationary Phase CSP-7

Chiral Stationary Phase CSP-7 was prepared via the following synthesis route.

[Chem 25]

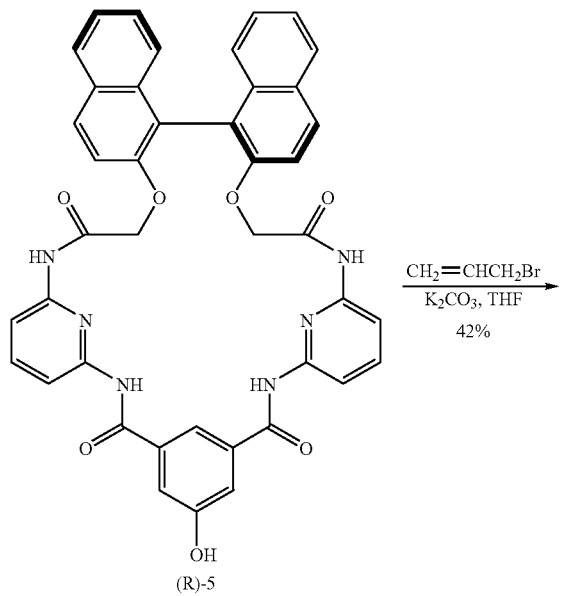

(R)-5

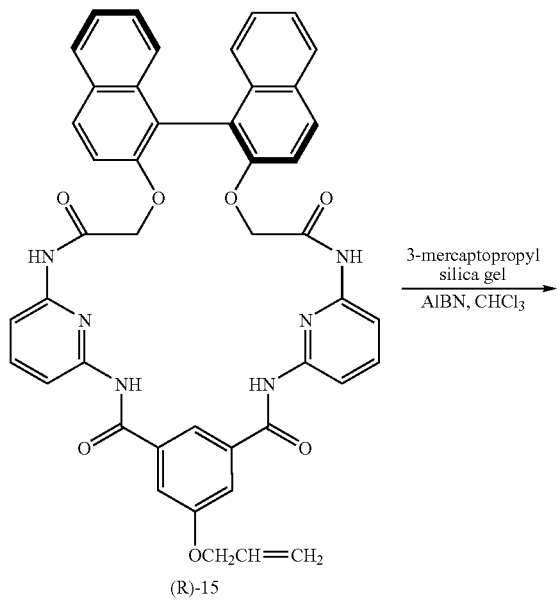

(R)-15

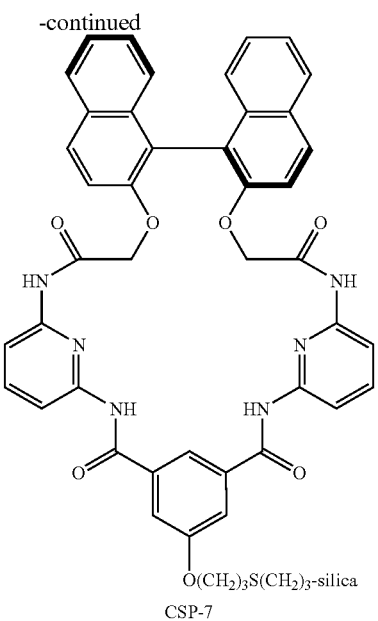

CSP-7

Synthesis of Chiral Macrocycle (R)-15 (Compound (R)-15)

A dry tetrahydrofuran mixed solution (25 mL) containing Compound (R)-5 (1.80 g, 2.46 mmol), allyl bromide (0.26 mL, 3.0 mmol), and potassium carbonate (0.510 g, 3.69 mmol) was refluxed under heat under a nitrogen atmosphere for 2 hours. After that, allyl bromide (0.26 mL, 3.0 mmol) and dry tetrahydrofuran (5 mL) were added to the reaction mixture, and then the mixture was refluxed under heat for an additional 16.5 hours. The resultant reaction mixture was filtered, and then the solvent was removed from the resultant filtrate by distillation. As a result, a solid product was obtained. The resultant product was purified by silica gel column chromatography (methylene chloride/tetrahydrofuran (methylene chloride:tetrahydrofuran (volume ratio)=20: 1)). As a result, Compound (R)-15 as a white solid was obtained (0.791 g, 42% yield). Spectrum data on Compound (R)-15 thus obtained is shown below.

Spectrum Data mp 258° C. (dec)

$^1$H NMR (CDCl$_3$, 600 MHz) 4.28 (d, J=16.0 Hz, 2H), 4.52 (d, J=16.0 Hz, 2H), 4.68 (td, J=1.5, 5.0 Hz, 2H), 5.34 (qd, J=1.5, 10.5 Hz, 1H), 5.46 (qd, J=1.5, 17.0 Hz, 1H), 6.02-6.10 (m, 1H), 7.30 (d, J=8.0 Hz, 2H), 7.38 (dt, J=1.0, 8.0 Hz, 2H), 7.44 (d, J=9.0 Hz, 2H), 7.48 (dt, J=1.0, 8.0 Hz, 2H), 7.81-7.85 (m, 5H), 7.93 (d, J=8.0 Hz, 2H), 7.99 (d, J=8.0 Hz, 2H), 8.03 (d, J=9.0 Hz, 2H), 8.15 (d, J=8.0 Hz, 2H), 8.81 (br s, 4H)

$^{13}$C NMR (CDCl$_3$, 150 MHz) 69.2, 73.1, 109.8, 110.2, 114.9, 118.4, 119.0, 119.2, 123.0, 125.2, 125.6, 127.3, 128.4, 130.9, 131.0, 132.2, 133.5, 135.2, 141.5, 148.4, 149.4, 154.1, 160.2, 163.2, 167.5

IR (KBr) 3393, 3063, 1684, 1585, 1508, 1456, 1313, 1244, 1157, 804 cm$^{-1}$

[Preparation of Chiral Stationary Phase (CSP-7)]

Compound (R)-15 (947 mg, 1.23 mmol) and azobisisobutyronitrile (71 mg, 0.43 mmol) were added to a suspension (20 mL) of a 3-mercaptopropyl silica gel (3.00 g) that had been dried in a vacuum at room temperature in dry chloroform, and then the mixture was refluxed under heat with a mechanical stirrer under a nitrogen atmosphere for 24 hours.

A silica gel obtained by filtrating the resultant slurry was washed with chloroform, methanol, and diethyl ether in the stated order, and was then dried in a vacuum. As a result, a modified silica gel as a white powder was obtained. HMDS (1.8 mL, 8.5 mmol) was added to a suspension (20 mL) of the resultant silica gel (3.29 g) in dry tetrahydrofuran, and then the mixture was stirred with a mechanical stirrer at room temperature for 3 hours. A silica gel obtained by filtrating the resultant slurry was washed with tetrahydrofuran and diethyl ether in the stated order, and was then dried in a vacuum. As a result, CSP-7 as a white powder was obtained.

It should be noted that a 3-mercaptopropyl silica gel obtained by heating commercially available (3-mercaptopropyl)trimethoxysilane (Tokyo Chemical Industry Co., Ltd.) and a silica gel (Wako Pure Chemical Industries, Ltd., Wakosil 5SIL) by an ordinary method in toluene was used as the 3-mercaptopropyl silica gel.

Example 11

Production of Column for HPLC With CSP-3

CSP-3 (3.5 g) was dispersed in methanol, and then a stainless column having a diameter of 0.46 cm and a length of 25 cm was filled with the resultant slurry according to a slurry mode. Thus, a column filled with CSP-3 was produced.

CSP-3 was evaluated for its asymmetry recognition ability with the resultant column under four kinds of evaluation conditions. The racemic bodies of Compounds 1 to 9 were used as samples for evaluation. The following evaluation of the chiral stationary phase for its asymmetry recognition ability is described for the respective evaluation conditions.

[Evaluation (1)]

The evaluation for the asymmetry recognition ability was performed with four kinds of samples for evaluation (Compound Nos.: 3, 4, 5, and 6) under the following conditions by HPLC. Table 11 shows the results of the evaluation. In addition, FIGS. 56 to 59 illustrate the chromatograms of the respective samples for evaluation.

(Evaluation Conditions 1)
Moving phase: hexane/2-propanol=9/1(v/v)
Flow rate: 1.0 mL/min.
Temperature: 25° C.
Detection: UV 254 nm (225 nm for Sample 5 alone)

TABLE 11

| Sample | 3 | 4 | 5 | 6 |
|---|---|---|---|---|
| t0 | 3.02 | | | |
| t1 | 20.95 | 9.59 | 7.28 | 23.42 |
| t2 | 36.61 | 10.06 | 7.88 | 35.04 |
| k1' | 5.94 | 2.18 | 1.41 | 6.75 |
| k2' | 11.12 | 2.33 | 1.61 | 10.60 |
| α | 1.87 | 1.07 | 1.14 | 1.57 |

[Evaluation (2)]

The evaluation for the asymmetry recognition ability was performed with five kinds of samples for evaluation (Compound Nos.: 3, 4, 5, 6, and 8) under the following conditions by HPLC. Table 12 shows the results of the evaluation. In addition, FIGS. 60 to 64 illustrate the chromatograms of the respective samples for evaluation.

(Evaluation Conditions 2)
Moving phase: hexane/chloroform mixed solution (composition ratio (v/v) is described in the table)
Flow rate: 1.0 mL/min.
Temperature: 25° C.
Detection: UV 254 nm (225 nm for Sample 5 alone)

TABLE 12

| Sample | 3 | 4 | 5 | 6 | 8 |
|---|---|---|---|---|---|
| Composition | 7/3 | 7/3 | 7/3 | 4/6 | 7/3 |
| t0 | 2.96 | | | | |
| t1 | 13.73 | 4.78 | 3.41 | 5.06 | 12.13 |
| t2 | 27.32 | 4.90 | 3.55 | 6.10 | 14.36 |
| k1' | 3.64 | 0.61 | 0.15 | 0.71 | 3.10 |
| k2' | 8.23 | 0.66 | 0.20 | 1.06 | 3.85 |
| α | 2.26 | 1.07 | 1.31 | 1.50 | 1.24 |

[Evaluation (3)]

Figure 65:
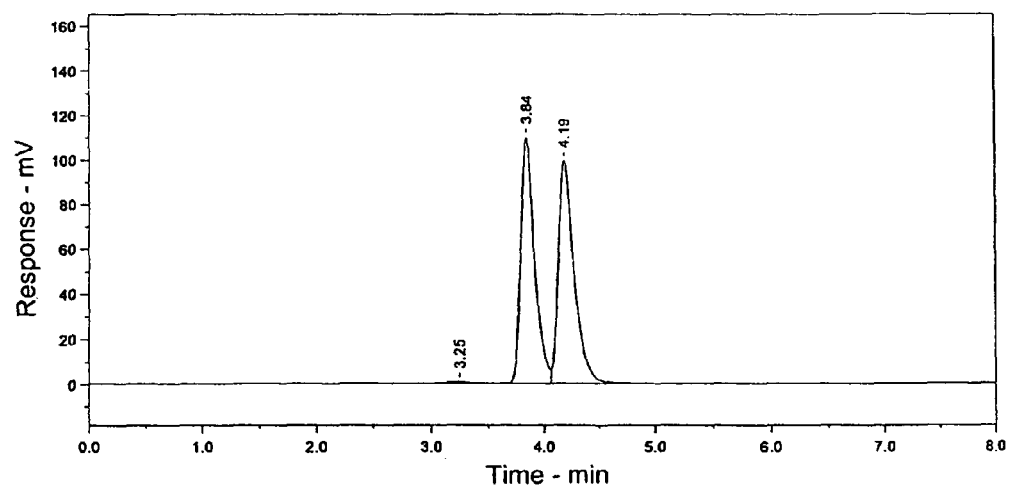
FIG. 65 illustrates a chromatogram of Evaluation Sample 3 in Evaluation 3 of Example 11.
Figure 66:
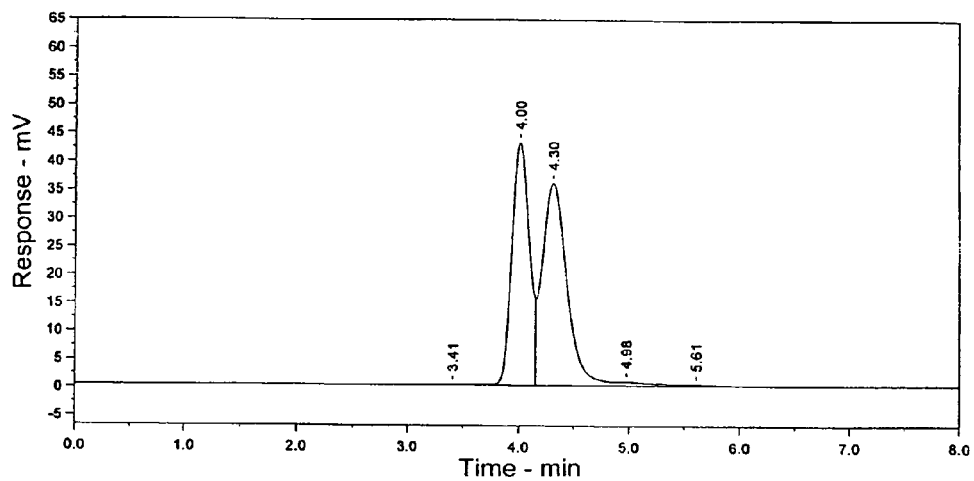
FIG. 66 illustrates a chromatogram of Evaluation Sample 2 in Evaluation 4 of Example 11.
Figure 67:
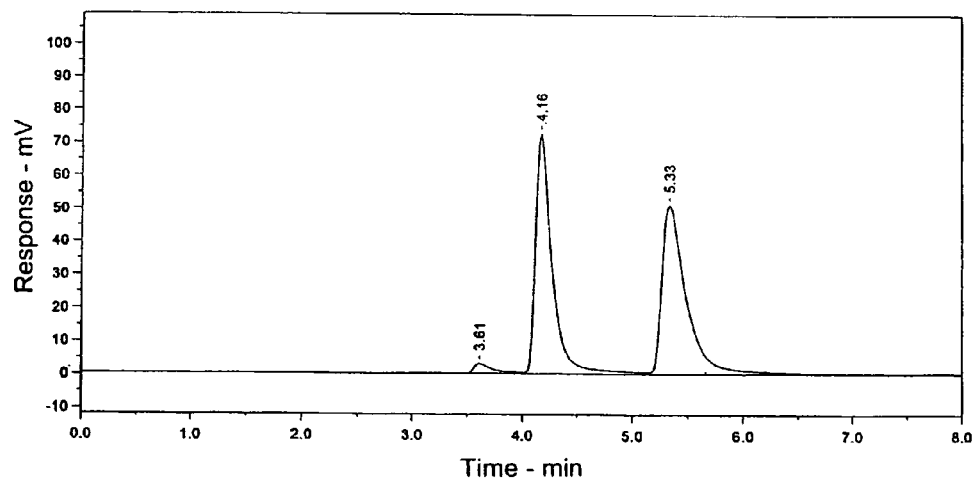
FIG. 67 illustrates a chromatogram of Evaluation Sample 3 in Evaluation 4 of Example 11.
Figure 68:
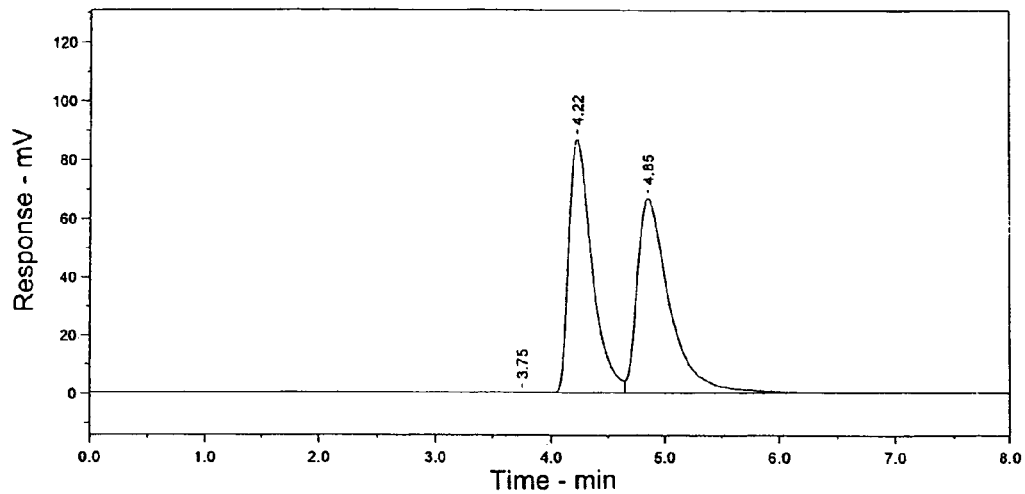
FIG. 68 illustrates a chromatogram of Evaluation Sample 6 in Evaluation 4 of Example 11.
Figure 69:
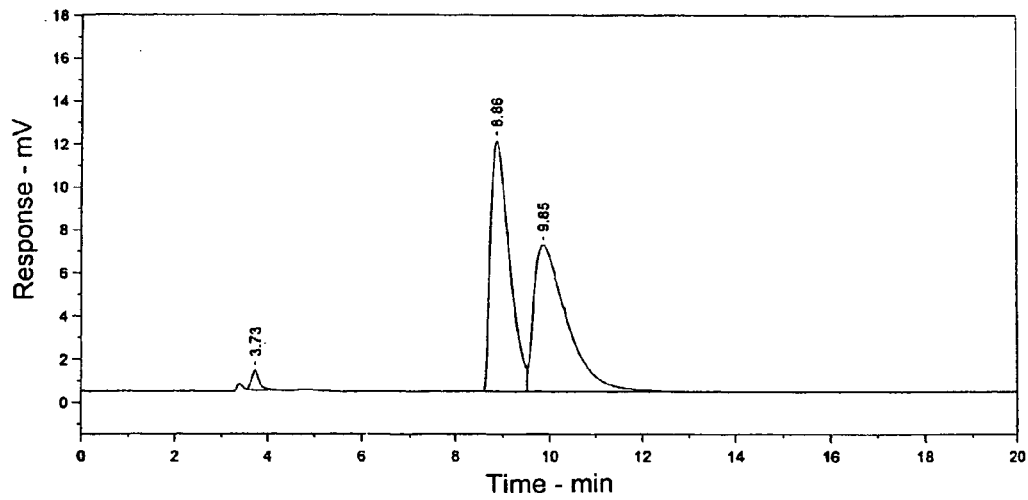
FIG. 69 illustrates a chromatogram of Evaluation Sample 8 in Evaluation 4 of Example 11.
Figure 70:
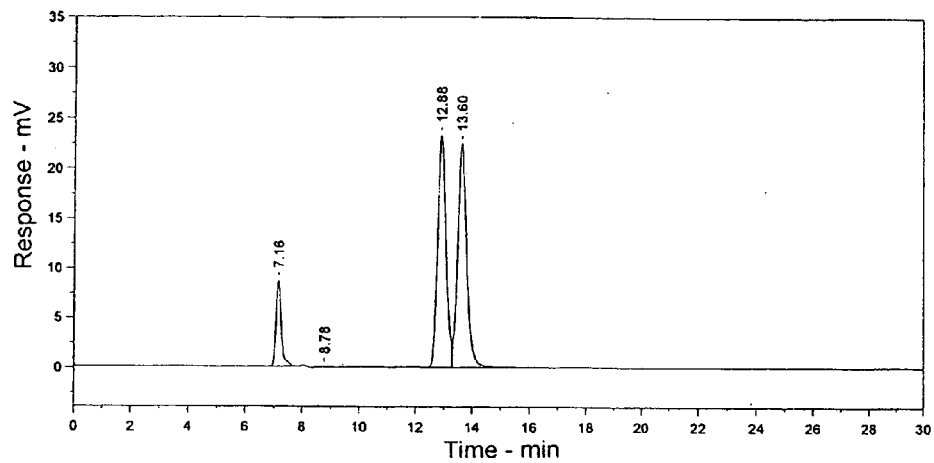
FIG. 70 illustrates a chromatogram of Evaluation Sample 1 in Evaluation 1 of Example 12.
Figure 71:
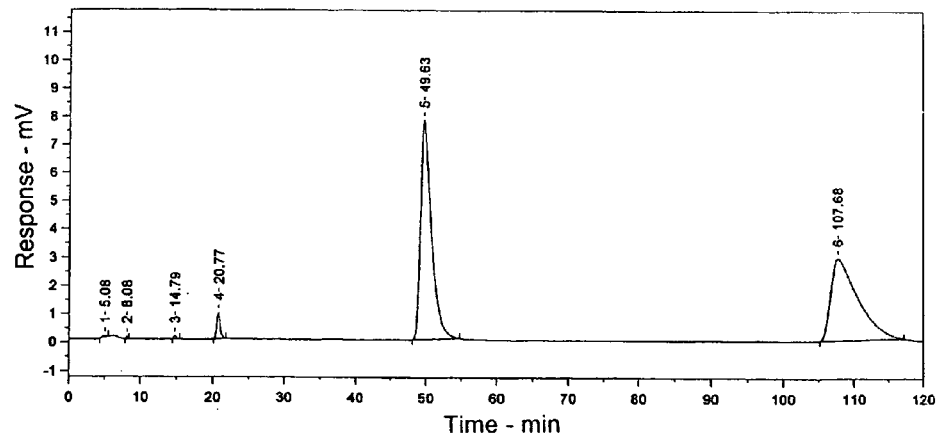
FIG. 71 illustrates a chromatogram of Evaluation Sample 3 in Evaluation 1 of Example 12.
Figure 72:
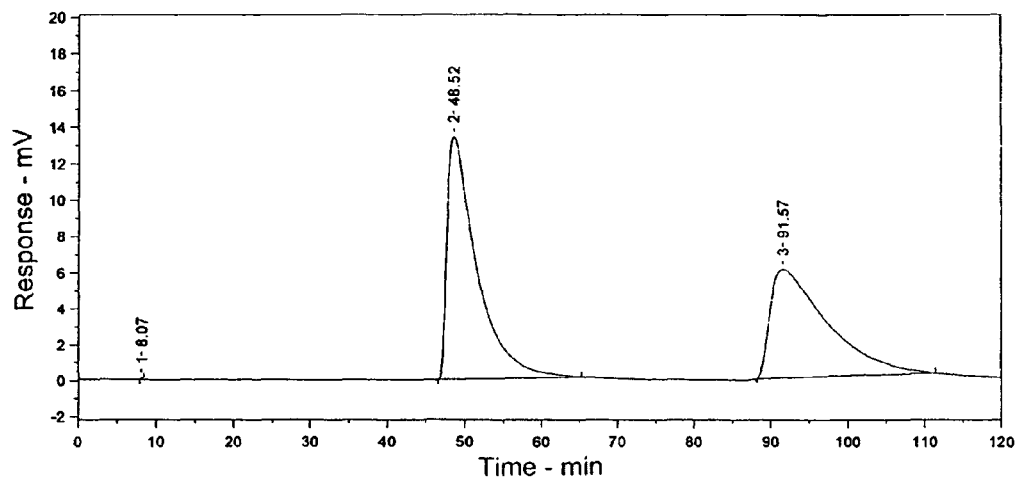
FIG. 72 illustrates a chromatogram of Evaluation Sample 6 in Evaluation 1 of Example 12.
Figure 73:
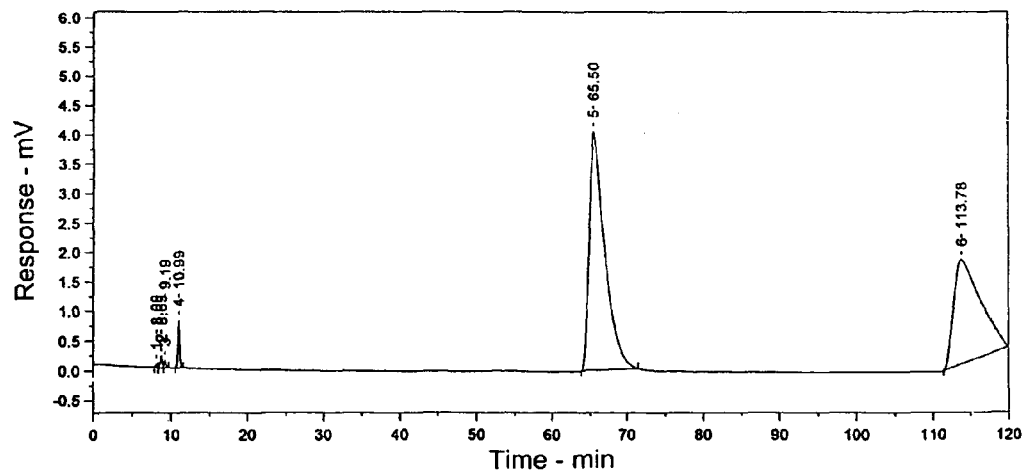
FIG. 73 illustrates a chromatogram of Evaluation Sample 8 in Evaluation 1 of Example 12.

The evaluation for the asymmetry recognition ability was performed with one kind of samples for evaluation (Compound No.: 3) under the following conditions by HPLC. Table 13 shows the results of the evaluation. In addition, FIG. 65 illustrates the chromatograms of the respective samples for evaluation.

(Evaluation Conditions 3)
Moving phase: methanol
Flow rate: 1.0 mL/min.
Temperature: 25° C.
Detection: UV 254 nm

TABLE 13

| Sample | 3 |
|---|---|
| t0 | 3.19 |
| t1 | 3.84 |
| t2 | 4.19 |
| k1' | 0.20 |
| k2' | 0.31 |
| α | 1.54 |

[Evaluation (4)]

The evaluation for the asymmetry recognition ability was performed with four kinds of samples for evaluation (Compound Nos.: 2, 3, 6, and 8) under the following conditions by HPLC. Table 14 shows the results of the evaluation. In addition, FIGS. 66 to 69 illustrate the chromatograms of the respective samples for evaluation.

(Evaluation Conditions 4)
Moving phase: acetonitrile
Flow rate: 1.0 mL/min.
Temperature: 25° C.
Detection: UV 254 nm

TABLE 14

| Sample | 2 | 3 | 6 | 8 |
|---|---|---|---|---|
| t0 | 3.18 | | | |
| t1 | 4.00 | 4.16 | 4.22 | 8.86 |
| t2 | 4.30 | 5.33 | 4.85 | 9.85 |
| k1' | 0.26 | 0.31 | 0.33 | 1.79 |
| k2' | 0.35 | 0.68 | 0.53 | 2.10 |
| α | 1.37 | 2.19 | 1.61 | 1.17 |

Example 12

Production of Column for HPLC With CSP-4

CSP-4 (3.5 g) was dispersed in methanol, and then a stainless column having a diameter of 0.46 cm and a length of 25 cm was filled with the resultant slurry according to a slurry mode. Thus, a column filled with CSP-4 was produced.

CSP-4 was evaluated for its asymmetry recognition ability with the resultant column under the following evaluation conditions. The racemic bodies of Compounds 1 to 9 were used as samples for evaluation.
[Evaluation (1)]
The evaluation for the asymmetry recognition ability was performed with four kinds of samples for evaluation (Compound Nos.: 1, 3, 6, and 8) under the following conditions by HPLC. Table 15 shows the results of the evaluation. In addition, FIGS. 70 to 73 illustrate the chromatograms of the respective samples for evaluation.
(Evaluation Conditions 1)
　Moving phase: hexane/2-propanol=9/1(v/v)
　Flow rate: 0.4 mL/min.
　Temperature: 25° C.
　Detection: UV 254 nm

TABLE 15

| Sample | 1 | 3 | 6 | 8 |
|---|---|---|---|---|
| t0 | 7.16 | | | |
| t1 | 12.88 | 49.63 | 48.52 | 65.50 |
| t2 | 13.60 | 107.68 | 91.57 | 113.78 |
| k1' | 0.80 | 5.93 | 5.78 | 8.15 |
| k2' | 0.90 | 14.04 | 11.79 | 14.89 |
| α | 1.13 | 2.37 | 2.04 | 1.83 |

Example 13

Production of Column for HPLC With CSP-5

CSP-5 (3.5 g) was dispersed in methanol, and then a stainless column having a diameter of 0.46 cm and a length of 25 cm was filled with the resultant slurry according to a slurry mode. Thus, a column filled with CSP-5 was produced.

Figure 74:
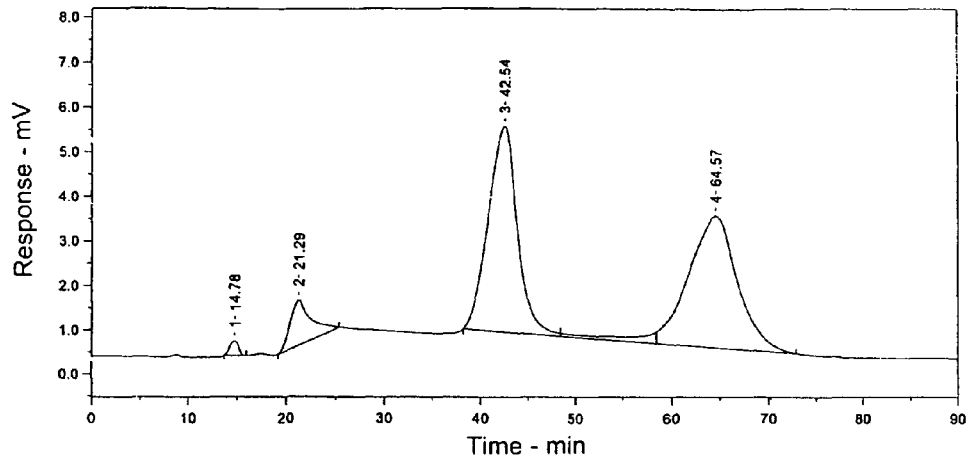
FIG. 74 illustrates a chromatogram of Evaluation Sample 3 in Evaluation 1 of Example 13.
Figure 75:
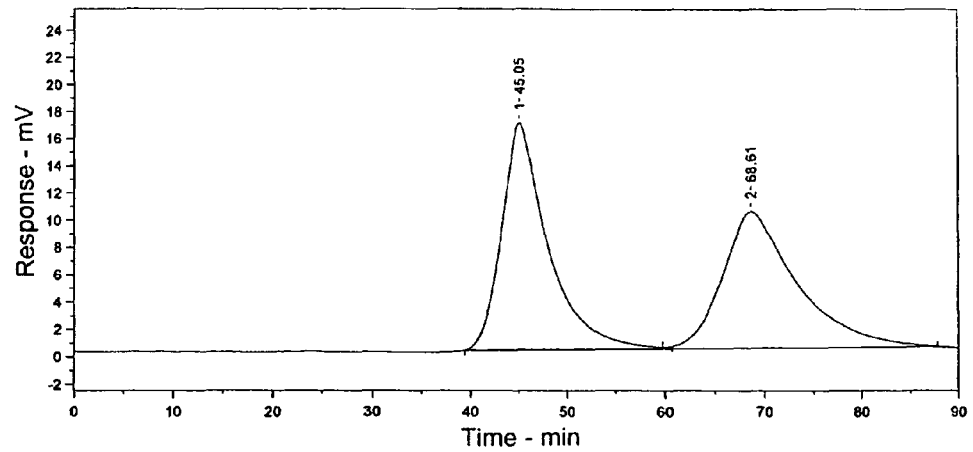
FIG. 75 illustrates a chromatogram of Evaluation Sample 6 in Evaluation 1 of Example 13.
Figure 76:
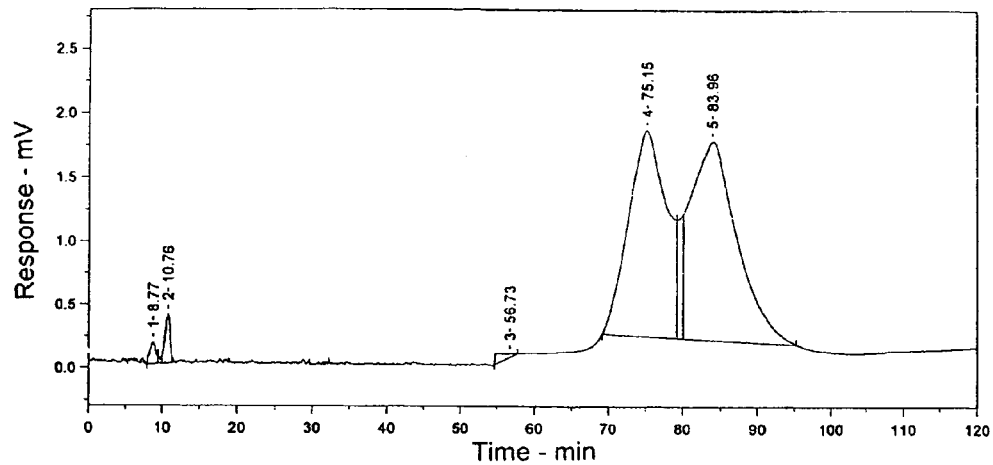
FIG. 76 illustrates a chromatogram of Evaluation Sample 8 in Evaluation 1 of Example 13.
Figure 77:
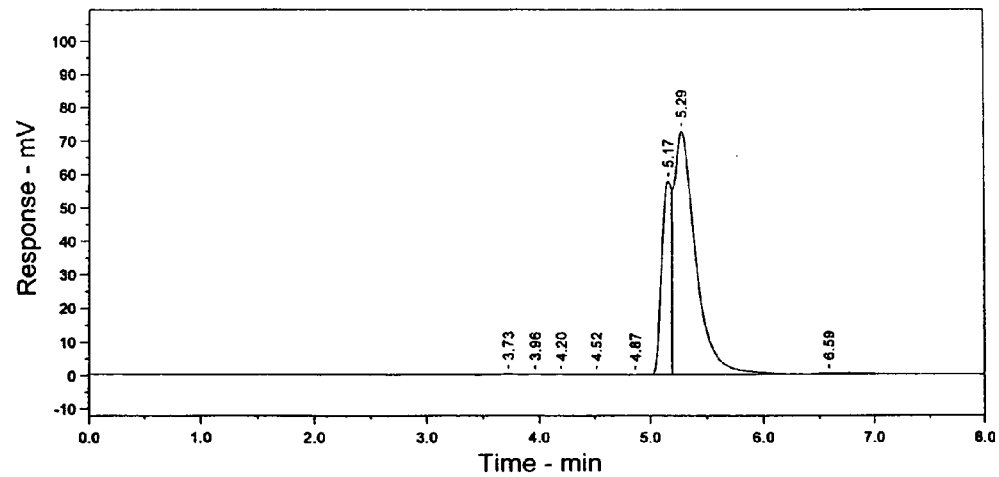
FIG. 77 illustrates a chromatogram of Evaluation Sample 2 in Evaluation 1 of Example 14.
Figure 78:
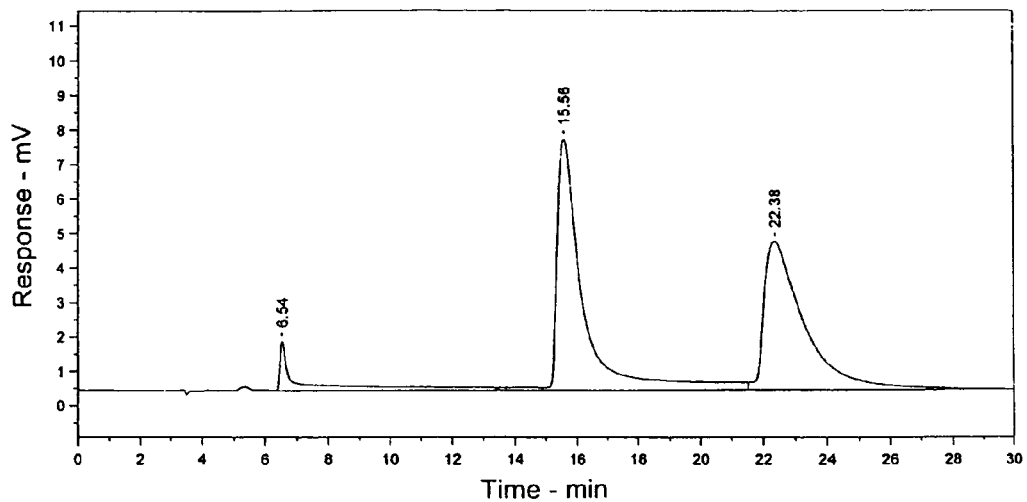
FIG. 78 illustrates a chromatogram of Evaluation Sample 3 in Evaluation 1 of Example 14.
Figure 79:
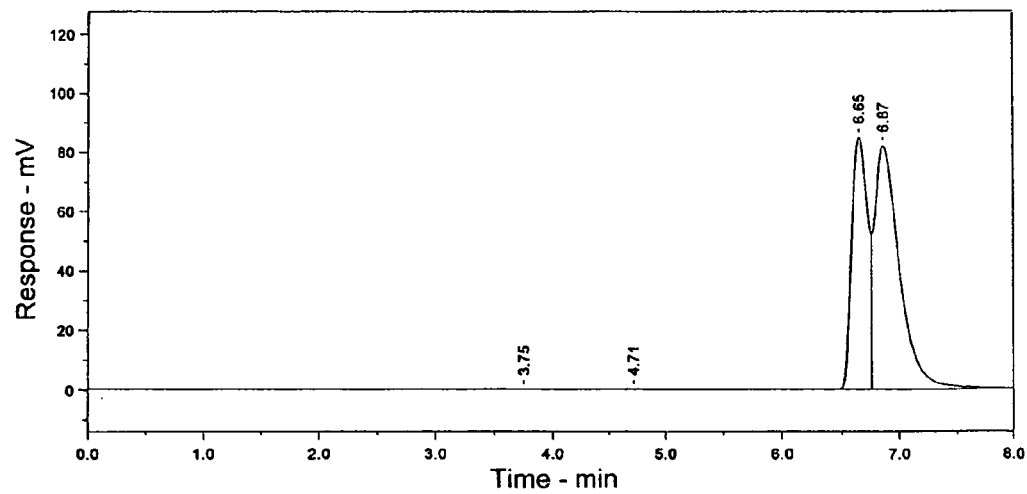
FIG. 79 illustrates a chromatogram of Evaluation Sample 4 in Evaluation 1 of Example 14.
Figure 80:
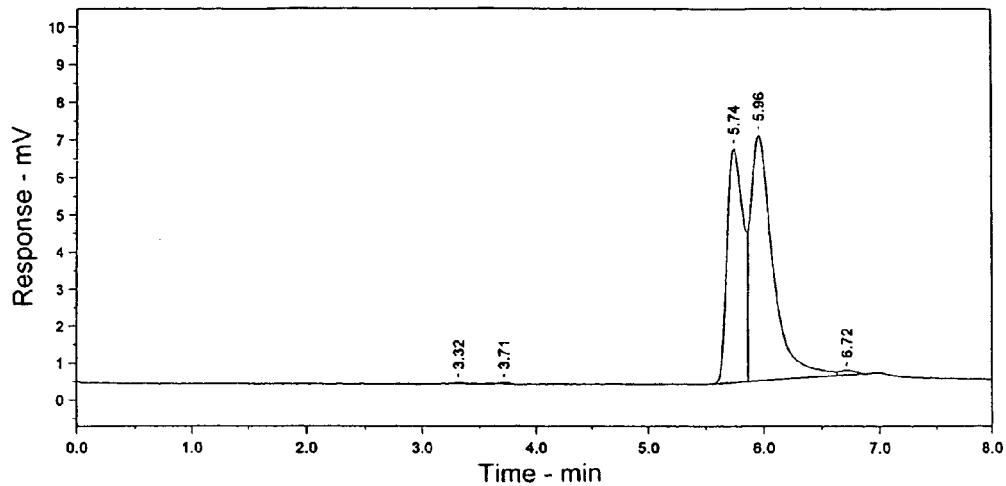
FIG. 80 illustrates a chromatogram of Evaluation Sample 5 in Evaluation 1 of Example 14.
Figure 81:
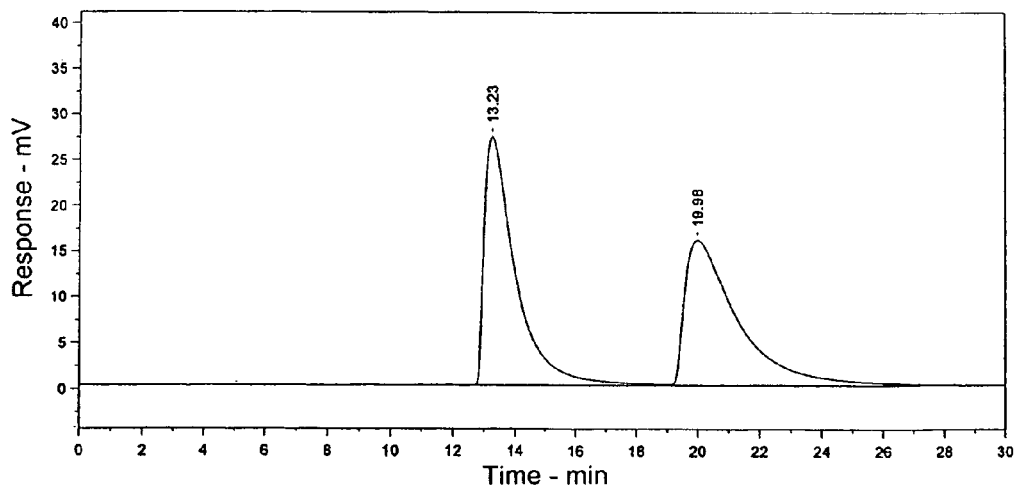
FIG. 81 illustrates a chromatogram of Evaluation Sample 6 in Evaluation 1 of Example 14.
Figure 82:
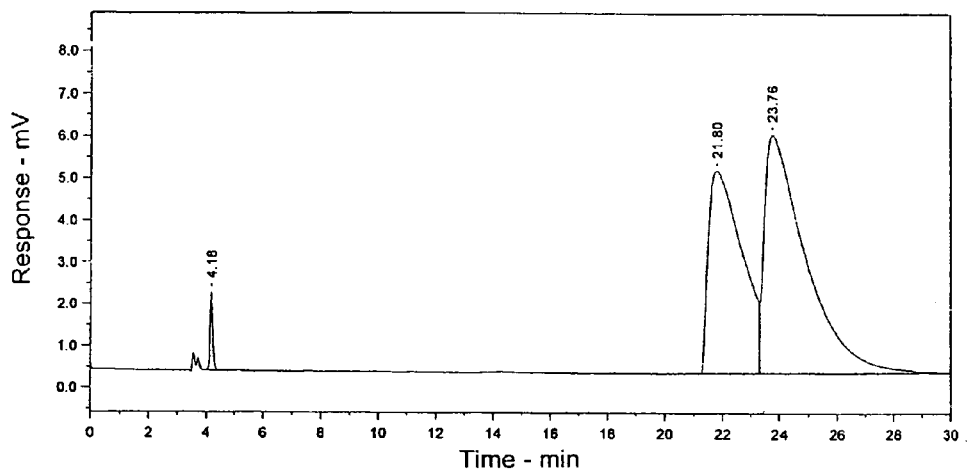
FIG. 82 illustrates a chromatogram of Evaluation Sample 8 in Evaluation 1 of Example 14.
Figure 83:
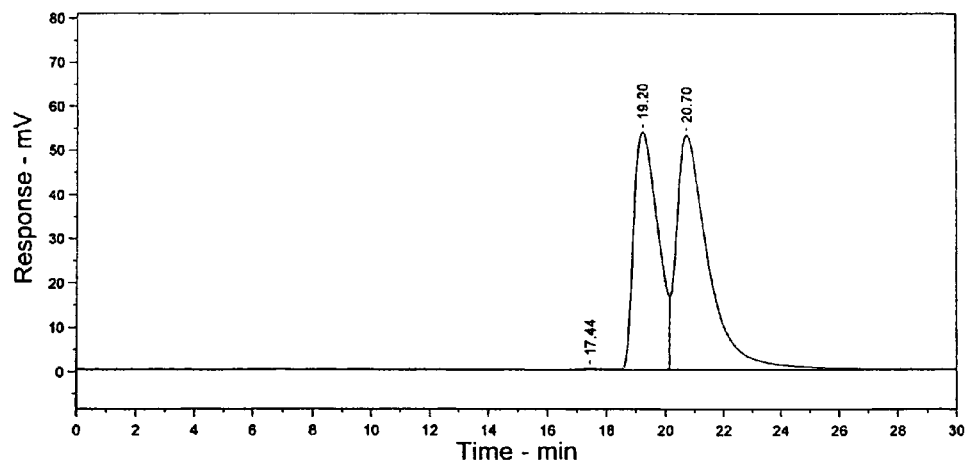
FIG. 83 illustrates a chromatogram of Evaluation Sample 1 in Evaluation 1 of Example 15.
Figure 84:
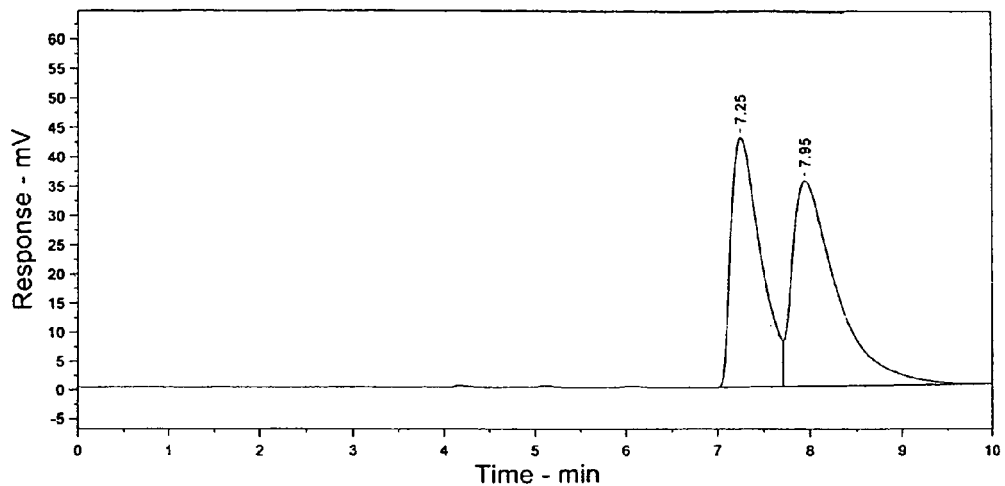
FIG. 84 illustrates a chromatogram of Evaluation Sample 2 in Evaluation 1 of Example 15.
Figure 85:
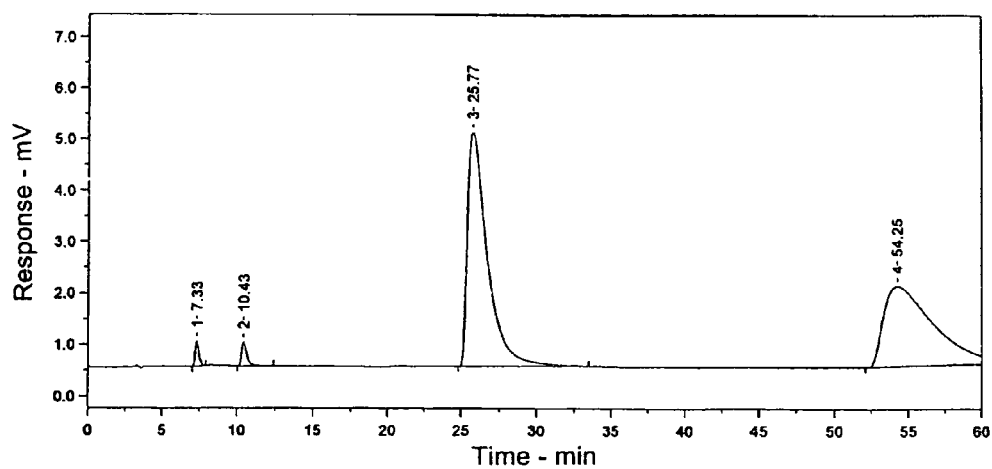
FIG. 85 illustrates a chromatogram of Evaluation Sample 3 in Evaluation 1 of Example 15.
Figure 86:
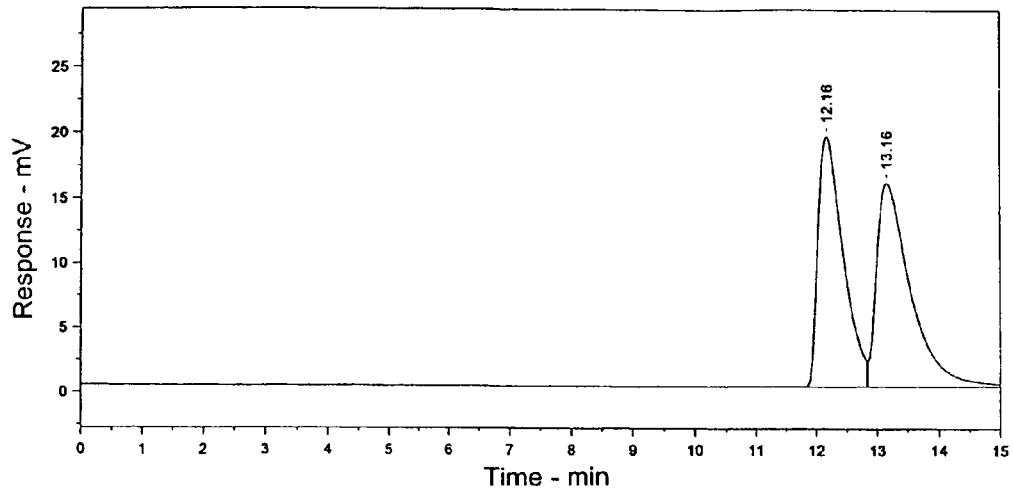
FIG. 86 illustrates a chromatogram of Evaluation Sample 4 in Evaluation 1 of Example 15.
Figure 87:
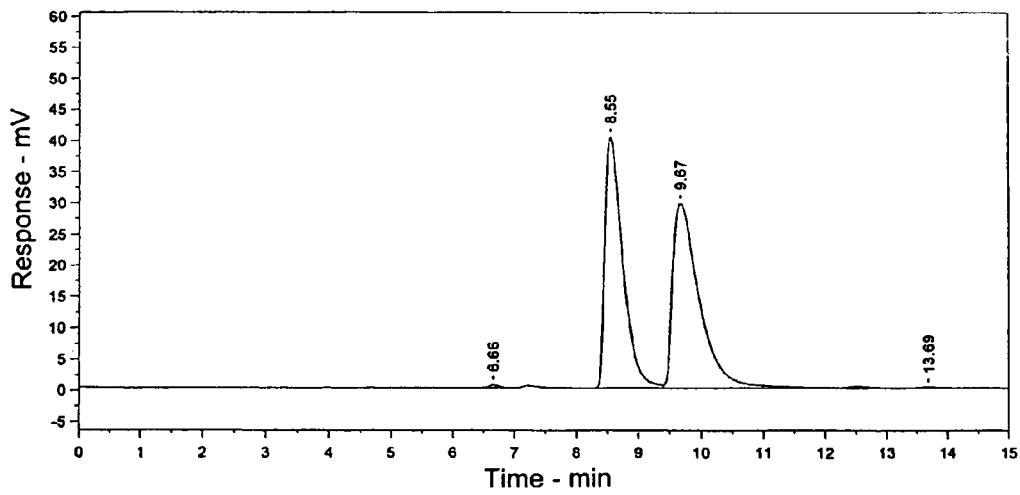
FIG. 87 illustrates a chromatogram of Evaluation Sample 5 in Evaluation 1 of Example 15.
Figure 88:
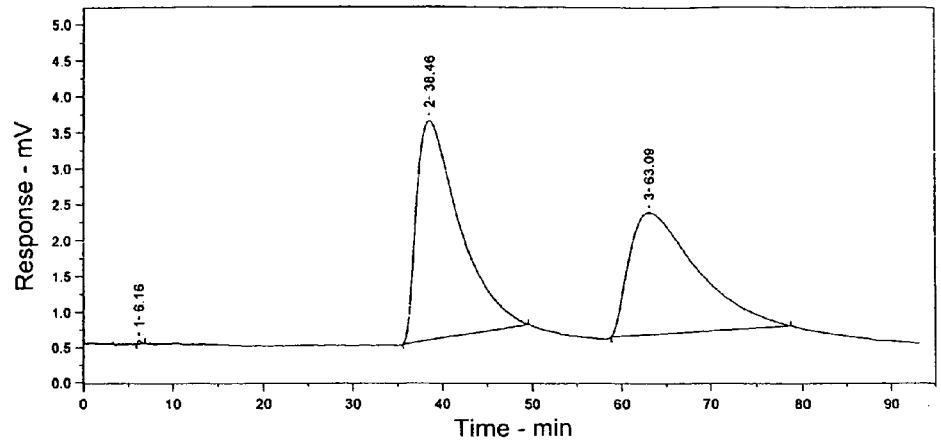
FIG. 88 illustrates a chromatogram of Evaluation Sample 6 in Evaluation 1 of Example 15.
Figure 89:
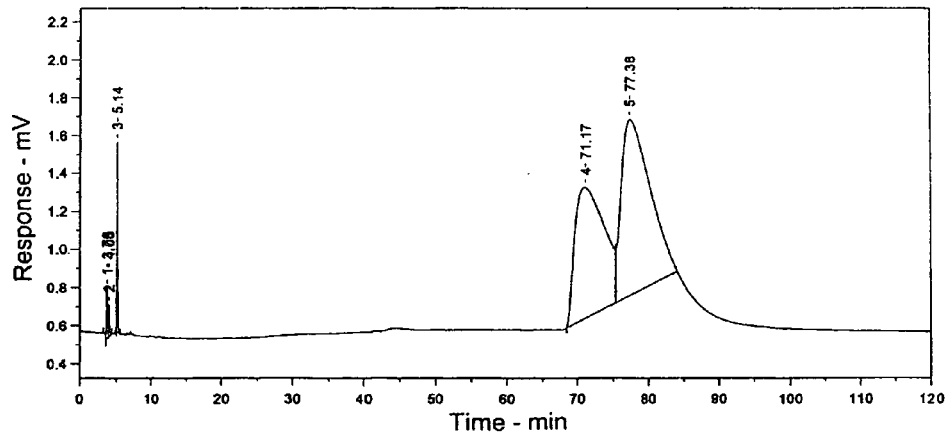
FIG. 89 illustrates a chromatogram of Evaluation Sample 8 in Evaluation 1 of Example 15.
Figure 90:
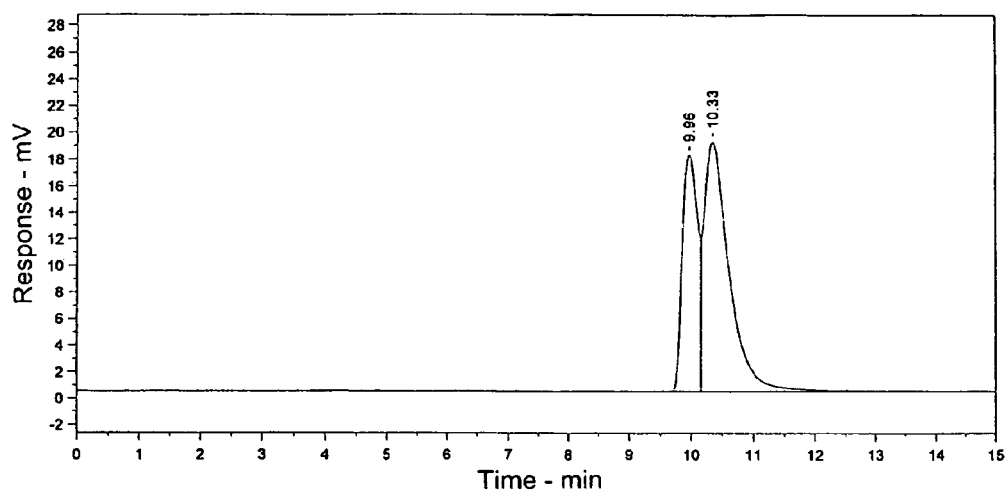
FIG. 90 illustrates a chromatogram of Evaluation Sample 9 in Evaluation 1 of Example 15.

CSP-5 was evaluated for its asymmetry recognition ability with the resultant column under the following evaluation conditions. The racemic bodies of Compounds 1 to 9 were used as samples for evaluation.
[Evaluation (1)]
The evaluation for the asymmetry recognition ability was performed with three kinds of samples for evaluation (Compound Nos.: 3, 6, and 8) under the following conditions by HPLC. Table 16 shows the results of the evaluation. In addition, FIGS. 74 to 76 illustrate the chromatograms of the respective samples for evaluation.
(Evaluation Conditions 1)
　Moving phase: hexane/2-propanol=9/1(v/v)
　Flow rate: 0.4 mL/min.
　Temperature: 25° C.
　Detection: UV 254 nm

TABLE 16

| Sample | 3 | 6 | 8 |
|---|---|---|---|
| t0 | 7.85 | | |
| t1 | 42.54 | 45.05 | 75.15 |
| t2 | 64.57 | 68.61 | 83.96 |
| k1' | 4.42 | 4.74 | 8.57 |
| k2' | 7.23 | 7.74 | 9.70 |
| α | 1.64 | 1.63 | 1.13 |

Example 14

Production of Column for HPLC With CSP-6

CSP-6 (3.5 g) was dispersed in methanol, and then a stainless column having a diameter of 0.46 cm and a length of 25 cm was filled with the resultant slurry according to a slurry mode. Thus, a column filled with CSP-6 was produced.

CSP-6 was evaluated for its asymmetry recognition ability with the resultant column under the following evaluation conditions. The racemic bodies of Compounds 1 to 9 were used as samples for evaluation.
[Evaluation (1)]
The evaluation for the asymmetry recognition ability was performed with six kinds of samples for evaluation (Compound Nos.: 2, 3, 4, 5, 6, and 8) under the following conditions by HPLC. Table 17 shows the results of the evaluation. In addition, FIGS. 77 to 82 illustrate the chromatograms of the respective samples for evaluation.
(Evaluation Conditions 1)
　Moving phase: hexane/2-propanol=9/1(v/v)
　Flow rate: 1.0 mL/min.
　Temperature: 25° C.
　Detection: UV 254 nm (225 nm for Sample 5 alone)

TABLE 17

| Sample | 2 | 3 | 4 | 5 | 6 | 8 |
|---|---|---|---|---|---|---|
| t0 | 3.15 | | | | | |
| t1 | 5.17 | 15.56 | 6.65 | 5.74 | 13.23 | 21.80 |
| t2 | 5.29 | 22.38 | 6.87 | 5.96 | 19.98 | 23.76 |
| k1' | 0.64 | 3.94 | 1.11 | 0.82 | 3.20 | 5.92 |
| k2' | 0.68 | 6.10 | 1.18 | 0.89 | 5.34 | 6.54 |
| α | 1.06 | 1.55 | 1.06 | 1.08 | 1.67 | 1.11 |

Example 15

Production of Column for HPLC With CSP-7

CSP-7 (3.5 g) was dispersed in methanol, and then a stainless column having a diameter of 0.46 cm and a length of 25 cm was filled with the resultant slurry according to a slurry mode. Thus, a column filled with CSP-7 was produced.

CSP-7 was evaluated for its asymmetry recognition ability with the resultant column under the following evaluation conditions. The racemic bodies of Compounds 1 to 9 were used as samples for evaluation.
[Evaluation (1)]
The evaluation for the asymmetry recognition ability was performed with eight kinds of samples for evaluation (Compound Nos.: 1, 2, 3, 4, 5, 6, 8, and 9) under the following conditions by HPLC. Table 18 shows the results of the evaluation. In addition, FIGS. 83 to 90 illustrate the chromatograms of the respective samples for evaluation.
(Evaluation Conditions 1)
　Moving phase: hexane/2-propanol=9/1(v/v)
　Flow rate: 1.0 mL/min.
　Temperature: 25° C.
　Detection: UV 254 nm (225 nm for Sample 5 alone)

TABLE 18

| Sample | 1 | 2 | 3 | 4 | 5 | 6 | 8 | 9 |
|---|---|---|---|---|---|---|---|---|
| t0 | 3.04 | | | | | | | |
| t1 | 19.20 | 7.25 | 25.77 | 12.16 | 8.55 | 38.46 | 71.17 | 9.96 |
| t2 | 20.70 | 7.95 | 54.25 | 13.16 | 9.67 | 63.09 | 77.38 | 10.33 |
| k1' | 5.32 | 1.38 | 7.48 | 3.00 | 1.81 | 11.65 | 22.41 | 2.28 |
| k2' | 5.81 | 1.62 | 16.85 | 3.33 | 2.18 | 19.75 | 24.45 | 2.40 |
| α | 1.09 | 1.17 | 2.25 | 1.11 | 1.20 | 1.70 | 1.09 | 1.05 |

INDUSTRIAL APPLICABILITY

The present invention can provide a novel optical-isomer separating agent for chromatography having a ring structure having an ability to function as a chiral shift reagent as a chiral selector. The separating agent of the present invention can be expected to exert optical-isomer separating performance corresponding to the amount of the ring structure. In addition, the formation of a separating agent having high separating performance for specific optical isomers can be expected from the design of a ring structure corresponding to optical isomers to be separated.

The invention claimed is:

1. An optical-isomer separating agent for chromatography comprising a carrier supporting a compound represented by the following formula (1) through chemical bonding:

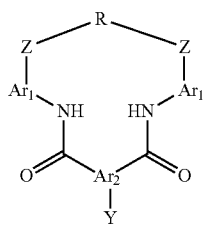
(1)

where R is

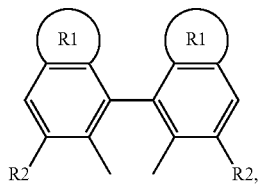
(2)

where, in formula (2), R1 rings each independently represent an aromatic ring, an aliphatic ring, or no ring, R2's each independently represent a hydrogen atom, a linear or branched alkyl group having 1 to 5 carbon atoms, an aromatic group, an ester group, or a halogen atom, $Ar_1$'s each independently represent

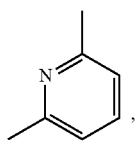

$Ar_2$ represents

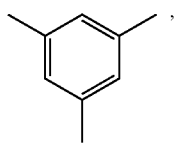

Z's each independently represent —O—CH$_2$—CO—NH—, and Y represents a group which chemically bonds to the carrier.

2. The separating agent according to claim 1, wherein R in formula (1) is represented by the following structural formula (7):

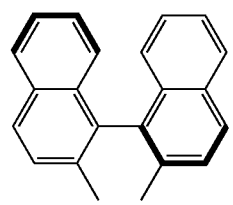
(7)

where an absolute configuration in the general structure (7) may be (R) or (S).

3. The separating agent according to claim 1, wherein the carrier is a silica gel.

4. The separating agent according to claim 3, wherein Y in the formula (1) is a group that reacts with a silanol group to form a siloxane bond.

5. The separating agent according to claim 4, wherein Y's in the formula (1) each are any one of groups represented by the following formulae (16) to (20):

—CO—NH—(CH$_2$)$_n$—Si(OEt)$_3$ (16)

—S—(CH$_2$)$_3$—O—(CH$_2$)$_n$—Si(OEt)$_3$ (17)

—NH—CH$_2$—CH(OH)—(CH$_2$)$_n$—Si(OEt)$_3$ (18)

—CH=N—(CH$_2$)$_n$—Si(OEt)$_3$ (19)

—O—CH$_2$—CO—NH—(CH$_2$)$_n$—Si(OEt)$_3$ (20)

where, in the formulae (16) to (20), n represents an integer of 1 to 20.

6. A process for producing an optical-isomer separating agent for chromatography, the process comprising the steps of:

causing two equivalents of a diamine (II) represented by the following formula (II) and one equivalent of an acid compound (I) represented by the following formula (I) or an acid compound (IV) represented by the following formula (IV) to react with each other to obtain a diamine (III) represented by the following formula (III) or a diamine (VII) represented by the following formula (VII);

causing equal equivalents of the diamine (III) or (VII) and the acid compound (IV) or (I) to react with each other to obtain a cyclic amide compound (V) represented by the following formula (V); and causing Y of the cyclic amide compound (V) and a carrier to react with each other directly or through a crosslinking group to obtain an optical-isomer separating agent for chromatography represented by the following general formula (VI):

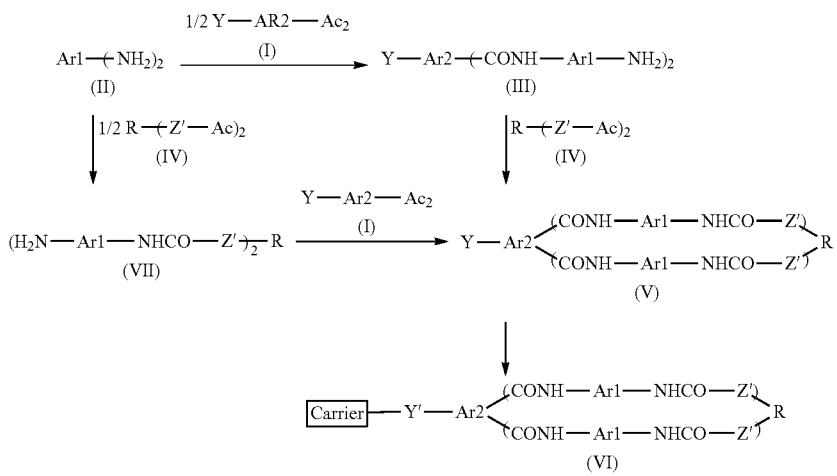

where:
in the formulae (I), (III), (V), and (VI), $Ar_2$ represents

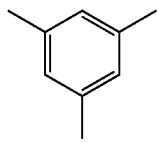

and Y represents: a group which chemically bonds to the carrier;
or, a group having a precursor structure thereof;
in the formulae (I), (III), and (V) to (VII), $Ar_1$'s each independently represent

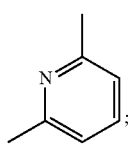

in the formulae (IV) to (VII), R is

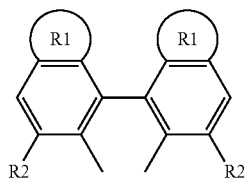

where, in formula (2), R1 rings each independently represent an aromatic ring, an aliphatic ring, or no ring, R2's each independently represent a hydrogen atom, a linear or branched alkyl group having 1 to 5 carbon atoms, an aromatic group, an ester group, or a halogen atom, and Z's each independently represent —O—$CH_2$—CO—NH;
in the formula (VI), Y' represents a group chemically bonded to the carrier; and
in the formulae (I) and (IV), Ac represents a carboxyl group or —COCl.

7. The process for producing a separating agent according to claim 6, the process comprising the steps of:
causing two equivalents of the diamine (II) represented by the formula (II) and one equivalent of the acid compound (I) represented by the formula (I) to react with each other to obtain the diamine (III) represented by the formula (III);

causing equal equivalents of the diamine (III) and the acid compound (IV) to react with each other to obtain the cyclic amide compound (V) represented by the formula (V); and bonding Y of the cyclic amide compound (V) and the carrier to each other directly or through the crosslinking group to obtain the optical-isomer separating agent for chromatography represented by the formula (VI).

8. The process for producing a separating agent according to claim 6, wherein R is represented by the following structural formula (7):

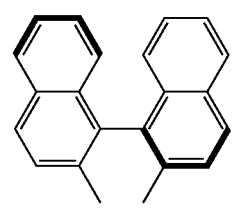

where, an absolute configuration in the general formula (7) may be (R) or (S).

9. The process for producing a separating agent according to claim 6, wherein the carrier is a silica gel.

10. The process for producing a separating agent according to claim 9, wherein the silica gel has been subjected to surface modification with a group serving as the crosslinking group.

11. The process for producing a separating agent according to claim 10, wherein the group serving as the crosslinking group is any one of groups represented by the following formulae (21) to (25):

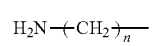 (21)

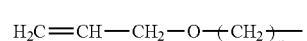 (22)

 (23)

 (24)

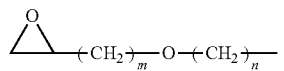 (25)
where, in the general formulae (21) to (25), m and n each represent an integer of 1 to 20.
* * * * *